US011944674B2

United States Patent
Reyes-Sandoval

(10) Patent No.: US 11,944,674 B2
(45) Date of Patent: *Apr. 2, 2024

(54) VACCINES

(71) Applicant: Oxford University Innovation Limited, Oxford (GB)

(72) Inventor: Arturo Reyes-Sandoval, Headington (GB)

(73) Assignee: Oxford University Innovation Limited, Oxford (GB)

(*) Notice: Subject to any disclaimer, the term of this patent is extended or adjusted under 35 U.S.C. 154(b) by 0 days.

This patent is subject to a terminal disclaimer.

(21) Appl. No.: 17/644,019

(22) Filed: Dec. 13, 2021

(65) Prior Publication Data

US 2022/0168409 A1 Jun. 2, 2022

Related U.S. Application Data

(63) Continuation of application No. 16/302,295, filed as application No. PCT/GB2017/051391 on May 18, 2017, now Pat. No. 11,197,920.

(30) Foreign Application Priority Data

May 19, 2016 (GB) ..................................... 1608821

(51) Int. Cl.
| | | |
|---|---|---|
| *A61K 39/002* | (2006.01) | |
| *A61K 39/015* | (2006.01) | |
| *A61K 39/235* | (2006.01) | |
| *A61K 39/285* | (2006.01) | |
| *A61K 39/29* | (2006.01) | |
| *A61K 39/39* | (2006.01) | |
| *A61P 33/06* | (2006.01) | |
| *A61K 39/00* | (2006.01) | |

(52) U.S. Cl.
CPC .......... *A61K 39/015* (2013.01); *A61K 39/235* (2013.01); *A61K 39/285* (2013.01); *A61K 39/29* (2013.01); *A61K 39/39* (2013.01); *A61P 33/06* (2018.01); *A61K 2039/5258* (2013.01); *A61K 2039/6075* (2013.01); *Y02A 50/30* (2018.01)

(58) Field of Classification Search
None
See application file for complete search history.

(56) References Cited

U.S. PATENT DOCUMENTS

| | | | |
|---|---|---|---|
| 4,235,877 | A | 11/1980 | Fullerton |
| 6,399,062 | B1 | 6/2002 | Charoenvit et al. |
| 11,197,920 | B2 | 12/2021 | Reyes-Sandoval |
| 2008/0057085 | A1 | 3/2008 | Sim et al. |
| 2010/0150998 | A1 | 6/2010 | Cohen et al. |
| 2010/0272745 | A1 | 10/2010 | Lemoine et al. |
| 2010/0272788 | A1 | 10/2010 | Cohen et al. |
| 2011/0262469 | A1 | 10/2011 | Herrera Valencia et al. |

FOREIGN PATENT DOCUMENTS

| | | |
|---|---|---|
| WO | WO-2006/088597 A2 | 8/2006 |
| WO | WO-2008/009650 A2 | 1/2008 |
| WO | WO-2008/009652 A2 | 1/2008 |
| WO | WO-2009/080715 A2 | 7/2009 |
| WO | WO-2009/080803 A1 | 7/2009 |
| WO | WO-2009/082440 A2 | 7/2009 |
| WO | WO-2014/111733 A1 | 7/2014 |
| WO | WO-2016/046113 A1 | 3/2016 |

OTHER PUBLICATIONS

Almeida et al., "Long-lasting humoral and cellular immune responses elicited by immunization with recombinant chimeras of the Plasmodium vivax circumsporozoite protein". Vaccine, 2014. 32(19): p. 2181-7.

Aricescu et al., "A time- and cost-efficient system for high-level protein production in mammalian cells", Acta Crystallogr D Biol Crystallogr, 2006. 62(Pt 10): p. 1243-50.

Bauza et al., "Efficacy of a Plasmodium vivax malaria vaccine using ChAd63 and modified vaccinia Ankara expressing thrombospondin-related anonymous protein as assessed with transgenic Plasmodium berghei parasites", Infect Immun, 2014. 82(3): p. 1277-86.

Bennett et al., "Phase 1/2a Trial of Plasmodium vivax Malaria Vaccine Candidate VMP001/AS01B in Malaria-Naive Adults: Safety, Immunogenicity, and Efficacy", PLoS Negl Trop Dis, 2016. 10(2): p. e0004423.

Cabrera-Mora et al., "Induction of Multifunctional Broadly Reactive T Cell Responses by a Plasmodium vivax Circumsporozoite Protein Recombinant Chimera", Infect Immun, 2015. 83(9): p. 3749-61.

Cespedes et al., "Antigenicity and immunogenicity of a novel chimeric peptide antigen based on the P. vivax circumsporozoite protein", Vaccine, 2013. 31(42): p. 4923-30.

(Continued)

*Primary Examiner* — Jennifer E Graser
(74) *Attorney, Agent, or Firm* — Clark & Elbing LLP

(57) ABSTRACT

The present invention relates to particles, particularly virus-like particles (VLPs), comprising fusion polypeptides comprising selected repeat units derived from the repeating regions of Type I and Type II circumsporozoite proteins (CSP) of *Plasmodium vivax* (Pv), together with an amino acid sequence derived from the C-terminal PvCSP sequence. In some embodiments, the fusion polypeptide additionally comprises an amino acid sequence derived from the N-terminal PvCSP sequence and/or a surface antigen polypeptide derived from Hepatitis B virus (HBV-S). The invention also relates to nucleotide sequences coding for such fusion polypeptides, vectors and plasmids comprising such nucleotide sequences, and host cells comprising such vectors and plasmids. The invention additionally relates to compositions, particularly vaccine compositions, comprising the fusion polypeptides or VLPs for use as vaccines for the prevention of malaria.

8 Claims, 27 Drawing Sheets
Specification includes a Sequence Listing.

(56) References Cited

OTHER PUBLICATIONS

Cespedes et al., "Antigenicity and immunogenicity of a novel Plasmodium vivax circumsporozoite derived synthetic vaccine construct". Vaccine, 2014. 32(26): p. 3179-86.
Collins et al., "Enhancing protective immunity to malaria with a highly immunogenic virus-like particle vaccine," Scientific reports. 7:46621 (2017).
Coppi et al., "The malaria circumsporozoite protein has two functional domains, each with distinct roles as sporozoites journey from mosquito to mammalian host", J. Exp. Med. vol. 208 No. 2 341-356 (2011).
Cui et al., "Genetic diversity and multiple infections of Plasmodium vivax malaria in Western Thailand,". Am J Trop Med Hyg. 68(5):613-9 (2003).
Duffy et al., "Pre-erythrocytic malaria vaccines: identifying the targets," Expert Rev Vaccines. 11(10): p. 1261-80 (2012).
Espinosa et al., "Development of a chimeric Plasmodium berghei strain expressing the repeat region of the P. vivax circumsporozoite protein for in vivo evaluation of vaccine efficacy," Infect Immun. 81(8): p. 2882-7 (2013).
Ewer et al., "Protective CD8+ T-cell immunity to human malaria induced by chimpanzee adenovirus-MVA immunisation," Nat Commun. 4: p. 2836 (2013).
Galinski et al., "Plasmodium vivax: who cares?" Malar J. 7 Suppl 1: p. S9 (2008).
Gantt et al., "Cell adhesion to a motif shared by the malaria circumsporozoite protein and thrombospondin is mediated by its glycosaminoglycan-binding region and not by CSVTCG," J Biol Chem. 272(31): p. 19205-13 (1997).
Golenda et al., "Continuous in vitro propagation of the malaria parasite Plasmodium vivax," Proc Natl Acad Sci U S A. 94(13): p. 6786-91 (1997).
Guerra et al., "The international limits and population at risk of Plasmodium vivax transmission in 2009," PLoS Negl Trop Dis. 4(8): p. e774 (2010).
Hisaeda et al., "Antibodies to malaria vaccine candidates Pvs25 and Pvs28 completely block the ability of Plasmodium vivax to infect mosquitoes," Infect Immun. 68(12):6618-23 (2000).
Hodgson et al., "Evaluation of the efficacy of ChAd63-MVA vectored vaccines expressing circumsporozoite protein and ME-TRAP against controlled human malaria infection in malaria-naive individuals," J Infect Dis. 211(7): p. 1076-86 (2015).
Lim et al., "Plasmodium vivax: recent world expansion and genetic identity to Plasmodium simium," Proc Natl Acad Sci U S A. 102(43): p. 15523-8 (2005).
Lin et al., "A novel 'gene insertion/marker out' (GIMO) method for transgene expression and gene complementation in rodent malaria parasites," PLoS One. 6(12): p. e29289 (2011).
Longley et al., "Comparative assessment of vaccine vectors encoding ten malaria antigens identifies two protective liver-stage candidates," Sci Rep. 5: p. 11820 (2015).
Markus, "Malaria: origin of the term "hypnozoite"". J Hist Biol. 44(4): p. 781-6 (2011).
Mikayama et al., "Molecular cloning and functional expression of a cDNA encoding glycosylation-inhibiting factor," Proc Natl Acad Sci USA. 90(21):10056-60 (1993).
Miura et al., "Development and characterization of a standardized ELISA including a reference serum on each plate to detect antibodies induced by experimental malaria vaccines," Vaccine. 26(2): p. 193-200 (2008).
Mizutani et al., "Baculovirus-vectored multistage Plasmodium vivax vaccine induces both protective and transmission-blocking immunities against transgenic rodent malaria parasites," Infect Immun. 82(10): p. 4348-57 (2014).
Moon et al. "Enhancing humoral responses to a malaria antigen with nanoparticle vaccines that expand T sub fh cells and promote germinal center induction" PNAS 109(4). 1180-85 (2012).

Moorthy et al., "Immunological mechanisms underlying protection mediated by RTS,S: a review of the available data," Malar J. 8:312 (2009).
Nahrendorf et al., "Memory B-cell and antibody responses induced by Plasmodium falciparum sporozoite immunization," J Infect Dis. 210(12): p. 1981-90 (2014).
Nardin et al., "Phase I testing of a malaria vaccine composed of hepatitis B virus core particles expressing Plasmodium falciparum circumsporozoite epitopes," Infect Immun. 72(11):6519-27 (2004).
Oliveira-Ferreira et al. "HLA class II and antibody responses to circumsporozoite protein repeats of P. vivax (VK210, VK247 and P. vivax like) in individuals naturally exposed to malaria," Acta trop. 92(1):63-69 (2004).
Orr et al., "Improved negative selection protocol for Plasmodium berghei in the rodent malarial model," Malar J. 11:103 (2012).
Pialek, "MultiMalVax Report; Summary periodic report summary 2, Project context and objectives" (2016).
Qari et al. "Global occurrence of plasmodium vivax-like human malaria parasite," The journal of infectious diseases. 168, 1485-9 (1993).
Reimer et al., "Matrix-M adjuvant induces local recruitment, activation and maturation of central immune cells in absence of antigen," PLoS One. 7(7): p. e41451 (2012).
Reyes-Sandoval et al., "CD8+ T effector memory cells protect against liver-stage malaria," J Immunol. 187(3): p. 1347-57 (2011).
Reyes-Sandoval et al., "Development of a plasmodium vivax malaria vaccine for clinical applications using transgenic parasites, virus-like particles and recombinant viruses," Malaria Journal. 13(Suppl1):P77 (2014).
Reyes-Sandoval et al., "Prime-boost immunization with adenoviral and modified vaccinia virus Ankara vectors enhances the durability and polyfunctionality of protective malaria CD8+ T-cell responses," Infect Immun. 78(1): p. 145-53 (2010).
Reyes-Sandoval, et al., "Single-dose immunogenicity and protective efficacy of simian adenoviral vectors against Plasmodium berghei," Eur J Immunol. 38(3): p. 732-41 (2008).
Rts, "Efficacy and safety of the RTS,S/AS01 malaria vaccine during 18 months after vaccination: a phase 3 randomized, controlled trial in children and young infants at 11 African sites," PLoS Med. 11(7): p. e1001685 (2014).
Rudinger, "Characteristics of the amino acids as components of a peptide hormone sequence," in Peptide Hormones, Parsons, ed., University Park Press, Jun. 1976, pp. 1-7.
Salman et al. "Rational development of a protective P. vivax vaccine evaluated with transgenic rodent parasite challenge models," Scientific reports. 7:46482 (2017).
Sun et al., "Protective immunity induced with malaria vaccine, RTS, S, is linked to Plasmodium falciparum circumsporozoite protein-specific CD4+ and CD8+ T cells producing IFN-gamma," J Immunol. 171(12): p. 6961-7 (2003).
Targett et al., "Malaria vaccine research and development: the role of the WHO MALVAC committee," Malar J. 12:362 (2013).
Teixeira et al., "Immunogenicity of a prime-boost vaccine containing the circumsporozoite proteins of Plasmodium vivax in rodents," Infect Immun. 82(2): p. 793-807 (2014).
Vanloubbeeck et al., "Comparison of the immune responses induced by soluble and particulate Plasmodium vivax circumsporozoite vaccine candidates formulated in AS01 in rhesus macaques," Vaccine. 31(52): p. 6216-24 (2013).
Warimwe et al., "Peripheral blood monocyte-to-lymphocyte ratio at study enrollment predicts efficacy of the RTS,S malaria vaccine: analysis of pooled phase II clinical trial data," BMC Med. 11:184 (2013).
Whitacre et al., "P. falciparum and P. vivax Epitope-Focused VLPs Elicit Sterile Immunity to Blood Stage Infections," PLoS One. 1;10(5):e0124856 (2015).
White, "Determinants of relapse periodicity in Plasmodium vivax malaria," Malar J. 10:297 (2011).
Yadava et al., "A novel chimeric plasmodium vivax circumsporozoite protein induces biologically functional antibodies that recognise both VK210 and VK247 sporozoites," Infection and Immunity, American Society for Microbiology. 75(3) 1177-1185 (2007).

(56) References Cited

OTHER PUBLICATIONS

Yadava et al., "Protective efficacy of a Plasmodium vivax circumsporozoite protein-based vaccine in Aotus nancymaae is associated with antibodies to the repeat region," PLoS Negl Trop Dis. 8(10): p. e3268 (2014).
Greenspan et al., "Defining epitopes: It's not as easy as it seems," Nat Biotechnol. 17(10):936-7 (1999).
Chothia et al., "The relation between the divergence of sequence and structure in proteins," EMBO J. 5(4):823-6 (1986).

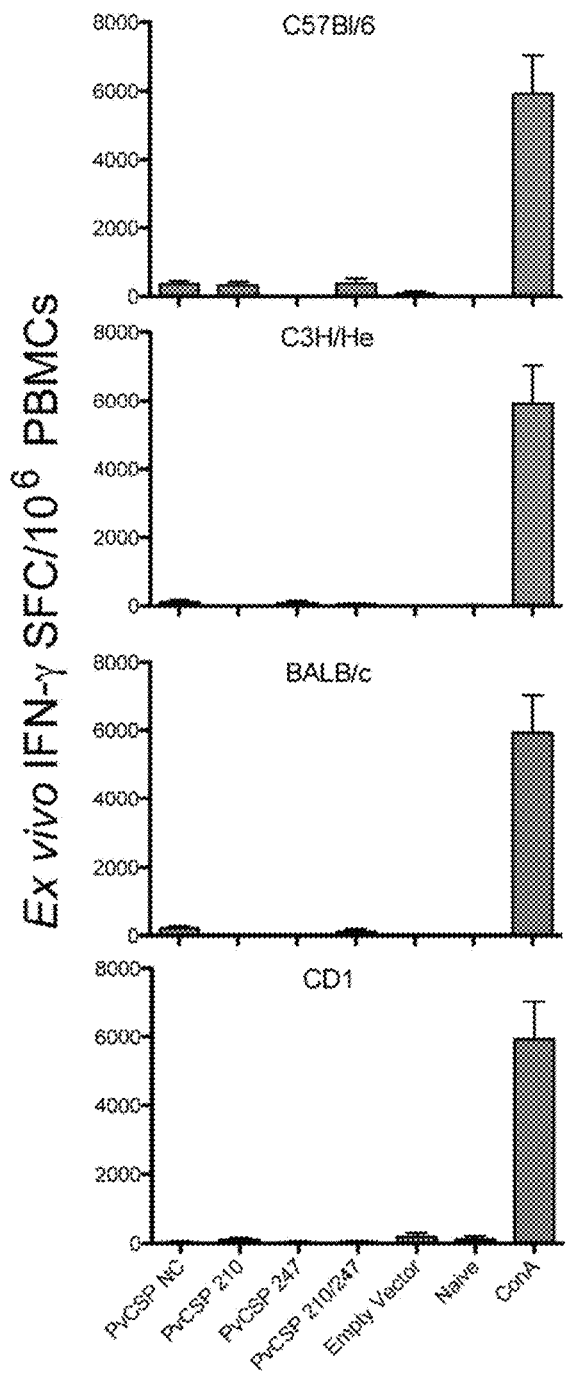
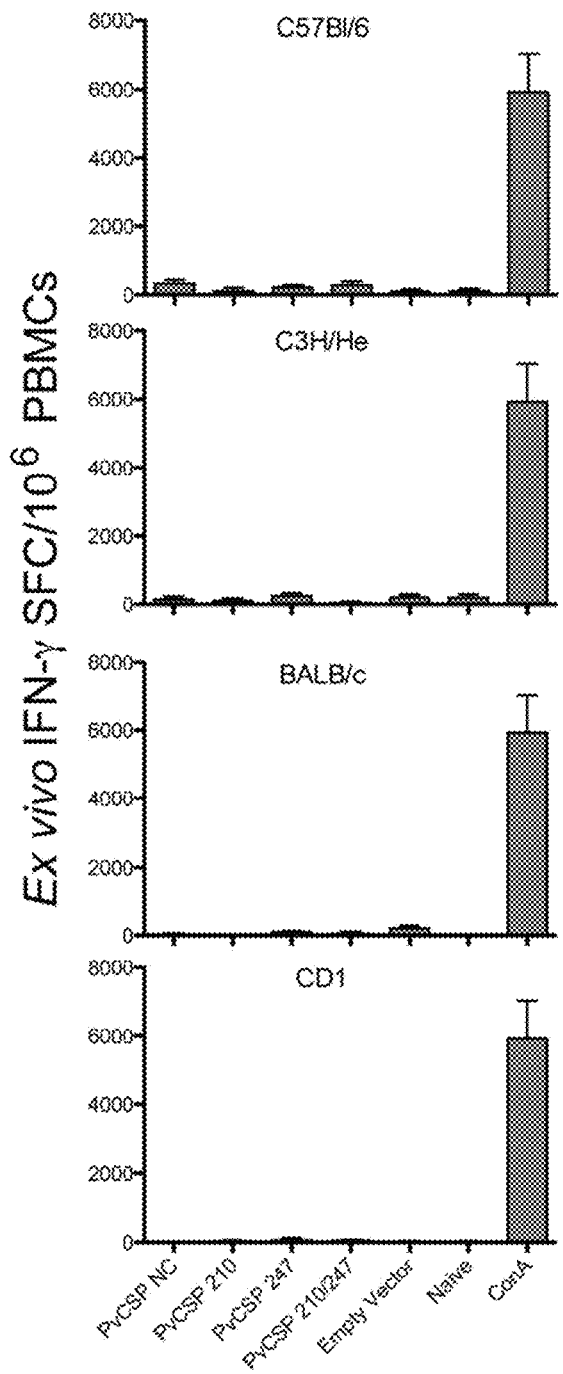

PbANKA-PvCSP-210(r)PbCSP
Chimeric line (2196 cl1)

PbANKA-PvCSP-247(r)PbCSP
Chimeric line (2199 cl1)

WT P. berghei
Control line (676m1cl1)

Full (N, 210, 247 and C)

Truncated (210, 247 and C)

Survival of mice using PvCSP full sequence vs PvCSP truncated without N-terminal

VACCINES

The present invention relates to particles, particularly virus-like particles (VLPs), comprising fusion polypeptides comprising selected repeat units derived from the repeating regions of Type I and Type II circumsporozoite proteins (CSP) of *Plasmodium vivax* (Pv), together with an amino acid sequence derived from the C-terminal PvCSP sequence. In some embodiments, the fusion polypeptide additionally comprises an amino acid sequence derived from the N-terminal PvCSP sequence and/or a surface antigen polypeptide derived from Hepatitis B virus (HBV-S). The invention also relates to nucleotide sequences coding for such fusion polypeptides, vectors and plasmids comprising such nucleotide sequences, and host cells comprising such vectors and plasmids. The invention additionally relates to compositions, particularly vaccine compositions, comprising the fusion polypeptides or VLPs for use as vaccines for the prevention of malaria.

*Plasmodium vivax* malaria poses a major health risk to 2.85 billion people worldwide living in tropical, sub-tropical and temperate regions. *P. vivax* is the most widely distributed human malaria parasite in the world and considered to be the most difficult to control and eliminate from endemic regions. This is largely due to the parasite's ability to remain latent in the liver of infected people and to subsequently reactivate, possibly weeks to years after an initial infection.

*Plasmodium* sporozoites enter the blood stream through an infectious mosquito bite and quickly migrate and invade the liver. This 'pre-erythrocytic' stage is an attractive vaccine candidate. Currently, RTS,S/AS01 is the most advanced platform, aiming at preventing *P. falciparum* infection by stimulating immune responses against the major *Plasmodium* sporozoite surface antigen, i.e. the circumsporozoite protein (CSP). RTS,S/AS01 presents a hybrid polypeptide consisting of a portion of the *P. falciparum* CSP repeat and C-terminal regions fused to the amino terminal end of the hepatitis B virus surface (HepB-S) protein. RTS,S/AS01 has undergone extensive clinical testing and has been shown to induce significant protective immunity in Phase III trials.

The homologous CSP protein of *P. vivax* (PvCSP) is also actively being investigated as a component of a pre-erythrocytic vaccine against *P. vivax*. Some of these vaccines include the PvCSP VK210 (Type I) and VK247 (Type II) central repeats to try to induce protection against both types of parasites circulating worldwide.

WO2008/009652 relates to novel hybrid/fusion proteins comprising repeat units derived from the repeating regions of Type I and Type II CSPs of *P. vivax*, the N-terminal PvCSP sequence and a surface antigen S derived from Hepatitis B virus (HBV). The claims of this patent application refer to 1-15 Type I repeats; and 5 or less Type II repeats.

WO2009/080803 relates to immunogenic protein particles comprising a fusion protein comprising sequences derived from a CS protein of *P. vivax*, the N-terminal PvCSP sequence and the S antigen of HBV, together with an S antigen derived from HBV. This is referred to therein as CSV-S,S.

There remains a need, however, for improved antigens for use in inducing protective immunity against malaria.

A new fusion polypeptide comprising certain selected Type I and Type II repeat units from the CSPs of *P. vivax* and an amino acid sequence derived from the C-terminal PvCSP sequence has now been developed. In some embodiments, this fusion polypeptide additionally comprises an amino acid sequence derived from the N-terminal PvCSP sequence and/or a surface antigen polypeptide derived from Hepatitis B virus (HBV-S). Fusion polypeptides which comprise the surface antigen polypeptide derived from Hepatitis B virus (HBV-S) can be used to present the PvCSP antigen in a virus like particle (VLP); this is referred to herein as Rv21.

It is shown herein that vaccination with the fusion polypeptide antigen of the current invention induces protective immune responses against sporozoites expressing either one of the PvCSP VK210 or VK247 alleles. Moreover, it has been found that an immunization protocol using Rv21 VLPs induced complete, sterile protection against a stringent sporozoite challenge, surpassing the efficacy of viral-vectored vaccines expressing a similar PvCSP antigen. These studies highlight the potential and utility of Rv21 VLPs to support the development of an efficacious *P. vivax* malaria vaccine.

It is therefore an object of the invention to provide an immunogenic fusion polypeptide and VLPs comprising such polypeptides which are capable of inducing protective and/or neutralising antibodies against a sporozoite challenge.

In one embodiment, the invention provides a particle comprising a fusion polypeptide, wherein the fusion polypeptide comprises:
(i) at least 6 repeat units derived from the repeating region of a Type I circumsporozoite protein (CSP) of *Plasmodium vivax*;
(ii) at least 6 repeat units derived from the repeating region of a Type II circumsporozoite protein (CSP) of *Plasmodium vivax*;
(iii) an amino acid sequence of or derived from the C-terminal fragment of CSP of *Plasmodium vivax*; and
(iv) an amino acid sequence of or derived from the Hepatitis B virus surface antigen.

The invention also provides a fusion polypeptide, wherein the fusion polypeptide comprises:
(i) at least 6 repeat units derived from the repeating region of a Type I circumsporozoite protein (CSP) of *Plasmodium vivax*;
(ii) at least 6 repeat units derived from the repeating region of a Type II circumsporozoite protein (CSP) of *Plasmodium vivax*; and
(iii) an amino acid sequence of or derived from the C-terminal fragment of CSP of *Plasmodium vivax*.

In some embodiments, the fusion polypeptide additionally comprises an amino acid sequence of or derived from the N-terminal fragment of CSP of *Plasmodium vivax* and/or an amino acid sequence of or derived from the Hepatitis B virus surface antigen.

Preferably, the fusion polypeptide comprises:
(i) 8-12 repeat units derived from the repeating region of a Type I circumsporozoite protein (CSP) of *Plasmodium vivax*; and/or
(ii) 8-12 repeat units derived from the repeating region of a Type II circumsporozoite protein (CSP) of *Plasmodium vivax*.

The fusion polypeptide comprises at least three parts, i.e. parts (i)-(iii); in some embodiments it has at least four parts (i.e. (i)-(iv)) or more. These parts are either joined contiguously or short linker amino acids may be used to join the parts together.

The parts may or may not be joined in the order (i)-(iii) or (i)-(iv) (N- to C-orientation). Preferably, they are joined in the order (i)-(iii) or (i)-(iv) (N- to C-orientation) with no linkers.

The circumsporozoite protein (CSP) of *Plasmodium* species is characterized by a central domain (repeat region) flanked by non-repetitive amino (N-terminus) and carboxy (C-terminus) fragments.

The central domain of *P. vivax* is composed of several blocks of a repeat unit. Generally each repeat unit consists of 9-amino acids.

At least two forms of the *P. vivax* CSP are known: these are designated VK210 or Type I; and VK247 or Type II. These two forms are exemplified by SEQ ID NOs: 1-2.

As used herein, the term "Type I repeat units" refers to repeat units derived from the repeating region of a Type I circumsporozoite protein (CSP) of *Plasmodium vivax*. Similarly, as used herein, the term "Type II repeat units" refers to repeat units derived from the repeating region of a Type II circumsporozoite protein (CSP) of *Plasmodium vivax*.

In some embodiments, the Type I repeat unit is derived from one or more of the following strains of *P. vivax*: KCSP95-50, KCSP96-21, KCSP97-75, North Korea, C-2, CH-3, CH-4, CH-5, NYUThai, India VII, PH-46, PH-79, SOL-83, SOL-101, Mauritania, Sal-1, Brazil or Belem.

In some embodiments, the Type II repeat unit is derived from one or more of the following strains of *P. vivax*: Papua New Guinea (PNG, PNG 4/B), Brazil: Paragaminos (BZL B7-4, BZL B19-2) Brazil (*P. simium*), Gabon or Bangladesh.

Examples of Type I repeat units include the following:

```
                                                (SEQ ID NO: 3)
GDRAAGQPA (SEQ ID NO: 4)
GDRADGQPA (SEQ ID NO: 5)
GNGAGGQAA
```

Examples of Type II repeat units include the following:

```
                                                (SEQ ID NO: 6)
ANGAGNQPG (SEQ ID NO: 7)
ANGAGGQAA (SEQ ID NO: 8)
ANGAGDQPG (SEQ ID NO: 9)
ANGADDQPG (SEQ ID NO: 10)
EDGAGNQPG
```

The invention also relates to derivatives of the repeat units disclosed herein wherein one or more of the repeat unit sequences independently comprise 1, 2, 3, 4 or 5 conservative amino acid modifications. The modifications may or may not be present in all of the repeat units. As used herein, the term "conservative sequence modifications" is intended to refer to amino acid modifications that do not significantly affect or alter ability of the fusion polypeptide to induce protective immunity against *P. vivax* CSP. Such conservative modifications include amino acid substitutions, additions and deletions. Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acids of the repeat units may be replaced with another amino acid from the same side chain family, and the modified amino acid sequence may be tested to evaluate its ability to induce protective immunity against *P. vivax* CSP.

In some embodiments, one or more of the repeat unit sequences independently comprise 1 or 2 conservative amino acid substitutions. In some embodiments, one or more of the repeat unit sequences independently comprise 1 or 2 amino acid additions or deletions.

Preferably, the Type II repeat units are present as one or more of the following repeat unit pairs:

```
                                                (SEQ ID NO: 11)
ANGAGNQPG-ANGAGGQAA (SEQ ID NO: 12)
ANGAGDQPG-ANGAGDQPG (SEQ ID NO: 13)
ANGADDQPG-ANGAGDQPG (SEQ ID NO: 14)
EDGAGNQPG-ANGAGDQPG
```

Preferably, the at least 6 Type I repeat units comprise 5 blocks of the repeat unit GDRAAGQPA (SEQ ID NO: 3), more preferably 5 contiguous repeat units.

Preferably, the at least 6 Type I repeat units comprise 4 blocks of the repeat unit GDRADGQPA (SEQ ID NO: 4), more preferably 4 contiguous repeat units.

Preferably, the at least 6 Type I repeat units comprise 1 block of the repeat unit

```
                                                (SEQ ID NO: 5)
GNGAGGQAA.
```

Preferably, the at least 6 Type II repeat units comprise 2 blocks of the repeat unit pair ANGAGNQPG-ANGAGGQAA (SEQ ID NO: 11), more preferably 2 contiguous repeat units pairs.

Preferably, the at least 6 Type II repeat units comprise 1 block of the repeat unit pair

```
                                                (SEQ ID NO: 12)
ANGAGDQPG-ANGAGDQPG.
```

Preferably, the at least 6 Type II repeat units comprise 1 block of the repeat unit pair

```
                                                (SEQ ID NO: 13)
ANGADDQPG-ANGAGDQPG.
```

Preferably, the at least 6 Type II repeat units comprise 1 block of the repeat unit pair

```
                                                (SEQ ID NO: 14)
EDGAGNQPG-ANGAGDQPG.
```

Preferably, the at least 6 repeat units derived from the repeating region of a Type I circumsporozoite protein (CSP) of *Plasmodium vivax* comprise the following numbers of the following repeat units:

(GDRAAGQPA)*5 (SEQ ID NO: 3)

(GDRADGQPA)*4 (SEQ ID NO: 4)

(GNGAGGQAA)*1 (SEQ ID NO: 5)

wherein the above repeat units are preferably joined contiguously in the above order in a N—C orientation.

As used herein, the term "at least 6 repeat units derived from the repeating region of a Type I circumsporozoite protein (CSP) of *Plasmodium vivax*" includes amino acid sequences having at least 80% sequence identity to SEQ ID NO: 16 (preferably at least 85%, 90%, 95%, 96%, 97%, 98% or 99% sequence identity) and having the ability to induce protective immunity against *P. vivax* CSP.

As used herein, the term "at least 6 repeat units derived from the repeating region of a Type I circumsporozoite protein (CSP) of *Plasmodium vivax*" also includes fragments of SEQ ID NO: 16 which are at least 50% of the length of SEQ ID NO: 16 (preferably at least 60%, 70%, 80% or 90% of the length) and having the ability to induce protective immunity against *P. vivax* CSP.

Preferably, the at least 6 repeat units derived from the repeating region of a Type II circumsporozoite protein (CSP) of *Plasmodium vivax* comprise the following numbers of the following repeat units:

(ANGAGNQPG/ANGAGGQAA)*2 (SEQ ID NO: 11)

(ANGAGDQPG/ANGAGDQPG)*1 (SEQ ID NO: 12)

(ANGADDQPG/ANGAGDQPG)*1 (SEQ ID NO: 13)

(EDGAGNQPG/ANGAGDQPG)*1 (SEQ ID NO: 14)

wherein the above repeat units are preferably joined contiguously in the above order in a N—C orientation.

As used herein, the term "at least 6 repeat units derived from the repeating region of a Type II circumsporozoite protein (CSP) of *Plasmodium vivax*" includes amino acid sequences having at least 80% sequence identity to SEQ ID NO: 18 (preferably at least 85%, 90%, 95%, 96%, 97%, 98% or 99% sequence identity) and having the ability to induce protective immunity against *P. vivax* CSP.

As used herein, the term "at least 6 repeat units derived from the repeating region of a Type II circumsporozoite protein (CSP) of *Plasmodium vivax*" also includes fragments of SEQ ID NO: 18 which are at least 50% of the length of SEQ ID NO: 18 (preferably at least 60%, 70%, 80% or 90% of the length) and having the ability to induce protective immunity against *P. vivax* CSP.

Most preferably, the invention provides a fusion polypeptide comprising an amino acid sequence comprising the following repeat units:

(GDRAAGQPA)*5 (SEQ ID NO: 3)

(GDRADGQPA)*4 (SEQ ID NO: 4)

(GNGAGGQAA)*1 (SEQ ID NO: 5)

(ANGAGNQPG-ANGAGGQAA)*2 (SEQ ID NO: 11)

(ANGAGDQPG-ANGAGDQPG)*1 (SEQ ID NO: 12)

(ANGADDQPG-ANGAGDQPG)*1 (SEQ ID NO: 13)

(EDGAGNQPG-ANGAGDQPG)*1 (SEQ ID NO: 14)

wherein the above repeat units are joined contiguously in the above order in a N—C orientation.

As used herein, the term "*5", etc., means multiplied by 5, etc., i.e. 5 contiguous repeated blocks of that sequence. The same applies to "*4", "*2" and "*1", mutatis mutandis.

In some embodiments, the fusion polypeptide as defined herein additionally comprises at least one repeat unit derived from the repeating region of a circumsporozoite protein (CSP) of *Plasmodium vivax*-like malaria parasite.

*Plasmodium vivax*-like malaria parasites are described, for example, in Shoukat et al. [60].

Preferably, the amino acid sequence of the repeat unit is APGANQ(E/G)GGAA (SEQ ID NO: 19).

Most preferably, the repeat unit is APGANQEGGAA (SEQ ID NO: 20) or APGANQGGGAA (SEQ ID NO: 21).

Preferably, the fusion polypeptide comprises 1-10, most preferably 4-8, even more preferably 6 of these repeat units.

Most preferably, the fusion polypeptide comprises:

(APGANQEGGAA)*3 (SEQ ID NO: 20)

(APGANQGGGAA)*3. (SEQ ID NO: 21)

As used herein, the term "at least one repeat unit derived from the repeating region of a circumsporozoite protein (CSP) of *Plasmodium vivax*-like malaria parasite" includes amino acid sequences having at least 80% sequence identity to one or more of SEQ ID 23 or 25-27 (preferably at least 85%, 90%, 95%, 96%, 97%, 98% or 99% sequence identity) and having the ability to induce protective immunity against *P. vivax*-like CSP.

As used herein, the term "at least one repeat unit derived from the repeating region of a circumsporozoite protein (CSP) of *Plasmodium vivax*-like malaria parasite" also includes fragments of SEQ ID NOs: 29-32 which are at least 50% of the length of SEQ ID NOs: 29-32 (preferably at least 60%, 70%, 80% or 90% of the length) and having the ability to induce protective immunity against *P. vivax*-like CSP.

These *Plasmodium vivax*-like repeat units are preferably placed adjacent to the other repeat units, i.e. downstream of the N-terminal CSP sequence (if present) and upstream of the C-terminal CSP sequence. Most preferably, these *Plasmodium vivax*-like repeat sequences are positioned immediately downstream of the *P. vivax* Type II repeat units, and immediately upstream of the C-terminal CSP sequence.

The fusion polypeptide also comprises (iii) an amino acid sequence of or derived from the C-terminal fragment of CSP of *Plasmodium vivax*.

The complete C-terminal fragment from CSP of *Plasmodium vivax* is given in SEQ ID NO: 29. Preferably, the C-terminal fragment consists of or comprises SEQ ID NO: 29.

More preferably, the amino acid sequence derived from the C-terminal fragment of CSP of *Plasmodium vivax* comprises or consists of SEQ ID NO: 30,
or

EWTPCSVTCG (SEQ ID NO: 31)

or

CSVTCG. (SEQ ID NO: 32)

The fusion polypeptide may also comprise an insertion of the sequence GAGGQAAGGNA (SEQ ID NO: 33) in the insertion region (IR) of the CSP. The IR lies between the central repeat region and the C-terminal sequence.

The amino acid sequence derived from the C-terminal fragment of CSP of *Plasmodium vivax* is preferably positioned in the fusion polypeptide downstream of the blocks of Type II repeat units (and downstream of the *P. vivax*-like repeat sequences, when present), and before the HBV S antigen sequence (when present).

As used herein, the term "amino acid sequence derived from the C-terminal fragment of CSP" includes amino acid sequences having at least 80% sequence identity to one or more of SEQ ID NOs: 29-32 (preferably at least 85%, 90%, 95%, 96%, 97%, 98% or 99% sequence identity) and comprising one or more T-cell epitopes which promote the immunogenicity of the Type I and/or Type II repeat units.

As used herein, the term "amino acid sequence derived from the C-terminal fragment of CSP" also includes fragments of SEQ ID NOs: 29-32 which are at least 50% of the length of SEQ ID NOs: 29-32 (preferably at least 60%, 70%, 80% or 90% of the length) and comprising one or more T-cell epitopes which promote the immunogenicity of the Type I and/or Type II repeat units.

In some embodiments of the invention, the fusion polypeptide additionally comprises an amino acid sequence of or derived from the N-terminal fragment of CSP of *Plasmodium vivax* or *Plasmodium falciparum*, preferably from *P. vivax*.

The complete N-terminal fragment from CSP of *Plasmodium vivax* is given in SEQ ID NO: 35. Preferably, the N-terminal fragment sequence comprises SEQ ID NO: 35.

More preferably, the N-terminal fragment comprises KLKQP (SEQ ID NO: 36).

The N-terminal fragment of CSP of *Plasmodium vivax* or *Plasmodium falciparum* is preferably positioned, when present, at the N-terminus of the fusion polypeptide (i.e. upstream of the blocks of repeats).

In some embodiments of the invention, the particle and fusion polypeptide does not comprise an amino acid sequence derived from the N-terminal fragment of CSP of *Plasmodium vivax* or *Plasmodium falciparum*.

In some particular embodiments of the invention, the particle and fusion polypeptide does not comprise an amino acid sequence of SEQ ID NO: 35 or a variant thereof having at least 90% sequence identity thereto.

As used herein, the term "amino acid sequence derived from the N-terminal fragment of CSP" includes amino acid sequences having at least 80% sequence identity to SEQ ID NO: 35 (preferably at least 85%, 90%, 95%, 96%, 97%, 98% or 99% sequence identity) and comprising one or more T-cell epitopes which promote the immunogenicity of the Type I and/or Type II repeat units.

As used herein, the term "amino acid sequence derived from the N-terminal fragment of CSP" also includes fragments of SEQ ID NO: 35 which are at least 50% of the length of SEQ ID NO: 35 (preferably at least 60%, 70%, 80% or 90% of the length) and comprising one or more T-cell epitopes which promote the immunogenicity of the Type I and/or Type II repeat units.

The particle of the invention comprises (iv) an amino acid sequence of or derived from Hepatitis B virus surface antigen.

The HBV surface antigen (i.e. HBV SAg) increases the immunogenicity of the CSP portion of the fusion polypeptide.

In some embodiments, the HBV surface antigen is derived from an adw serotype.

The complete amino acid sequence of the HBV surface antigen derived from an adw serotype is given in SEQ ID NO: 38.

The invention extends to fusion polypeptides comprising an amino acid sequence derived from Hepatitis B virus surface antigen S as given in SEQ ID NO: 38.

Preferably, the amino acid sequence derived from the Hepatitis B virus surface antigen comprises or consists of the amino acid sequence given in SEQ ID NO: 38.

As used herein, the term "amino acid sequence derived from the Hepatitis B virus surface antigen" includes amino acid sequences having at least 80% sequence identity to SEQ ID NO: 38 (preferably at least 85%, 90%, 95%, 96%, 97%, 98% or 99%) and having the ability to increase the immunogenicity of parts (i)-(iii) of the fusion polypeptide of the invention.

As used herein, the term "amino acid sequence derived from the Hepatitis B virus surface antigen" also includes fragments of SEQ ID NO: 38 which are at least 80% of the length of SEQ ID NO: 38 (preferably at least 90%, 95%, 96%, 97%, 98% or 99%) and having the ability to increase the immunogenicity of parts (i)-(iii) of the fusion polypeptide of the invention.

The amino acid sequence derived from the Hepatitis B virus surface antigen must also be capable of forming virus-like particles (VLPs).

In one preferred embodiment, the invention provides a fusion polypeptide consisting of or comprising the amino acid sequence as given in SEQ ID NO: 39 or an amino acid sequence having at least 80% sequence identity thereto (preferably at least 90%, 95%, 96%, 97%, 98% or 99%) and having the ability to induce protective immunity against *P. vivax* CSP in a human subject.

In some embodiments, one more of the repeat units and/or the N- (when present) or C-terminal and/or HBV S antigen (when present) are independently separated from one another by one more linker amino acids, e.g. 1, 2, 3, 4 or 5 amino acids.

When present, the linker amino acids should not significantly affect (i.e. significantly reduce) the ability of the fusion polypeptide or VLP to elicit protective immunity in a subject (e.g. a human subject). Preferably, no linker amino acids are used.

In some embodiments, the fusion polypeptide additionally comprises a peptide sequence which facilitates the purification of the fusion polypeptide. This peptide sequence is preferably positioned at the C-terminus of the fusion polypeptide. The peptide sequence is preferably a C-tag sequence, more preferably comprising the sequence EPEA (SEQ ID NO: 43).

In some embodiments, the fusion polypeptide additionally comprises one or more further antigens derived from *P. falciparum* and/or *P. vivax*. The further antigen(s) may, for example, be selected from the group consisting of DBP, PvTRAP, PvMSP2, PvMSP4, PvMSP5, PvMSP6, PvMSP7, PvMSP8, PvMSP9, PvAMA1 and RBP.

Percentage amino acid sequence identities and nucleotide sequence identities may be obtained using the BLAST methods of alignment (Altschul et al. (1997), "Gapped BLAST and PSI-BLAST: a new generation of protein database search programs", Nucleic Acids Res. 25:3389-3402; and http://www.ncbi.nlm.nih.gov/BLAST). Preferably the standard or default alignment parameters are used.

Standard protein-protein BLAST (blastp) may be used for finding similar sequences in protein databases. Like other BLAST programs, blastp is designed to find local regions of similarity. When sequence similarity spans the whole sequence, blastp will also report a global alignment, which is the preferred result for protein identification purposes. Preferably the standard or default alignment parameters are used. In some instances, the "low complexity filter" may be taken off.

BLAST protein searches may also be performed with the BLASTX program, score=50, wordlength=3. To obtain gapped alignments for comparison purposes, Gapped BLAST (in BLAST 2.0) can be utilized as described in Altschul et al. (1997) Nucleic Acids Res. 25: 3389. Alternatively, PSI-BLAST (in BLAST 2.0) can be used to perform an iterated search that detects distant relationships between molecules. (See Altschul et al. (1997) supra). When utilizing BLAST, Gapped BLAST, PSI-BLAST, the default parameters of the respective programs may be used.

With regard to nucleotide sequence comparisons, MEGABLAST, discontiguous-megablast, and blastn may be used to accomplish this goal. Preferably the standard or default alignment parameters are used. MEGABLAST is specifically designed to efficiently find long alignments between very similar sequences. Discontiguous MEGABLAST may be used to find nucleotide sequences which are similar, but not identical, to the nucleic acids of the invention.

The BLAST nucleotide algorithm finds similar sequences by breaking the query into short subsequences called words. The program identifies the exact matches to the query words first (word hits). The BLAST program then extends these word hits in multiple steps to generate the final gapped alignments. In some embodiments, the BLAST nucleotide searches can be performed with the BLASTN program, score=100, wordlength=12.

One of the important parameters governing the sensitivity of BLAST searches is the word size. The most important reason that blastn is more sensitive than MEGABLAST is that it uses a shorter default word size (11). Because of this, blastn is better than MEGABLAST at finding alignments to related nucleotide sequences from other organisms. The word size is adjustable in blastn and can be reduced from the default value to a minimum of 7 to increase search sensitivity.

A more sensitive search can be achieved by using the newly-introduced discontiguous megablast page (www.ncbi.nlm.nih.gov/Web/Newsltr/FallWinter02/blast-lab.html). This page uses an algorithm which is similar to that reported by Ma et al. (Bioinformatics. 2002 March;

18(3): 440-5). Rather than requiring exact word matches as seeds for alignment extension, discontiguous megablast uses non-contiguous word within a longer window of template. In coding mode, the third base wobbling is taken into consideration by focusing on finding matches at the first and second codon positions while ignoring the mismatches in the third position. Searching in discontiguous MEGABLAST using the same word size is more sensitive and efficient than standard blastn using the same word size. Parameters unique for discontiguous megablast are:

word size: 11 or 12; template: 16, 18, or 21; template type: coding (0), non-coding (1), or both (2).

In a further embodiment, the invention provides a nucleic acid molecule which codes for a fusion polypeptide of the invention. The nucleic acid molecule may be DNA or RNA, preferably DNA.

The invention also provides a vector or plasmid comprising a nucleic acid molecule of the invention. Preferably, the vector is an expression vector. The vector and/or plasmid may comprise one or more regulatory sequences which are operably linked to the sequence which encodes the fusion polypeptide, e.g. one or more enhancer, promoter and/or transcriptional terminator sequences.

Preferably, the vector is a non-replicating vector, e.g. a non-replicating viral vector.

In some preferred embodiments, the vector is an adenoviral vector or a Modified Vaccinia Ankara (MVA) viral vector.

Preferably, the adenovirus vector is selected from the group consisting of a human adenovirus vector, a simian adenovirus vector, a group B adenovirus vector, a group C adenovirus vector, a group E adenovirus vector, an adenovirus 6 vector, a PanAd3 vector, an adenovirus C3 vector, a ChAdY25 vector, an AdC68 vector and an Ad5 vector.

The invention also provides a host cell comprising a vector or plasmid of the invention.

Preferably, the host cell is a eukaryotic host cell. Examples of eukaryotic host cells include yeast and mammalian cells. In some preferred embodiments, the host cell is a yeast cell (e.g. *Saccharomyces cerevisiae*).

In other preferred embodiments, the yeast is *Pichia pastoris*. *Pichia pastoris* is frequently used as an expression system for the production of proteins. A number of properties make *P. pastoris* suited for this task: *P. pastoris* has a high growth rate and is able to grow on a simple, inexpensive medium; and *P. pastoris* can grow in either shake flasks or a fermenter, which makes it suitable for both small and large scale production.

In other embodiments, the host cell is a methylotrophic yeast, e.g. *Hansenula*, preferably *Hansenula polymorpha*.

The nucleic acid molecule of the invention may be codon-optimised for expression in the host cell, e.g. yeast.

Once expressed in an appropriate system, fusion polypeptides of the invention which comprise a HBV surface antigen are able to assemble spontaneously into lipoprotein structures/particles composed of numerous monomers of said fusion polypeptides.

These particles may be referred to as Virus Like Particles (VLPs). Virus-like particles resemble viruses, but are non-infectious because they do not contain any viral genetic material. The particles may also be described as multimeric lipoprotein particles.

Thus in a further aspect, the invention provides a composition comprising a particle, preferably a VLP, which comprises one or more fusion polypeptides of the invention. The particle is preferably immunogenic.

The invention also provides a composition comprising a multimeric lipoprotein particle which comprises one or more fusion polypeptides of the invention.

In some embodiments of the invention, the particle additionally comprises an amino acid sequence of or derived from Hepatitis B virus surface antigen (in addition to that which is present in the fusion polypeptide). In such embodiments, the ratio of amino acid sequence derived from Hepatitis B virus surface antigen to fusion polypeptide may be from 0.1 to 1.0.

In other embodiments, the particle does not additionally comprise an amino acid sequence derived from Hepatitis B virus surface antigen (other than that which is present in the fusion polypeptide).

In some preferred embodiments, the particle comprises a CSP fragment:HBV S antigen ratio of approximately 1:1.

The invention also provides a VLP (e.g. a VLP comprising HBV surface antigen polypeptides) wherein one or more fusion polypeptides of the invention are covalently attached to the VLP. For example, the fusion polypeptides of the invention may be covalently attached to the VLP by using chemical cross-linkers, reactive unnatural amino acids or SpyTag/SpyCatcher reactions.

In a further embodiment, the invention provides a composition comprising a particle or fusion polypeptide of the invention, optionally together with one or more pharmaceutically-acceptable carriers, excipients or diluents.

The invention particularly provides a composition comprising a particle or fusion polypeptide of the invention, together with a pharmaceutically-acceptable adjuvant.

The invention also provides a vaccine composition comprising a particle or fusion polypeptide of the invention or a vector or plasmid of the invention, preferably a vaccine composition suitable for parenteral administration.

Examples of suitable adjuvants include those which are selected from the group consisting of:
- metal salts such as aluminium hydroxide or aluminium phosphate,
- oil in water emulsions,
- toll like receptors agonist, (such as toll like receptor 2 agonist, toll like receptor 3 agonist, toll like receptor 4 agonist, toll like receptor 7 agonist, toll like receptor 8 agonist and toll like receptor 9 agonist),
- saponins, for example Quil A and its derivatives such as QS7 and/or QS21,
- CpG containing oligonucleotides,
- 3D-MPL,
- (2-deoxy-6-o-[2-deoxy-2-[(R)-3-dodecanoyloxytetra-decanoylamino]-4-o-phosphono-β-D-glucopyranosyl]]-2-[(R)-3-hydroxytetradecanoylamino]-α-D-glucopyranosyldihydrogenphosphate),
- DP (3S, 9R)-3-[(R)-dodecanoyloxytetradecanoylamino]-4-oxo-5-aza-9(R)-[(R)-3-hydroxytetradecanoylamino] decan-1, 10-diol, 1,10-bis(dihydrogenophosphate), and
- MP-Ac DP (3S-, 9R)-3-[(R)-dodecanoyloxytetradecanoylamino]-4-oxo-5-aza-9-[(R)-3-hydroxytetradecanoylamino]decan-I, 10-diol, 1-dihydrogenophosphate 10-(6-aminohexanoate), or combinations thereof.

Preferably, the adjuvant is selected from the group comprising:
- a saponin associated with a metallic salt, such as aluminium hydroxide or aluminium phosphate
- 3D-MPL, QS21 and a CpG oligonucleotide, for example as an oil in water formulation,
- saponin in the form of a liposome, for example further comprise a sterol such as QS21 and sterol, and
- ISCOM.

In some particularly preferred embodiments, the adjuvant comprises a saponin. Saponins are steroid or triterpenoid glycosides, which occur in many plant species.

Saponin-based adjuvants act in part by stimulating the entry of antigen-presenting cells into the injection site and enhancing antigen presentation in the local lymph nodes.

Preferably, the adjuvant comprises saponin, cholesterol and a phospholipid, e.g. ISCOM Matrix-M™ (Isconova, Novavax).

In Matrix-M, purified saponin fractions are mixed with synthetic cholesterol and a phospholipid to form stable particles than can be readily formulated with a variety of vaccine antigens. Matrix-M™ induces both a cell-mediated and an antibody mediated immune response.

In some other preferred embodiments, the adjuvant comprises a squalene-oil-in-water nano-emulsion emulsion, e.g. AddaVax™ (InvivoGen).

Squalene is an oil which is more readily metabolized than the paraffin oil used in Freund's adjuvants. Squalene oil-in-water emulsions are known to elicit both cellular (Th1) and humoral (Th2) immune responses. This class of adjuvants is believed to act through recruitment and activation of APC and stimulation of cytokines and chemokines production by macrophages and granulocytes.

In some other preferred embodiments, the adjuvant comprises two immunostimulants: 3-O-desacyl-4'-monophosphoryl lipid A (MPL) or a variant thereof, and a saponin, preferably QS-21.

In some particularly-preferred embodiments, the adjuvant is a liposome-based adjuvant.

In some particularly preferred embodiments, the adjuvant is AS01. AS01 is a liposome-based vaccine adjuvant system containing two immunostimulants: 3-O-desacyl-4'-monophosphoryl lipid A (MPL) and the saponin QS-21.

The composition may further comprise one or more additional antigens derived from P. falciparum and/or P. vivax in admixture.

The composition may further comprise a surfactant. Examples of suitable surfactants include Tween (such as Tween 20), briji and polyethylene glycol.

Vaccine preparation is generally described in New Trends and Developments in Vaccines, edited by Voller et al., University Park Press, Baltimore, Maryland, U.S.A., 1978. Encapsulation within liposomes is described, for example, by Fullerton, U.S. Pat. No. 4,235,877.

The amount of the particle or fusion polypeptide of the present invention present in each vaccine dose is selected as an amount which induces an immunoprotective response without significant, adverse side effects in typical vaccines. Such amount will vary depending upon which specific immunogen is employed and whether or not the vaccine is adjuvanted. Generally, it is expected that each does will comprise 1-1000 μg of protein, for example 1-200 μg such as 10-100 μg more particularly 10-40 μg. An optimal amount for a particular vaccine can be ascertained by standard studies involving observation of antibody titres and other responses in subjects. Following an initial vaccination, subjects will preferably receive a boost in about 4 weeks, followed by repeated boosts every six months for as long as a risk of infection exists. The immune response to the protein of this invention is enhanced by the use of adjuvant and or an immunostimulant.

The amount of saponin for use in the adjuvants of the present invention may be in the region of 1-1000 μg per dose, generally 1-500 µg per dose, more such as 1-250 µg per dose, and more specifically between 1 to 100 µg per dose (e.g. 10, 20, 30, 40, 50, 60, 70, 80 or 90 µg per dose).

One promising strategy for malaria control consists of targeting antigens expressed on the surface of the sexual stages of the malaria parasites, such as gametocytes, gametes, zygotes or ookinetes. Antibodies against such antigens can inhibit the development of the parasite within the mosquitoes, preventing transmission from the mosquitoes to humans.

Pvs25 and Pvs28 are proteins expressed on the surface of the *Plasmodium vivax* zygotes and ookinetes. Both proteins are essential for the survival of ookinetes in the mosquito midgut, and for the penetration of the midgut epithelium, supporting transformation into oocysts. Pvs25 has received the most attention and has been tested in Phase I clinical trials. Immunisation with this protein has raised antibodies with transmission-blocking activity. Similarly, antibodies raised in mice against Pvs28 have been shown to block the development of oocysts in mosquitoes, blocking transmission of the Sal I strain of *P. vivax*. Transmission-blocking activity was achieved against various natural isolates from Thailand, indicating that variability of the sequences is not an issue for this approach.

In yet a further embodiment, therefore, the invention provides a fusion polypeptide as defined herein which additionally comprises a transmission-blocking component.

Preferably, the transmission-blocking component is a *P. vivax* Pvs25 and/or Pvs28 polypeptide, or a variant or derivative thereof.

Preferably, the Pvs25 amino acid sequence is as given in SEQ ID NO: 45, or a variant or derivative thereof.

Preferably, the Pvs28 amino acid sequence is as given in SEQ ID NO: 46, or a variant or derivative thereof.

In some embodiments, the sequences of PVs25 and 28 are fused, e.g. as in SEQ ID NO: 47, or a variant or derivative thereof.

Preferably, the transmission blocking component is positioned at the N- and/or C-terminal of the Hepatitis B virus surface antigen.

In some embodiments, the fusion polypeptide comprises:
(i) a transmission-blocking component, preferably a *P. vivax* Pvs25 and/or Pvs28 polypeptide, or a variant or derivative thereof;
(ii) an amino acid sequence of or derived from the Hepatitis B virus surface antigen;
(iii) at least 6 repeat units derived from the repeating region of a Type I circumsporozoite protein (CSP) of *Plasmodium vivax*;
(iv) at least 6 repeat units derived from the repeating region of a Type II circumsporozoite protein (CSP) of *Plasmodium vivax*;
(v) at least one repeat unit derived from the repeating region of a circumsporozoite protein (CSP) of *Plasmodium vivax*-like malaria parasite;
(vi) an amino acid sequence of or derived from the C-terminal fragment of CSP of *Plasmodium vivax*; and optionally
(vii) a C-tag sequence,
preferably in the above N- to C-order.

In yet other embodiments, the fusion polypeptide comprises:
(i) at least 6 repeat units derived from the repeating region of a Type I circumsporozoite protein (CSP) of *Plasmodium vivax*;
(ii) at least 6 repeat units derived from the repeating region of a Type II circumsporozoite protein (CSP) of *Plasmodium vivax*;
(iii) at least one repeat unit derived from the repeating region of a circumsporozoite protein (CSP) of *Plasmodium vivax*-like malaria parasite;
(iv) an amino acid sequence of or derived from the C-terminal fragment of CSP of *Plasmodium vivax*;
(v) an amino acid sequence of or derived from the Hepatitis B virus surface antigen;
(vi) a transmission-blocking component, preferably a *P. vivax* Pvs25 and/or Pvs28 polypeptide, or a variant or derivative thereof; and optionally
(vii) a C-tag sequence,
in the above N- to C-order.

In yet further embodiments, the invention provides a particle of the invention, a fusion polypeptide of the invention, a vector or plasmid of the invention or a composition of the invention for use in therapy or for use as a medicament.

In further embodiments, the invention provides a particle of the invention, a fusion polypeptide of the invention, a vector or plasmid of the invention, or a composition of the invention for use in the treatment/prevention of malaria, preferably wherein the malaria is caused by *Plasmodium vivax*.

In further embodiments, the invention provides the use of a particle of the invention, a fusion polypeptide of the invention, a vector or plasmid of the invention, or a composition of the invention in the manufacture of a medicament for use in the treatment or prevention of malaria, preferably wherein the malaria is caused by *Plasmodium vivax*.

The invention also provides a method of treating a patient susceptible to *Plasmodium* infection comprising administering an effective amount of a particle of the invention, a fusion polypeptide of the invention, a vector or plasmid of the invention, or a composition of the invention, particularly as a vaccine, thereby to treat or prevent malaria.

The particle, fusion polypeptide, vector or plasmid, or composition of the invention may also be used in similar uses and methods to produce neutralising antibodies in vivo against antigens on *Plasmodium* parasites, preferably on *Plasmodium vivax*.

The efficacy of the uses and methods to treat/prevent malaria may be tested (e.g. by ELISA) by establishing the presence or absence of neutralising antibodies against CSP in the patient's blood.

The invention also extends to prime-boost regimes. For example, priming and/or boosting may be effected with a *P. vivax* polypeptide (or a nucleic acid encoding such a polypeptide), a fusion protein of the invention or a particle of the invention.

The *P. vivax* polypeptide may, for example, be a TRAP polypeptide (also known as Sporozoite Surface Protein 2 or SSP2) or a variant, fragment or derivative thereof. In all embodiments disclosed herein, the *P. vivax* polypeptide (e.g. TRAP polypeptide) may be replaced by a nucleic acid (e.g. viral vector) encoding such a polypeptide.

The wild-type amino acid sequence of the *P. vivax* polypeptide TRAP polypeptide is given in SEQ ID NO: 40.

The amino acid sequence of a variant of the *P. vivax* TRAP polypeptide is given in SEQ ID NO: 41. In this variant, the first 22 amino acids have been replaced with the tPA amino acid sequence in order to facilitate secretion. Additionally, the C-terminal end has been truncated to facilitate secretion.

Preferably, the *P. vivax* polypeptide is an amino acid sequence derived from the polypeptide given in SEQ ID NO: 40 or 41.

The invention particularly provides a pharmaceutical preparation comprising a particle or fusion polypeptide of the invention together with a *P. vivax* polypeptide, preferably a TRAP polypeptide or variant, derivative or fragment thereof, as a combined preparation in a form suitable for simultaneous, separate or sequential use.

As used herein, the term "an amino acid sequence derived from the polypeptide given in SEQ ID NO: 40 or 41" includes amino acid sequences having at least 80% sequence identity to SEQ ID NO: 40 or 41 (preferably at least 85%, 90%, 95%, 96%, 97%, 98% or 99%) and having the ability to induce an immunogenic response against *P. vivax*.

As used herein, the term "amino acid sequence derived from the polypeptide given in SEQ ID NO: 40 or 41" also includes fragments of SEQ ID NOs: 40 or 41 which are at least 80% of the length of SEQ ID NO: 40 or 41 (preferably at least 90%, 95%, 96%, 97%, 98% or 99%) having the ability to induce an immunogenic response against *P. vivax*.

In some embodiments, the polypeptide, a fusion protein of the invention or a particle of the invention may be replaced by a nucleic acid molecule (preferably DNA) coding for the polypeptide, fusion protein or particle. The nucleic acid molecule may, for example, be a viral vector (e.g. adenoviral vector or MVA).

Other prime boost regimes are described below. For example:

priming may be with an antigen (such as an adjuvanted antigen) comprising at least one Type I repeat unit from the CS protein of *P. vivax* and at least one Type II repeat unit from the CS protein of *P. vivax*; and boosting may be with a viral vector encoding the same/corresponding antigen, priming may be with an antigen (such as an adjuvanted antigen) comprising at least one repeat unit or epitope from *P. vivax* and at least one repeat unit or epitope from the CS protein of *P. falciparum*; and boosting may be with a viral protein encoding the same/corresponding antigen, priming may be with a viral vector encoding an antigen comprising at least one Type I repeat unit from the CS protein of *P. vivax* and at least one Type II repeat unit from the CS protein of *P. vivax* or comprising at least one repeat unit or epitope from *P. vivax* and at least one repeat unit or epitope from the CS protein of *P. falciparum*; and boosting with the same/corresponding adjuvanted antigen in the form of a protein and/or immunogenic particle.

Antigen in these contexts includes fusion protein and/or immunogenic particles of the invention. In these prime boost regimes, antigen will usually be adjuvanted.

In yet further embodiments, the invention provides a process for the production of a particle or fusion polypeptide of the invention, which process comprises expressing a nucleic acid molecule coding for said particle or polypeptide in a suitable host and recovering the product.

Preferably, the host is a yeast. More preferably, the host cell is *Pichia pastoris* or *Saccharomyces*.

BRIEF DESCRIPTION OF THE FIGURES

FIGS. 1A-1C: Cellular immune responses following immunization with viral-vectored vaccines (vv; ChAd63 or MVA) expressing different versions of PvCSP. (a) Schematic representation of the CSP sequences expressed by ChAd63 and MVA vectors. NC: the amino (N)- and carboxy-terminal (C) sequences without central repeat regions (CR); a fragment containing the repeat sequences of the VK210 allele (N21 OCR) or the VK247 allele (N247CR) or a chimeric fragment with both repeat sequences (N210/247CR), all contain an insertion region (IR); (b) Groups of mice of four strains (C57B16, C3H/HE, BALB/c, CD1, n=6) were immunized with different vv using an Ad prime- and MVA boost regimen at an interval of 8 weeks and cellular responses were assessed by ex vivo IFN-γ ELISpot on week two after the MVA boost. (c) Antigen-specific T-cell responses as measured by ex-vivo IFN-γ ELISPOT assay. Splenocytes were stimulated with four sub-pools of peptides overlapping the N-, 210-, 247-, and C-terminal region of the PvCSP protein.

FIG. 4A. Schematic representation describing the generation of PbANKA-PvCSP(r)$_{PbCSP}$ (2196cl1 and 2199cl1) chimeric lines; where the *P. berghei* csp (Pbcsp) gene coding sequence (CDS) is replaced GIMO deletion-construct (construct 1; pL1929) is used to replace the Pbcsp CDS with the positive/negative selectable maker (SM; hdhfr::yfcu) cassette, resulting in the generation of the Pbcsp GIMO line (PbANKA-PbCSP GIMO; 2151cl1) after positive selection with pyrimethamine. Construct 1 targets the Pbcsp gene by double cross-over homologous recombination. Step 2: The GIMO insertion-construct (construct 2; pL1942 or pL1943) is used to replace the SM in the GIMO line with Pvcsp VK-210 or VK-247 CDS, respectively, after negative selection using 5-fluorocytosine (5-FC), resulting in the two chimeric lines PbANKA-PvCSP VK210(r)$_{PbCSP}$ and PbANKA-PvCSP VK247(r)$_{PbCSP}$ (2196cl1 and 2199cl1), respectively. Construct 2 integrates by double cross-over homologous recombination using the same targeting regions (TRs) employed in construct 1, resulting in the introduction of Pvcsp gene under the control of the Pbcsp gene promoter and transcriptional terminator sequences and removal of the SM.

FIG. 4B. Schematic representation of the reporter PbANKA parasite line PbGFP-Luc$_{eefla}$ (676m1cl1) which used to generate the replacement gene [RG] chimeric parasites. It expresses a fusion protein of GFP and firefly luciferase (LUC-IAV) under the constitutive Pbeef1a promoter and is selectable marker (SM) free. The reporter-cassette is integrated into the neutral 230p locus in chromosome-3.

FIG. 4C. Genotype analysis of Replacement Gene [RG] chimeric parasites and their intermediate GIMO mother-line knock out chimeric parasites using Southern analysis of chromosomes (chrs) separated by pulsed-field gel electrophoresis (PFGE)

Left panel: PbANKA-ΔCSP GIMO: 2151 cl1. The correct integration of the SM in the right locus in Chr-4 and replacing the endogenous PbCSP gene (PBANKA_040320) was confirmed by using the 3'UTR Pbdhfr/ts probe which hybridized Chr-3 because of the presence of the GFP-Luc cassette with 3'UTR Pbdhfr/ts, hybridized Chr-4 which confirms the corrected integration of the SM cassette into the right locus and replacing PbCSP gene with the SM and also hybridizes to the endogenous Pbdhfr/ts on Chr. 7. The correct integration of the SM; also confirmed by using a mixture of two probes hdhfr/chr.5.

Right panel: D. PbANKA-PVCSP(r)$_{PbCSP}$: 2196cl1 and 2199cl1. the correct integration of the PvCSP expression construct into the GIMO locus was confirm by showing the removal of the hdhfr::yfcu SM cassette in the cloned chimeric parasite line (2196cl1 and 2199cl1). The southern blot is hybridized with a mixture of two probes: one recognizing hdhfr and a control probe recognizing chr-5. As an additional control (ctrl), parasite line 2117cl1 is used with the hdhfr::yfcu SM integrated into chr-3.

Figure 4A:
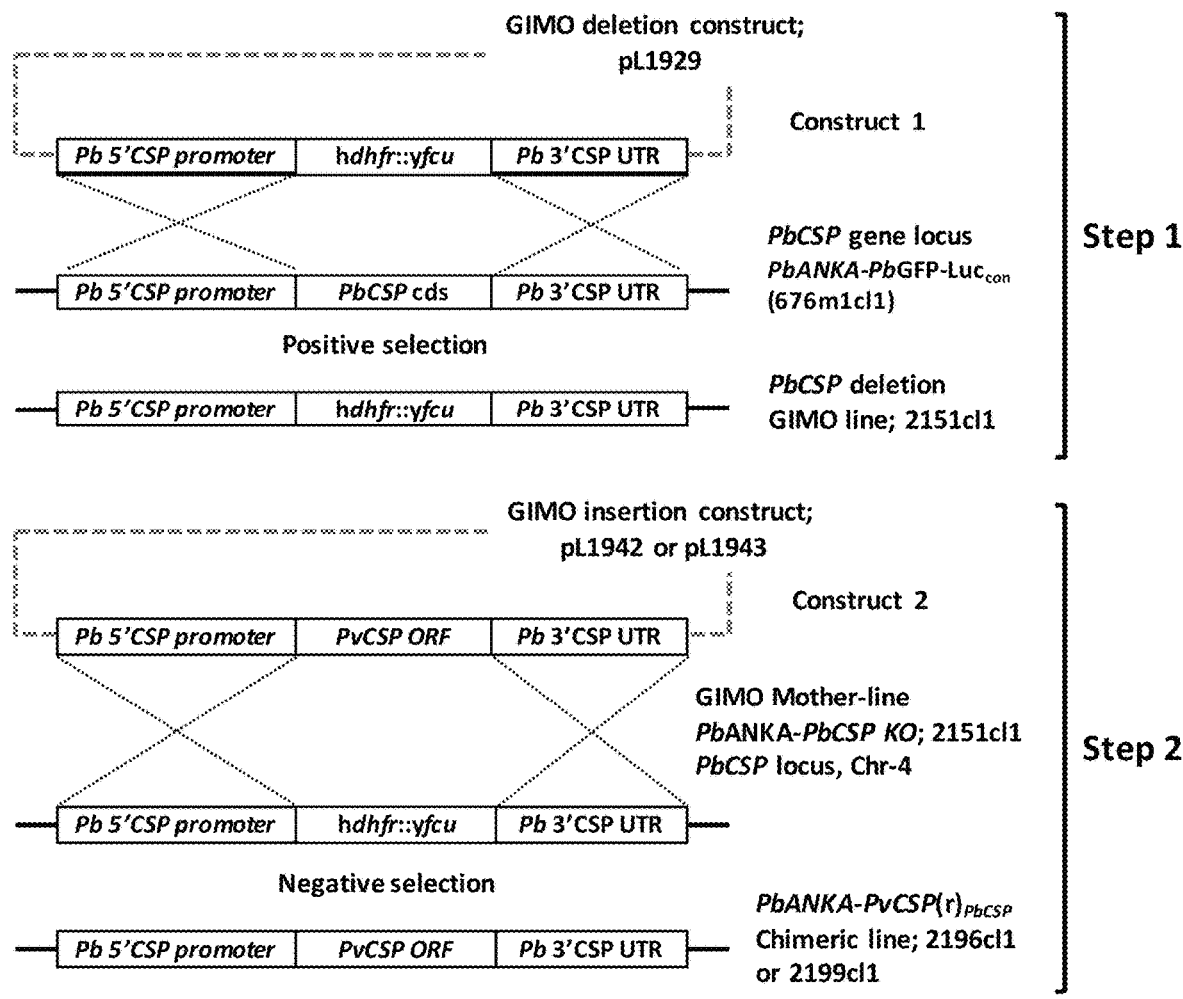
FIGS. 4A-4D: Cloning strategy for the development of two *P. berghei* parasite lines expressing *P. vivax* CSP VK210 or VK247.
Figure 4B:
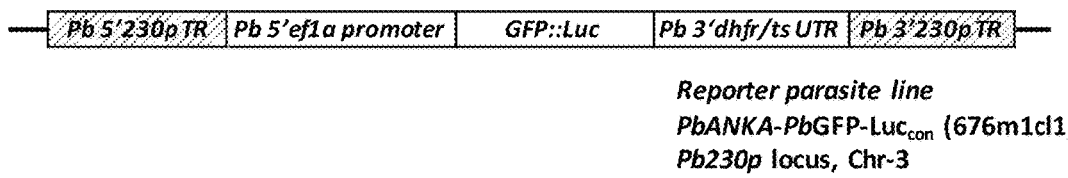
Figure 4C:
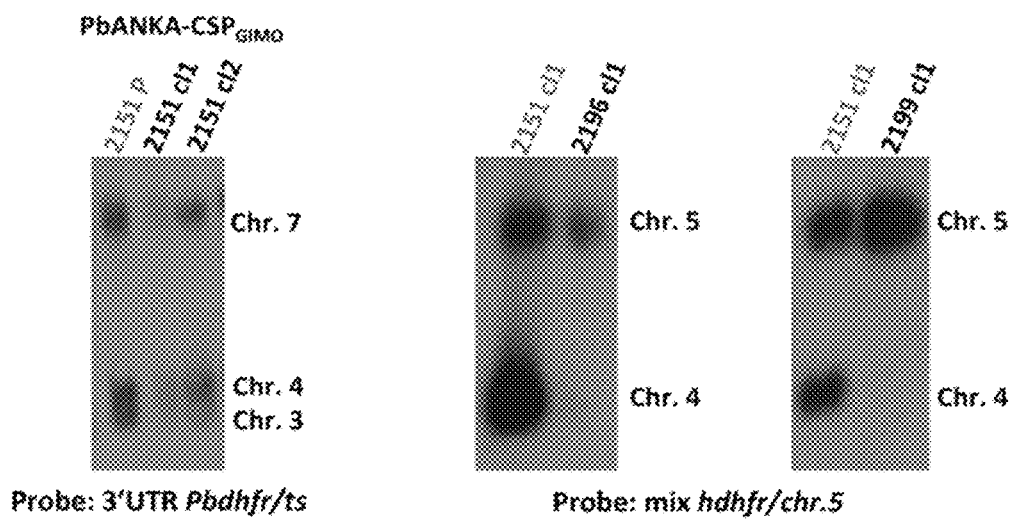
Figure 4D:
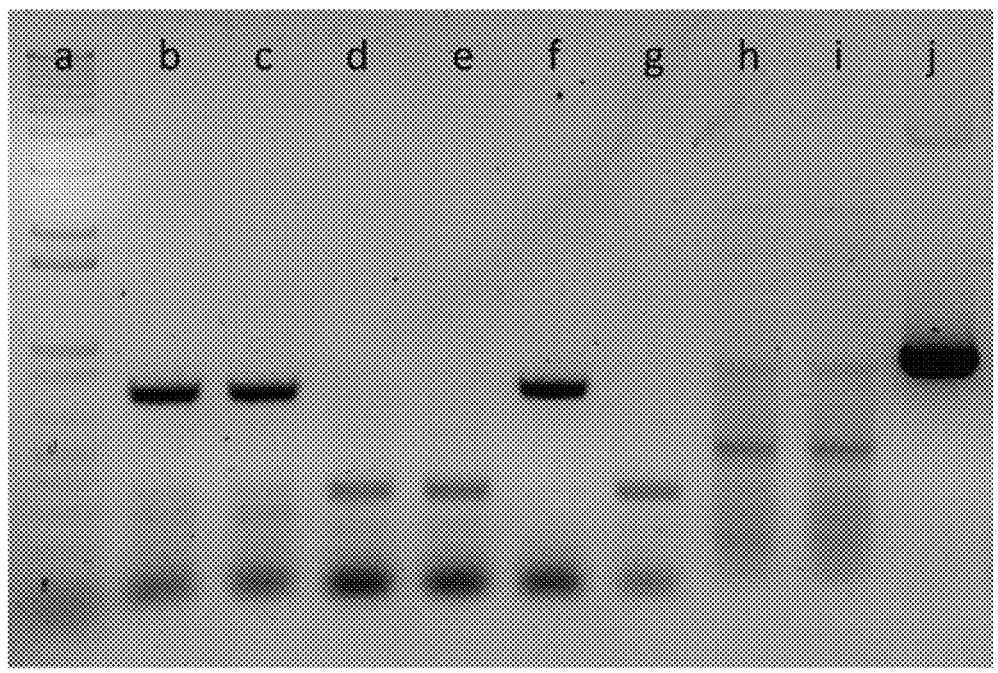

FIG. 4D. Genotype analysis by diagnostic PCR analysis of chimeric parasite lines confirming correct integration of both PvCSP VK210 and VK247 antigen expression cassettes. Correct integration in both lines is shown by the absence of the hdhfr::yfcu selectable marker (SM), the presence of the PvCSP gene CDS and the correct integration of the construct into the genome both at the 5' and 3'regions (5'int and 3'int). Primers sequences used are shown in Table S1, while the expected PCR product sizes and the primer numbers are listed in the table below the Agarose gel images.

Figure 4E:
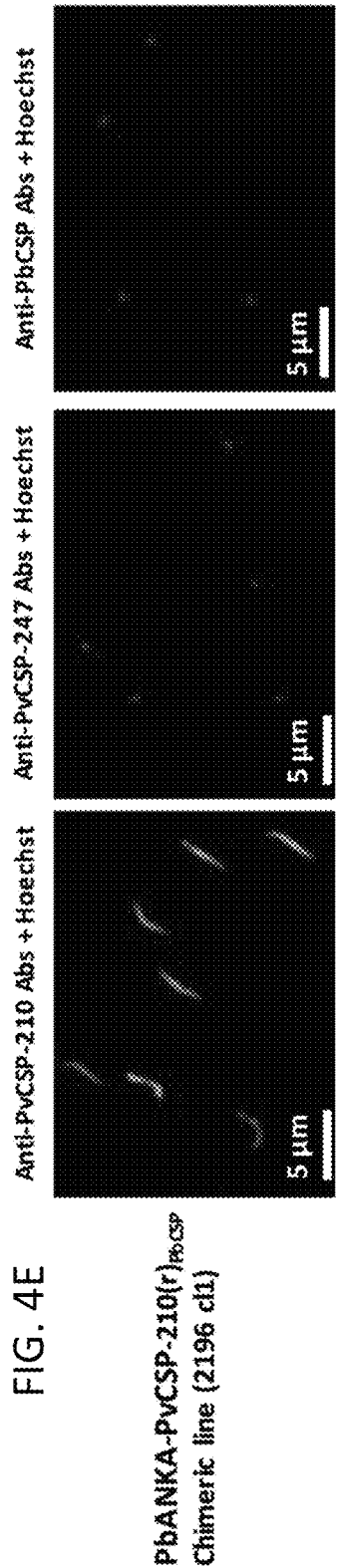
Figure 4F:
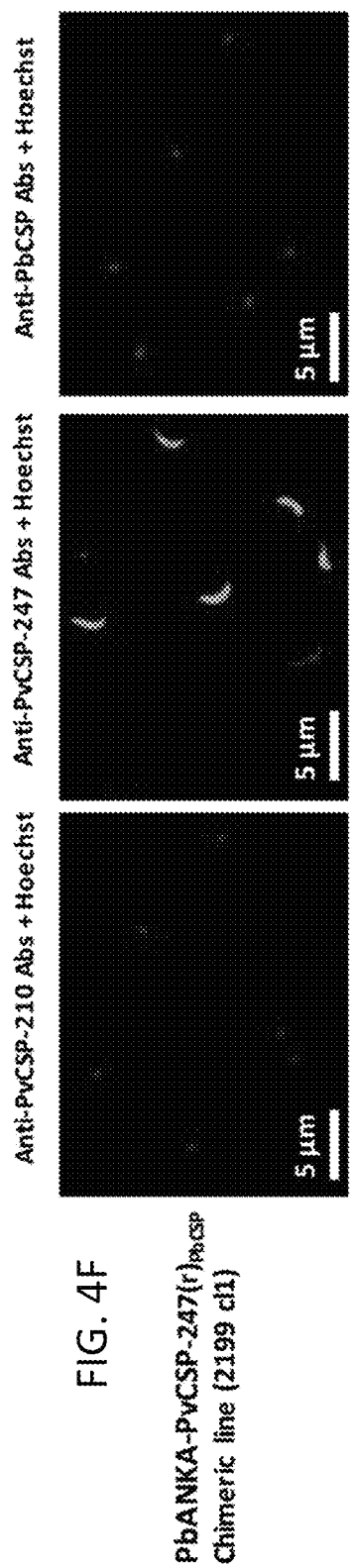
Figure 4G:
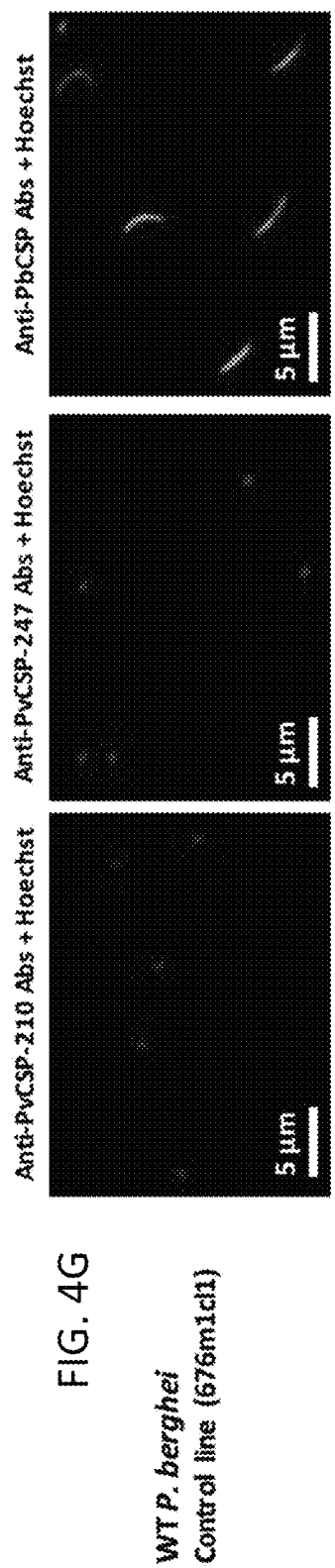

FIGS. 4E-4G. Immunofluorescence assay (IFA) to assess expression of PvCSP on the surface of the transgenic sporozoites and in vivo imaging. Sporozoites from mosquito salivary-glands were stained with anti-PvCSP-210 (MR4) diluted 200 times, anti-PvCSP-247 (MR4) diluted 200 times, and anti-PbCSP (3D11) diluted 1000 times. Alexa Fluor® 488-labelled anti-mouse IgG and Hoechst-33342 were also included for the assay. (E) Transgenic parasite line 2196cl1 expressing the PvCSP VK210; (F) Transgenic parasite line 2199cl1 expressing the PvCSP VK247; (G) Wild type *P. berghei* parasite line 676m1cl1 showing expression of PbCSP.

FIGS. 5A-5D. Fitness and phenotype analyses of two transgenic *P. berghei* lines expressing *P. vivax* CSP VK210 or VK247. Mean numbers of oocysts (A) and salivary gland sporozoites (B) in *A. stephensi* mosquitos at day 10 and 21, respectively (3 independent experiments; 40 mosquitoes per experiment; error bars show standard deviation). (C) Blood-stage parasitaemia (mean±SEM) in mice after intravenous (i.v.) injection of 2000 sporozoites per mouse. (D) The Kaplan-Meier curves illustrate the time to reach 1% parasitaemia (Tto1) in 6 CD1 mice after i.v. injection with 2000 transgenic or wild type sporozoites. Survival analysis was made using a Kaplan-Meier Log-rank (Mantel-Cox) test. n.s.: not significant.

FIGS. 6A-6F. Viral-vectored vaccine (vv) efficacy against a challenge with transgenic *P. berghei* sporozoites expressing *P. vivax* CSP VK210 or VK247.

Figure 1A:
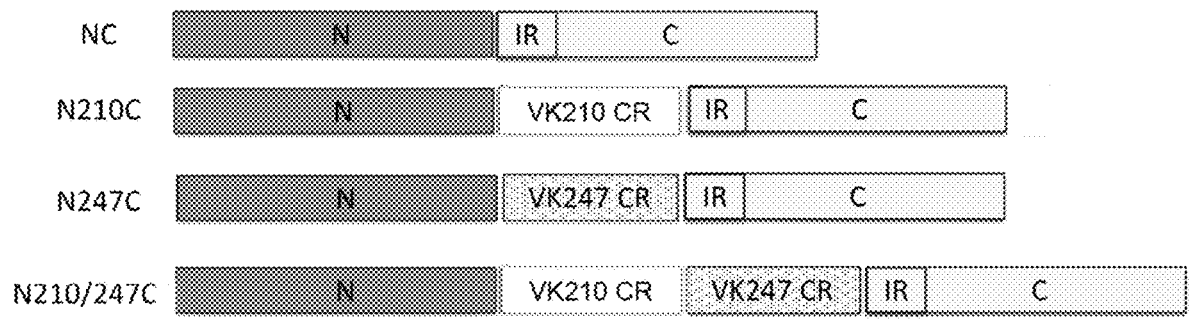

Groups of mice (n=6) were immunized with vv expressing PvCSP (N210/N247C, N210C, N247C, NC; see FIG. 1) using an Ad prime and MVA-boost regimen. A vv expressing *P. berghei* CSP was used as control. Two (A-D) or 12 € weeks after the boost, mice were challenged by intravenous injection of 2,000 transgenic sporozoites expressing *P. vivax* CSP VK210 or VK247. The Kaplan-Meier curves illustrate the time to 1% parasitaemia (A-F). As a control PbCSP or N210/N247C immunized mice were challenged with wild type *P. berghei* sporozoites (F). Statistical analysis was performed using the Kaplan-Meier survival curves and P values were calculated using a Kaplan-Meier Log-rank (Mantel-Cox) test. Data was obtained from two individual experiments.

FIGS. 7A-7I. Development, immunogenicity and efficacy of the Rv21 virus-like particle (VLP) presenting the chimeric PvCSPVK210/247 antigen fused to the Hepatitis B Surface antigen The chimeric construct was expressed as a VLP in *P. pastoris* (A) Western blot to confirm expression of the VK210, VK247 and HepB surface antigen (S Ag) (B) Analysis of protein presence and purity using silver staining after affinity purification (left panels) and visualization of VLPs by transmission electron microscopy (TEM, right panels). (C) Analysis of protein purity using silver staining after a second round of purification using size exclusion chromatography and visualization of VLPs from the same purification by TEM (right panel). (D) Protective efficacy of Rv21 in CD-1 mice immunized with a low dose of 0.5 μg of VLP alone or mixed with Matrix M adjuvant and challenged with transgenic sporozoites expressing *P. vivax* CSP VK210 or VK247. Kaplan-Meier curves indicate the time to reach 1% parasitemia. (E) Anti-PvCSP antibody responses in the same groups of mice on week 2 after prime (day 14) or boost (day 28) and prior to challenge. (F) Protective efficacy in C57Bl/6 mice immunized with either a low dose of 0.5 μg (left) or a high dose of 5 μg (right) of Rv21 in presence or absence of Matrix M adjuvant (Adj). Mice were challenged with transgenic sporozoites expressing *P. vivax* CSP VK210 or VK247. The Kaplan-Meier curves illustrate the time to 1% parasitaemia. (G) Kinetic of the antibody responses in presence or absence of the Matrix M adjuvant (left) and evidence of high avidity of anti-PvCSP on the long-term with the use of Matrix M adjuvant. (H) Association (left) and correlation (right) of antibody titers with protective efficacy. (I) Association of titers of IgG2a with protection.

Figure 8A:
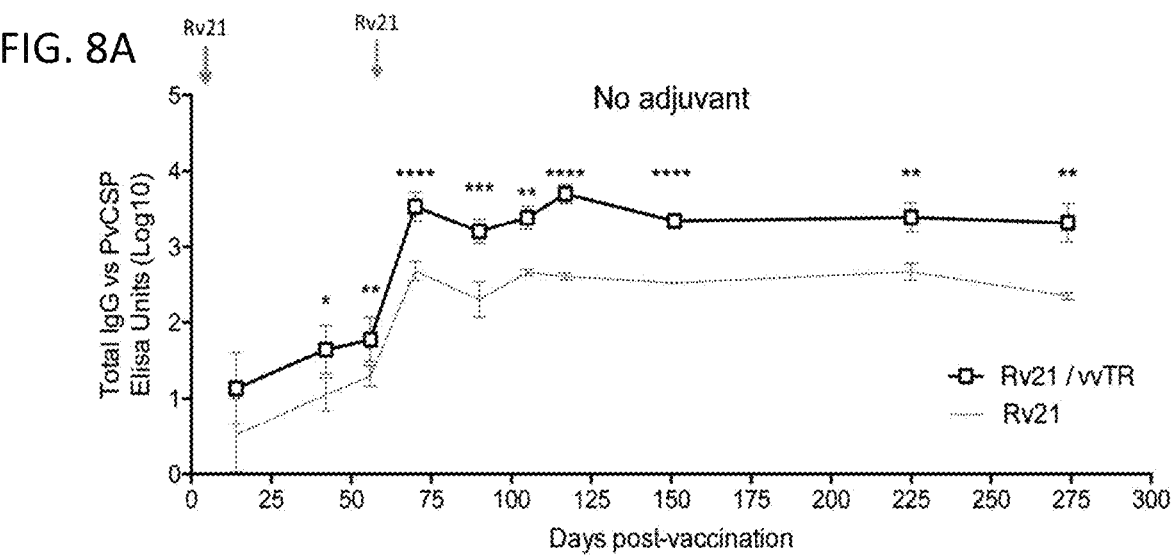
Figure 8B:
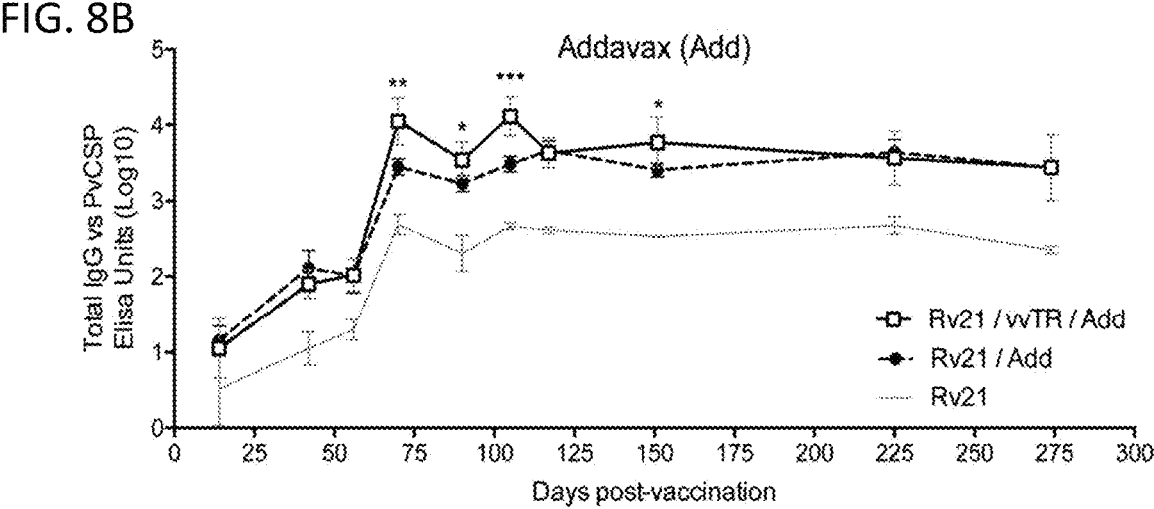
Figure 8C:
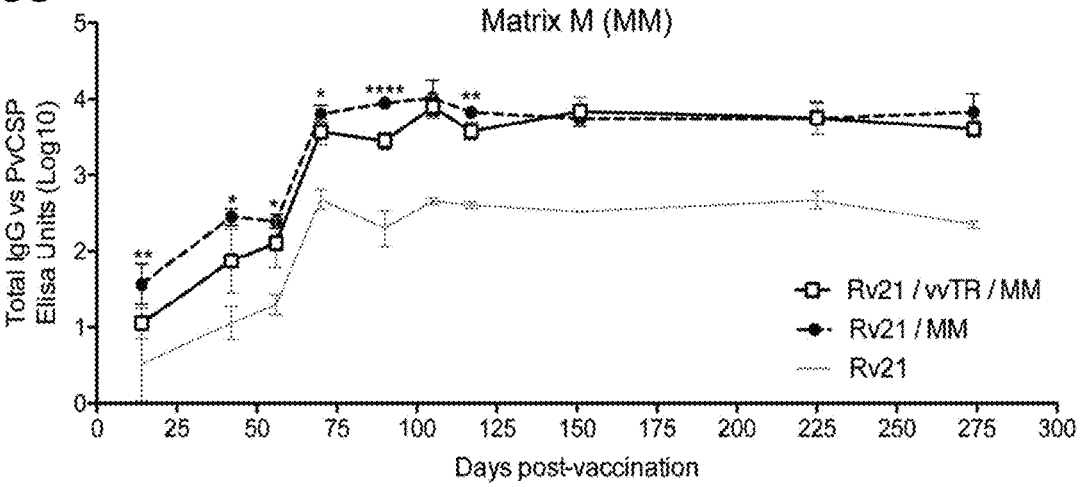

FIGS. 8A-8C: The effect of adjuvants and a combination of viral vectors on Rv21 anti-*vivax* CSP immunogenicity.

Figure 9A:
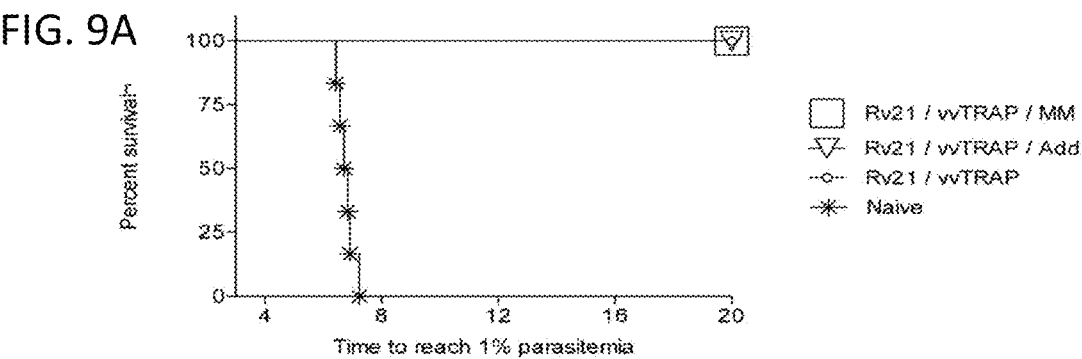
Figure 9B:
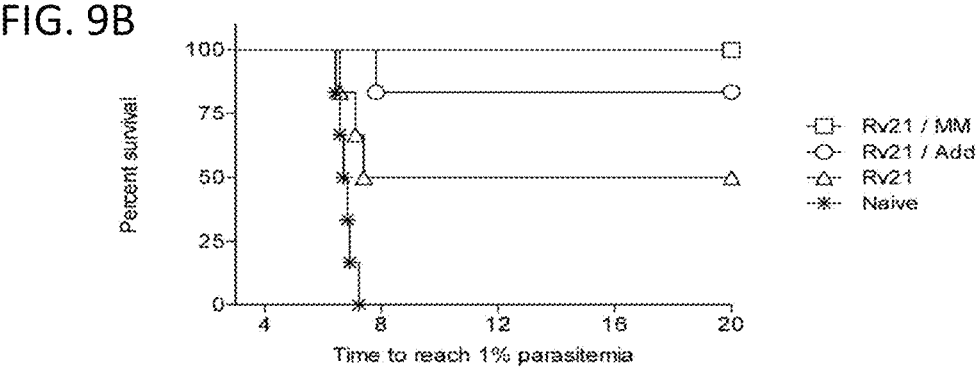
Figure 9C:
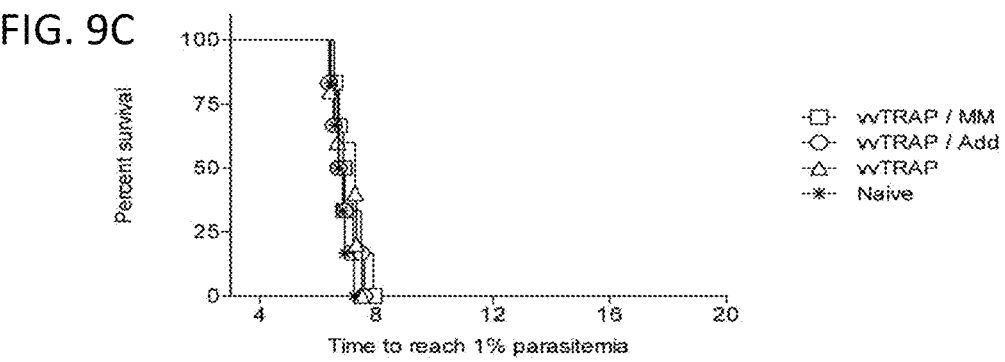
Figure 9D:
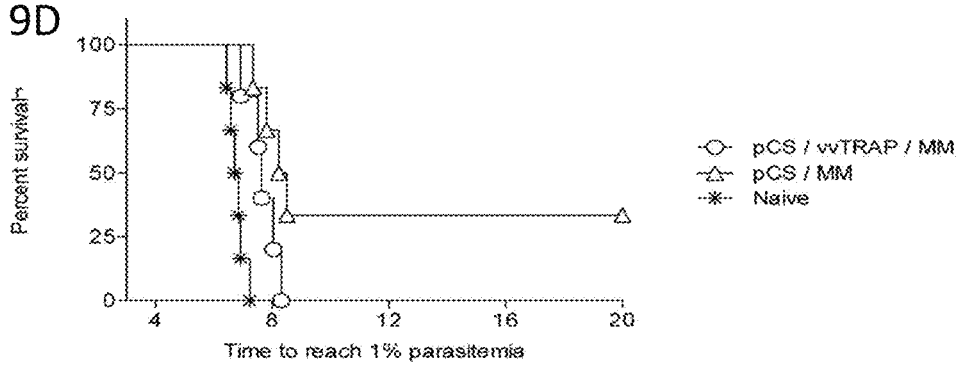

FIGS. 9A-9D: The effect of adjuvants and a combination of viral vectors on Rv21 protective efficacy against a sporozoite challenge. FIG. 9A is a graph showing the effect of the combination of Rv21+vvTRAP+Adjuvants Matrix M (MM) or Addavax (Add) against a sporozoite challenge. FIG. 9B is a graph showing the effect of a suboptimal dose of Rv21, alone or in combination with adjuvants Addavax (Add) or Matrix M (MM), against a sporozoite challenge. FIG. 9C is a graph showing the effect of a prime/boost with adenovirus-TRAP and MVA-TRAP (vvTRAP) from *vivax*, with or without adjuvants, against a sporozoite challenge. FIG. 9D is a graph showing the effect of *vivax* CSP administered as a protein (pCS) instead of a VLP composition (Rv21) with and without MM adjuvant against a sporozoite challenge.

Figure 10:
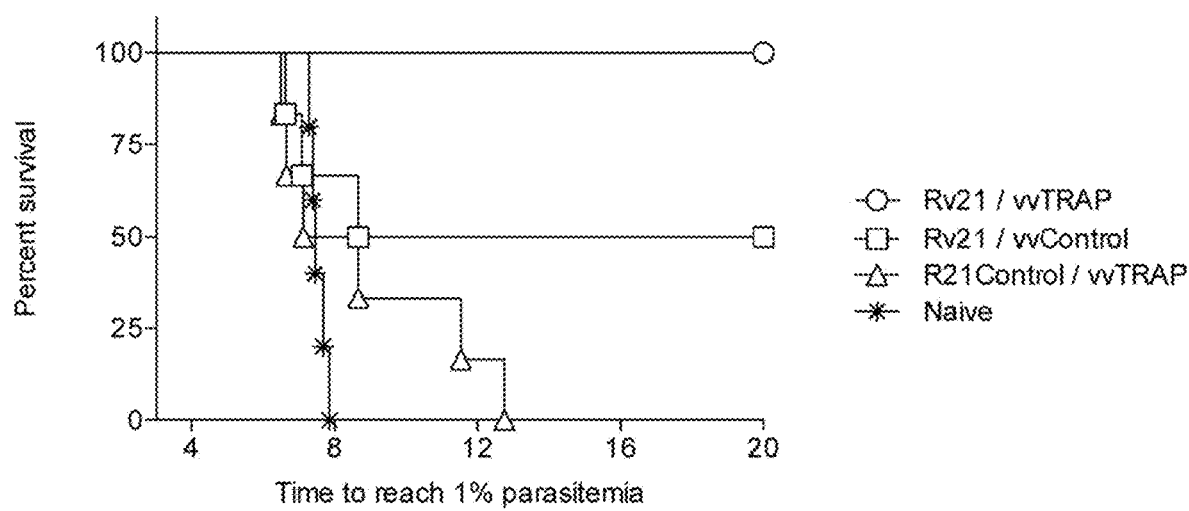

FIG. 10: Survival data of BALB/c mice after priming with Rv21+AdTRAP and then boosting with Rv21+MVAPvTRAP.

Figure 11A:
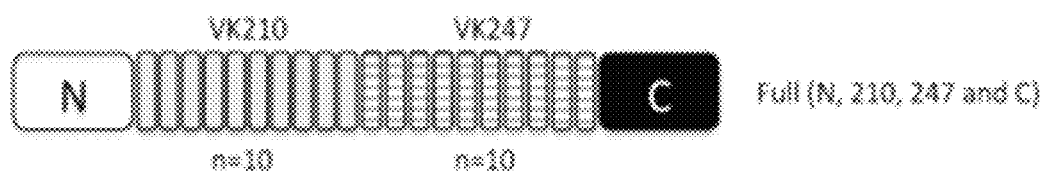
Figure 11B:
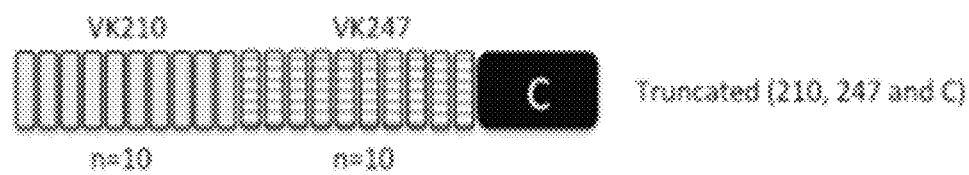
Figure 11C:
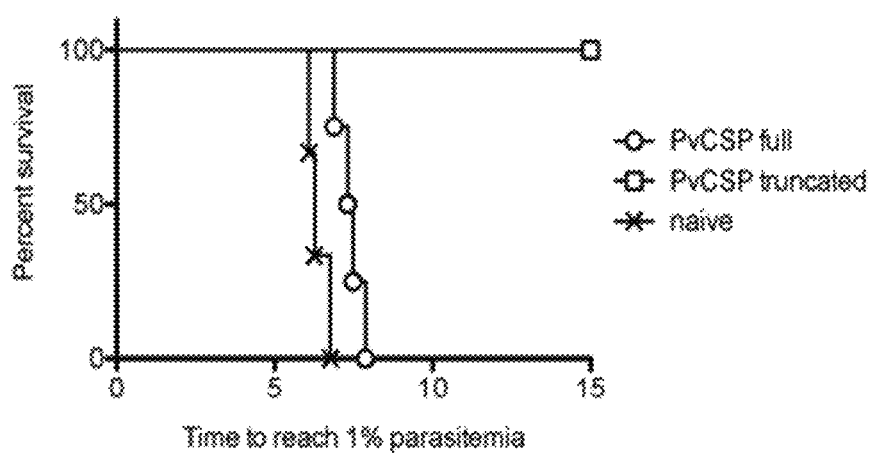

FIGS. 11A-11C: Effect of the presence of the N-terminal region of P. vivax CSP on the protective efficacy against a malaria sporozoite challenge.

FIGS. 12A-12E: Characterisation of Rv21 by Western blot and ELISA.

EXAMPLES

The present invention is further illustrated by the following Examples, in which parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

The disclosure of each reference set forth herein is incorporated herein by reference in its entirety.

Example 1: Materials and Methods

Materials and Methods

Animals

Female inbred BALB/c (H-$2^d$), C57BL/6 (H-$2^b$) and outbred CD1 (ICR) mice were used for the assessment of immunogenicity and protection after challenge. Tuck-ordinary (TO) outbred mice were used for parasite production and transmission. Mice were purchased from Harlan (UK). Transgenic parasites were developed in Leiden University Medical Centre (LUMC) using 6-week old Swiss mice (Charles River).

Parasite Production

Wild type and transgenic parasites used to challenge mice were produced at the insectary of the Jenner Institute. Female Anopheles stephensi mosquitoes were fed on infected TO mice. Briefly, exflagellation was first confirmed and mosquitoes were exposed to anaesthetized infected mice for 10 minutes. Mosquitoes were then maintained for 21 days in a humidified incubator at a temperature of 19-21° C. on a 12 hour day-night cycle and fed with a fructose/PABA solution.

Parasites

The wild type (WT) reference line cl15cy1 of P. berghei ANKA [48] and the reporter PbANKA parasite line PbGFP-Luc$_{con}$ (676m1cl1). PbGFP-Luc$_{con}$ parasite expresses a fusion protein of GFP (mutant3) and firefly luciferase (LUC-IAV) under the constitutive eef1a promoter and is SM free [48]. The reporter-cassette is integrated into the neutral 230p locus (PBANKA_030600). For details of PbGFP-Luc$_{con}$, see RMgmDB entry #29 (www.pberghei.eu/index.php?rmgm=29).

Laboratory Animals and Ethics Statement

For the generation of the chimeric parasites Swiss mice (OF1 ico, Construct 242; 6 weeks old; 25-26 g; Charles River) were used. All animal experiments performed at the LUMC were approved by the Animal Experiments Committee of the Leiden University Medical Center (DEC 12042). The Dutch Experiments on Animals Act was established under European guidelines (EU directive no. 86/609/EEC regarding the Protection of Animals used for Experimental and Other Scientific Purposes).

Generation of DNA Constructs and Genotyping of the Chimeric Parasites

To generate the chimeric parasites where the P. berghei csp gene (PBANKA_040320) coding sequence (CDS) has been replaced by the CDS of P. vivax csp (PVX_119355), we used a 2-step GIMO transfection protocol [31, 49]. In the first step, we deleted the P. berghei csp CDS and replaced it with the positive-negative selectable marker, to create a P. berghei csp deletion GIMO line (PbANKA-CS GIMO). In order to do this, we generated pL1929 construct that is based on the standard GIMO DNA construct pL0034 [49]. This construct contains the positive-negative (hdhfr::yfcu) selection marker (SM) cassette, and was used to insert both the Pbcsp 5' and 3' gene targeting regions (TR), encompassing the full length promoter and transcription terminators sequences respectively. The linear pL1929 DNA construct was introduced into PbGFP-Luc$_{con}$ parasites using standard methods transfection [48]. Transfected parasites were selected in mice by applying positive selection by providing pyrimethamine in the drinking water [48]. Transfected parasites were cloned by limiting dilution [50], resulting in the PbANKA-CS GIMO line (2151cl1). Correct deletion of the P. berghei csp CDS was confirmed by diagnostic PCR-analysis on gDNA and Southern analysis of pulsed field gel (PFG) separated chromosomes as described [48]. Primers used for PCR genotyping are listed in Table S1 below.

TABLE S1

| Primer name | Primer sequence[1] | Expected PCR product | PCR size (bp) |
|---|---|---|---|
| PvCSP-trans (F6) PvCSP-trans (R5) | TGACATGCATA TGTGTTGGTTG (SEQ ID NO: 48)/ GCTGATTGTC CAACATGTGC (SEQ ID NO: 49) | PvCSP 5' int. | 744 |
| 1054 1055 | CCAAAGGAACTT AAACGAGCTATG (SEQ ID NO: 50)/ CTTATACCAGAA CCACATGTTACG (SEQ ID NO: 51) | PbCSP | 744 |
| 7393 7394 | ATCGACTAGTAA AGCCTCGCTACG (SEQ ID NO: 52)/ GTGAGTCAGATG GACTTTCTGGTAG (SEQ ID NO: 53) | PbTRAP Control | 1052 |

[1]The primer sequences (i.e. Forward/Reverse) surrounding the regulatory region are shown with the restriction site used (bold and underlined) to introduce the region into the transfection construct.

In the second step, we replaced the positive-negative SM in the PbANKA-CS GIMO genome with the CDS of either P. vivax VK210 or VK247 csp by GIMO transfection to create the two P. berghei transgenic CSP replacement lines. This was achieved by modifying the construct used in the first step (pL1929); specifically, the hdfhr::yfcu SM cassette was removed and replaced with *P. vivax* csp CDS sequence. The *P. vivax* csp CDS was ordered from GeneArt (Regensburg, Germany) (i.e. VK210) or cDNA (VK247) Both the *P. vivax* VK210 and VK247 CSP constructs (pL1942 and pL1943, respectively) were sequenced to ensure there were no mutations in the *P. vivax* csp CDS. These constructs were linearized using SacI and PacI restriction enzymes outside of the 5' and 3' TRs before transfection. These constructs were used to transfect parasites of the PbANKA-CS GIMO line (2151cl1) using standard methods of GIMO-transfection [30]. Transfected parasites were selected in mice by applying negative selection by providing 5-fluorocytosine (5-FC) in the drinking water of mice [51]. Negative selection results in selection of chimeric parasites where the hdhfr::yfcu SM in the csp locus of PbANKA-CS GIMO line is replaced by the CDS of *P. vivax* CSP Selected chimeric parasites were cloned by the method of limiting dilution [50]. Correct integration of the constructs into the genome of chimeric parasites was analyzed by diagnostic PCR-analysis on gDNA and Southern analysis of pulsed field gel (PFG) separated chromosomes as described [48]. Primers used for PCR genotyping are listed in Table S1. This method creates chimeric 'gene replacement' *P. berghei* parasites that do not contain *P. berghei* csp gene CDS but express either *P. vivax* VK210 (PbANKA-PvCS VK210(r)$_{PbCS}$; 2196cl1) or VK247 csp (PbANKA-PvCS VK247(r)$_{PbCS}$; 2199cl1) under the control of the *P. berghei* csp regulatory sequences.

Phenotyping of Reporter and Chimeric Parasites

Growth of blood stages of the reporter and chimeric *P. berghei* parasites was determined during the cloning period as described [30, 48]. Feeding of *A. stephensi* mosquitoes, determination of oocyst production, sporozoite collection were performed as described [30]. Expression of PvCSP-VK210 and PvCSP-VK247 antigens in sporozoites of the chimeric parasites was analysed by immunofluorescence-staining assay (IFA), using anti-*P. vivax* antigen monoclonal antibodies (anti-PvCSP-VK210 (MR4) or anti-PvCSP-247 (MR4) antibodies; diluted 200 times) or anti-PbCSP 3D11 antibodies as a control; diluted 1000 times. Purified sporozoites were fixed with 4% paraformaldehyde in PBS for 20 min on ice, then washed three times with PBS and blocked with 20 ul 10% FCS+1% BSA in PBS for 30 min at room temperature. The excess blocking medium was removed, followed by the addition of 20-25 uL primary monoclonal antibody in 10% FCS+1% BSA in PBS (blocking medium) for 1-2 hours at room temperature or overnight at 4° C. After incubation the primary antibody was removed and the slides washed three times with PBS, followed by the staining with the secondary antibody (Alexa Fluor® 488 Goat Anti-Mouse IgG from life technologies, Cat #A-11001) diluted 800 times in 10% FCS+1% BSA in PBS (blocking medium) for 1 hour at room temperature. After washing three times with PBS, nuclei were stained with 2% Hoechst-33342 (Cell Signaling Technology #4082S) in PBS for 10 minutes at room temperature, washed twice with PBS and left to air-dry, this followed by adding Fluorescence Mounting Medium (Dako, code S3023) before complete dry out. Cover slips were mounted onto the slides, and the slides were sealed with nail polish and left to dry overnight in dark. The parasites in both blue and green channels were analyzed using a DMI-300B Leica fluorescence microscope and images processed using ImageJ software.

Antibody recognition to native, wild type *P. vivax* isolates from Mexico was assessed by IFA using a technique described earlier [52]. Briefly, sporozoites were produced by infection of laboratory-reared *An. albimanus* mosquitoes that fed on blood from patients infected with *P. vivax*. Mosquitoes were maintained for 15-18 days and sporozoites were collected by dissection of the salivary glands and deposited in multiwell IFAT slides at a concentration of 2,000 sporozoites/well. Slides were kept frozen at −70° C. until used. The assay was performed using sera from C57Bl/6 and CD-1 mice, which was incubated with three different batches each of sporozoites, yielding similar results between both strains. Air-dried sporozoites were also incubated with anti-VK210 or anti-VK247 monoclonal antibodies as positive controls [29]. Slides were analyzed using a confocal microscope and titers were calculated using the highest dilution that gave positive fluorescence.

Efficacy Studies: Determination of Liver Parasite Liver Load by Real Time Imaging and Determination Prepatent Period (after Challenge of Immunized Mice with Chimeric Sporozoites)

To determine the efficacy of the liver-stage vaccines, chimeric *P. berghei* infected *A. stephensi* mosquitoes were dissected 21 days post-feed and salivary gland sporozoites resuspended in RPMI-1640 media (Sigma Aldrich). 2000 sporozoites were injected i.v. into the tail vain per mouse, into both vaccinated and naïve controls.

In Vivo Imaging Using the IVIS System

All the transgenic parasite lines were generated to express the fusion protein GFP-Luciferase under the control of the constitutive eef1a promoter. The gfp-luc expression cassette is stably integrated into the Pb230p locus without introduction of a drug-selectable marker {Spaccapelo, 2010 #257; Janse, 2006 #181}. In vivo imaging of mice was performed using the IVIS 200 imaging system to determined parasite loads in livers of infected mice 44 hours post-infection {Ploemen, 2009 #258}. Mice were firstly shaved over the area of the liver, then anaesthetized and subcutaneously (s.c.) injected with 50 μl of 50 mg/ml D-luciferin substrate. Eight minutes after the injection of luciferin, mice were imaged for two minutes. Quantification of the bioluminescence signal was performed using the Living Image 4.2 image analysis software program. The readings were expressed as the total flux of photons emitted per second of exposure time.

Transgenic Parasite Fitness

Parasite fitness studies indicated similar infectivity, growth rates, gametocyte production and production of oocysts and sporozoites for the chimeric parasites expressing the *P. vivax* CSP genes compared to those of the WT *P. berghei* line. The blood stage growth and prepatent time to reach 1% parasitaemia in naïve mice for chimeric parasites were identical to the WT *P. berghei* line.

*P. vivax* CSP DNA Sequences

Four versions of ChAd63 and four of MVA were designed and produced to express various versions of the *P. vivax* CSP protein. One consisted of only the N- and C-terminal regions (NC); a second viral vector expressed VK210 repeats inserted in between the N- and C-terminal sequences (N210C). A third vector expressed VK247 inserted between the N- and C-terminal sequences (N247C) and a final design consisted on a chimeric VK210/247 flanked by similar N- and C-terminal repeats (sequences detailed below).

DNA transgenes were synthesized by GeneArt (Regensburg, Germany) and constructs were previously modified to improve antigen expression within the hosts cells, modifications included codon optimization for mammalian use and replacement of the endogenous PvCSP leading sequence for tPA (human plasminogen activator) (GenBank Accession no. K03021). In addition, the transmembrane GPI-anchor domain was removed from the *Plasmodium vivax* circumsporozoite protein (PvCSP) genes to allow protein secretion from any virus-transduced cell. The chimeric PvCSP vaccine insert consisted of the N- and C-terminal region from the Salvador I strain (NCBI Reference Sequence XP_001613068.1) flanking the central repeat regions of the circumsporozoite (CSP) VK210 of the Belem strain (GenBank accession number P08677) or VK247 of the Papua New Guinea (PNG) (GenBank accession number M69059.1). The central repeat region was designed using segments of 9 amino acid repeats as follows:

```
VK210
                                      (SEQ ID NO: 3)
5 × (GDRAAGQPA), (SEQ ID NO: 4)
4 × (GDRADGQPA), (SEQ ID NO: 5)
1 × (GNGAGGQAA))

VK247
                                     (SEQ ID NO: 11)
2 × (ANGAGNQPG/ANGAGGQAA), (SEQ ID NO: 12)
1 × (ANGAGDQPG/ANGAGDQPG), (SEQ ID NO: 13)
1 × (ANGADDQPG/ANGAGDQPG), (SEQ ID NO: 14)
1 × (EDGAGNQPG/ANGAGDQPG)).
```

A region II-plus was included in the C-terminal sequence of the vaccine (EWTPCSVTCG) (SEQ ID NO: 31) [53], as well as an insertion region in the C-terminal sequence of PvCSP (GAGGQAAGGNA) (SEQ ID NO: 33) [54]. The VK210 vaccine insert consisted of the Salvador I strain sequence, while the VK247 consisted of the PNG sequence with the accession numbers mentioned above. A control viral vector lacking the expression of any transgene was used as a control in mock-vaccinated mice.

Viral Vector Construction

All of DNA constructs required for ChAd63 were cloned in two steps. In the first step, unique Acc65I and NotI sites were used to insert the synthetic transgenes into an adenovirus entry plasmid. The transgene was placed upstream of BGH poly(A) transcription termination sequence and under the control of the long cytomegalovirus (CMV) promoter (containing a regulatory element, an enhancer and an intron A). The entry plasmid also contained attachment L (attL) sequences, which were required for site-specific recombination with attachment R (attR) sites located on the destination vector.

In the second step of cloning, an in vitro Gateway reaction was performed mediated by LR Clonase II system (Invitrogen), whereby the transgene of the entry vector was integrated into the destination plasmid by site-specific recombinase through an attL-attR interaction. The diagnostic PCR was performed to confirm the desired integration before completing the production of the recombinant ChAd63.

Similarly, all of the malarial genes were inserted into an MVA shuttle vector using a similar cloning strategy. Unique Acc65I and XhoI sites were used for transgene restriction and ligation and the transgenes were inserted under the control of an endogenous P7.5 promoter. PCR and RFLP were used to verify the correct insertion before linearization of the MVA plasmid.

Rv21 HepB Surface Antigen VLP Design and Development

A gene containing a chimeric CSP sequence comprising the repeat regions VK210 and VK247, followed by the C-terminal sequence (210/247C) was designed to be fused to the Hepatitis B surface antigen (HepBsAg). The sequence was codon-optimised for optimal expression in yeast and purchased in GeneArt® (InVitrogen). DNA sequences were similar to those expressed by recombinant ChAd and MVA viruses, but without the N-terminal CSP region. The construct was cloned into the pPink-HC intracellular Pichia plasmid and amplified in E. coli. Upon plasmid linearization, four strains of Pichia pastoris (knock out for ade2, ade2-pep4, ade2-prb1, ade2-pep4-prb1) were electroporated and white colonies were selected using PAD selection plates. Protein expression was induced by addition of methanol and a kinetics analysis was used to select the highest protein production and an optimal time point. Purification of the protein/VLP was made in an affinity column in presence of imidazol, followed by gel filtration. Fractions from gel filtration and affinity column were analyzed by SDS-PAGE and subsequently transferred to nitrocellulose membranes, blocked in 5% skimmed milk/PBS followed by addition of primary and secondary antibodies. VLP-containing fractions from the gel filtration column were confirmed with anti-HepBsAg, anti-PvCSP VK210 and anti-PvCSP VK247 primary mouse antibodies, diluted in 3% BSA/PBS to 1:200, 1:20,000 and 1:20,000 respectively (MR4). A secondary donkey anti-mouse-AP conjugate in 3% BSA/PBS and Sigmafast™ BCIP/NBT tablets (Sigma-Aldrich) were used for development. Silver staining was used to analyse purity of the fractions from the FPLC column and of progressive stages of the VLP purification process. The samples were run on Mini-PROTEAN 12% gels (BioRad) with the Pierce unstained protein ladder (Thermo Scientific) run for reference. The gels were subjected to silver staining using a Pierce silver stain kit (Thermo Scientific). Direct staining of gels was carried out according to manufacturer's instructions. The particle-containing fraction from the sephacryl gel filtration column was negatively stained with 2% uranyl acetate. The sample was then imaged using a FEI Tecnai 12 Transmission Electron Microscope (TEM).

Immunization of Mice

Mice were primed with simian adenoviral vector 63 (ChAd63) encoding PvCSP at a dose of $1 \times 10^8$ infectious units (iu) and 8 weeks later boosted with vaccinia-modified virus strain Ankara (MVA) encoding the same transgene at a concentration of $1 \times 10^6$ plaque forming unit (pfu) per mouse. All viral vector vaccines were administered intramuscularly (i.m.) in endotoxin-free PBS. The Rv21 VLP vaccine was administered i.m. at a dose of 0.5 µg/mouse in endotoxin-free PBS.

Whole IgG Enzyme-Linked Immunosorbent Assay (ELISA)

ELISAs measuring total IgG were carried out as described previously [24]. Serum antibody endpoint titers were taken as the x-axis intercept of the dilution curve at an absorbance value three standard deviations greater than the OD405 for serum from a naïve mouse. Results were also calculated using a standardized ELISA by including a high-titre reference serum from hyper-immune mice to each ELISA plate to produce a standard curve, which in turn was used to quantify and assign ELISA units to each sample [55]. Briefly, Nunc Maxisorp Immuno ELISA plates were coated with the antigens diluted in PBS to a final concentration of 2 µg/mL. Each plate contained a standard curve, negative and positive controls, as well as serum samples of mice pre-boost (1:300) or post-boost (1:3000). An anti-mouse IgG coupled to alkaline phosphatase was used as a secondary antibody. Development was made with 4-nitrophenylphosphate diluted in diethanolamine buffer. Data was fitted to a four parameter hyperbolic curve [56].

Expression and Purification of PvCSP VK210 and VK247 Proteins

The codon optimized genes of *P. vivax* CSP containing VK210 or VK247 repeats were cloned into the pHLsec vector [57] with a C-terminal hexahistidine tag. Protein was expressed by transient transfection in HEK-293T cells and purified from dialyzed (against PBS buffer) conditioned medium by immobilized $Co^{2+}$-affinity chromatography followed by size-exclusion chromatography in 20 mM Tris-HCl pH 8.0, 300 mM NaCl [40].

Peptides

Crude 20-mer peptides overlapping by 10 amino acids and representing full-lengths of *P. vivax* CSP VK210 and VK247 were synthesized by Mimotopes (Victoria, Australia). Individual peptide pools were used at a final concentration of 5 μg/mL.

Ex-Vivo IFN-γ ELISPOT Assay

Ex vivo IFN-gamma (IFN-γ) ELISPOTs were carried out using PBMCs isolated from the blood as previously described [58, 59]. MAIP ELISPOT plates (Millipore) were used to plate cells. Anti-mouse IFN-γ mAb and development reagents were used according to the manufacturer specifications (Mabtech).

Intracellular Cytokine Staining (ICS)

Peripheral mononuclear cells (PBMCs) were stimulated for 5 hours in the presence of TRAP peptide pools described above. Hepatic cellular responses were assessed from perfused livers that were digested with collagenase and treated with ACK buffer to lyse red blood cells. Phenotypic and functional analysis of $CD8^+$ and $CD4^+$ T cells were performed using the following antibody clones: anti-CD8 PerCP-Cy5.5 (clone 53-6.7), and eFluor650 coupled anti-CD4 (GK1.5), anti-IFN-γ APC (XMG1.2), anti-TNF-α eFluor 450 (MP6-XT22), anti-IL-2 PE-Cy 7 (JES6-5H4). Flow cytometric analyses were performed using an LSRII instrument. Frequencies of cells producing cytokines in the graphs represent data where background from non-stimulated cells was subtracted. Data were analyzed with either FACSDiva or FlowJo software.

Infection of Mice

Mice were challenged with 2,000 wild type or transgenic *P. berghei* sporozoites. Infection was monitored from day 5 to 20 by Giemsa staining of blood smears.

Statistical Model for Parasitaemia Prediction

Percent parasitaemia was used to calculate the time required to reach a blood-stage infection of 1%, or time to 1% parasitaemia. This was predicted using a linear regression model as described previously [25]. Briefly, blood parasite counts were obtained for 3-5 consecutive days starting on day 5 after the challenge. Blood smears were stained with Giemsa, and percentages of parasitaemia calculated in all animals. The logarithm to base 10 of the calculated percentage of parasitaemia was plotted against the time after challenge and Prism 5 for Mac OS X (GraphPad software) statistical analysis package used for generating a linear regression model on the linear part of the blood-stage growth curve.

Statistical Analysis

For all statistical analyses, GraphPad Prism version 5.0 for Max OS was used unless indicated otherwise. Prior to statistical analysis to compare two or more populations, the Kolmogorov-Smirnov test for normality was used to determine whether the values followed a Gaussian distribution. An unpaired t-test was employed to compare two normally distributed groups, whereas Mann-Whitney rank test was used for comparing two non-parametric groups. If more than two groups were present non-parametric data was compared using Kruskal-Wallis test with Dunn's multiple comparison post-test, whereas normally distributed data were analyzed by one-way ANOVA with Bonferroni's multiple comparison post-test. The effect of two variables was explored using two-way ANOVA with Bonferroni's multiple comparison post-test. Correlation strength was tested using either Pearson's or Spearman's tests as indicated in the results chapters. Kaplan-Meier survival curves were used to represent protective efficacy to a challenge with any *P. berghei* parasite lines. All ELISA titres were also log 10 transformed before analysis. The value of $p<0.05$ was considered statistically significant ($*p<0.05$, $p<0.01$, $p<0.001$, and $***p<0.001$).

Example 2: Cellular Immune Responses are not Induced in Mice Immunized with *P. vivax* Circumsporozoite Viral-Vectored Vaccines (PvCSP vv)

We first assessed whether viral-vectored vaccines (vv) expressing the *P. vivax* circumsporozoite protein (PvCSP) could induce cellular immune responses in inbred or outbred mouse strains. We generated four recombinant adenoviruses from chimpanzee origin (ChAd63) and four Modified Vaccinia Ankara (MVA) vv expressing various versions of PvCSP (PvCSP vv). The resulting recombinant viruses contained a series of PvCSP expression cassettes encoding the PvCSP N- and C-terminal sequences of the Salvador I strain, including or excluding certain selected central repeat sequences which are present in the two major PvCSP alleles VK210 and VK247 (FIG. 1A) [8].

First, a set of ChAd63 and MVA vv expressing only the N- and C-terminal sequences and no central repeats were generated (NC); a second set of vv contained a series of selected VK210 repeats [8]flanked by the same NC sequences (N210C); a third set expressed VK247 repeats flanked by NC (N247C). Finally we generated a ChAd63/MVA set expressing a chimeric CSP containing both type of repeats (VK210/247) flanked by NC (N210/247C). Groups of mice (n=6) received a homologous ChAd63-MVA prime-boost at an interval of eight weeks between immunizations (FIG. 1B). Cellular immune responses in mice were quantified two weeks after the final immunization using an ex vivo IFN-γ ELISpot assay and stimulating peripheral blood mononuclear cells (PBMCs) with a series of peptide pools designed to assess responses against either N210C or N247C (FIG. 1C, D). An initial experiment using the prime-boost regimen in inbred C57Bl/6 mice did not yield any positive responses (FIG. 1C, D; upper panel). This prompted the assessment of responses in additional mouse strains immunized using the same vaccination scheme. None of these additional mouse strains (C3H/He, BALB/c or outbred CD1) showed detectable antigen-specific T cell responses (FIG. 1C, D) and we concluded that the PvCSP molecules that we used in our vv do not have immunodominant T cell epitopes in the animal models tested. These results are in agreement with earlier observations made with a similar vaccine candidate expressing PvCSP for which no evidence was found for the presence of immunodominant T cell epitopes [9].

Figure 2:
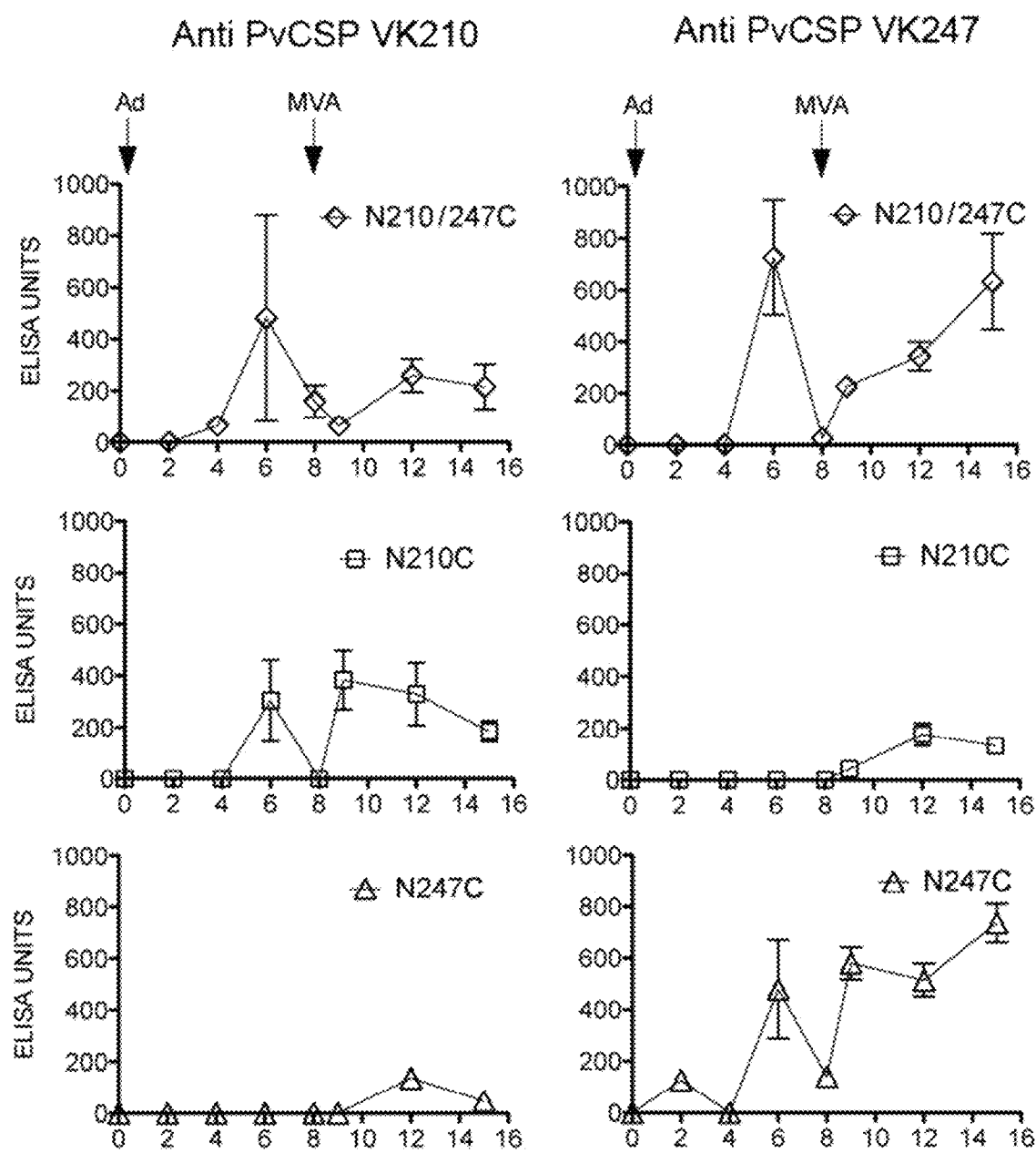
FIG. 2. Antibody responses following immunization with viral-vectored vaccines (vv; ChAd63 or MVA) expressing different versions of PvCSP. Outbred CD-1 mice were immunized with vv expressing various versions of PvCSP (N210/N247C, N210C, N247C, NC; see FIG. 1) using an interval of 8 weeks. Control groups were mock-vaccinated with vv expressing *P. berghei* CSP and naive mice were injected with PBS. Serum was collected every two weeks and antibody titers were quantified using a standardized ELISA against the PvCSP VK210 and VK247 antigens.
Figure 2:
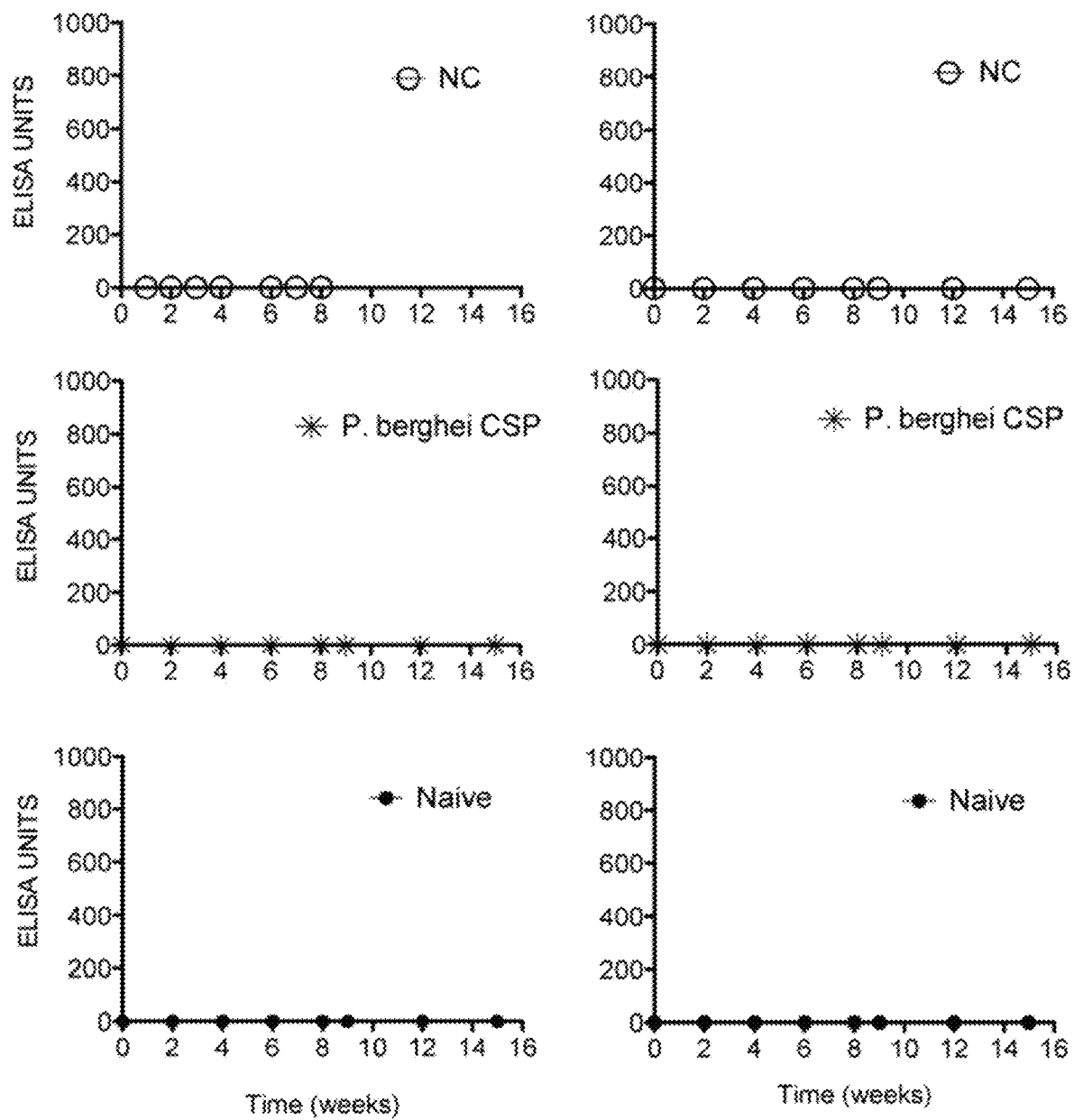

Example 3: Humoral Immune Responses are Induced in Mice Immunized with the PvCSP vv We next assessed antibody responses induced by the ChAd63 and MVA vaccination protocols described above, using C57BL/6 mice (FIG. 1B). Serum samples were collected on fortnightly basis up until week 16 after the first immunization. We observed that immunization with the vv expressing the chimeric construct N210/247C induced antibody responses to both VK210 and the VK247 PvCSP (FIG. 2, top panel). In contrast, responses after an immunization with ChAd63 vv encoding only N210C or N247C, elicited antibodies only against their cognate version of PvCSP (FIG. 2). However, low antibody titres against the heterologous PvCSP allele were detected after a boost with the MVA vv, suggesting that several encounters with the antigen may stimulate low levels of cross-reactive antibody responses. No antibody responses were detected after a ChAd63-MVA immunization with either the NC or with vv expressing rodent *P. berghei* CSP (FIG. 2).

Figure 3:
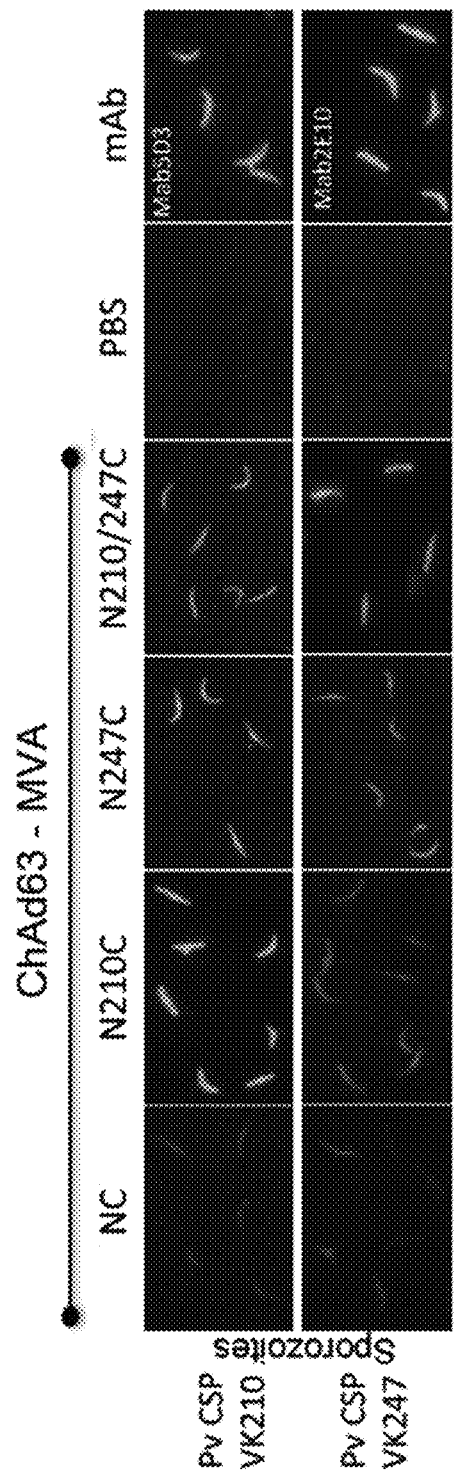
FIG. 3. Immunofluorescence Assay (IFA) to assess CSP antibody reactivity of sera from immunized mouse on the surface of wild type *P. vivax* parasites isolated from Chiapas, Mexico. (A) Serum obtained from C57Bl/6 mice was incubated with *P. vivax* VK210 (top panel) or VK247 (bottom panel) sporozoites collected from the endemic state of Chiapas, Mexico. Each mouse group was immunized with ChAd63-MVA vv expressing homologous PvCSP transgenes (NC, N210C, N247C, N210/247C) and sera was obtained on week two after the final immunization. PBS and monoclonal antibodies with specificity to VK210 (Mab5D3) or VK247 (Mab2E10) were used as negative or positive controls, respectively. The experiment was performed using 6 mice/group and three batches of sporozoites for each sample.

Example 4: *P. vivax* Sporozoites Isolated from Chiapas, Mexico are Recognized by Antibodies Induced in Mice after PvCSP vv Vaccination We addressed the question whether mouse antibodies raised by immunisation with various PvCSP antigens encoded by the vv could recognize CSP on the surface of *P. vivax* sporozoites collected from patients in the endemic region of Tapachula, Chiapas [29]. We performed immunofluorescence assays (IFAs) using two types of sporozoites, VK210 and VK247 belonging to three different sporozoite batches, all yielding similar results. Results shown in FIG. 3 were obtained using sera from ChAd63-MVA PvCSP-immunized C57Bl/6 mice, but CD-1 mouse sera yielded similar results. Samples were collected on week 2 after the final boost immunization (FIG. 3). Serum from immunized mice reacted with both sporozoites expressing the VK210 allele (FIG. 3, top panel) and sporozoites expressing the VK247 allele (FIG. 3, bottom panel).

Example 5: Development of a Rodent Challenge Model for Assessing Protective Efficacy of the PvCSP Vaccination In order to assess the in vivo protective efficacy of the *P. vivax* vaccines, we developed rodent challenge models, which involved creating transgenic *P. berghei* sporozoites where Pbcsp was replaced with either full length VK210 Pvcsp or VK247 Pvcsp. These transgenic parasites were generated using the gene insertion/marker out (GIMO) based transfection technology [30, 31]. Using this technology, we generated two Double-step Replacement (DsR) mutants [32] that resulted in the coding sequence (CDS) of *P. berghei* csp being replaced with the CDS of the Pvcsp in a two-step GIMO-transfection procedure (FIG. 4). First, the *P. berghei* csp coding sequence (CDS) was deleted by replacement with the hdhfr::yfcu selectable marker cassette (SM) (FIG. 4A, Step 1). Subsequently, in these *P. berghei* csp GIMO-deletion parasites the *P. vivax* csp CDS was inserted into the same locus thereby replacing hdhfr::yfcu with the *P. vivax* csp CDS (FIG. 4A, Step 2). These parasites have replaced full-length *P. berghei* csp CDS with that of Pvcsp and are SM free. In the two transgenic parasite lines, PbANKA-PvCS VK210(r)$_{PbCS}$ (line 2196cl1) and PbANKA-PvCS VK247(r)$_{PbCS}$ (line 2199cl1) the *P. vivax* csp gene is under the control of the *P. berghei* csp gene promoter (5'UTR) and transcription terminator (3'UTR) regulatory elements. In addition to expressing PvCSP, these transgenic parasites constitutively express the fusion GFP::luciferase reporter protein, which permits a determination of parasite liver-loads in the liver by real-time in vivo imaging (FIG. 4B). Correct replacement of the *P. berghei* csp CDS by the *P. vivax* csp CDS in the two transgenic lines was confirmed by diagnostic Southern analysis of chromosomes separated by pulsed-field gel electrophoresis and diagnostic PCR on genomic DNA (FIG. 4C). Immunofluorescence microscopy of sporozoites using anti-*P. vivax* CSP monoclonal antibodies to the repeat region of the VK210 or VK247 proteins, confirmed the expression of either PvCSP VK210 or VK247 in the two transgenic parasite lines (FIGS. 4E, F and G). The *P. berghei* CSP-specific monoclonal antibody, 3D11, confirmed expression *P. berghei* CSP in wild type *P. berghei* sporozoites but anti-*P. berghei* CSP staining was absent in either PbANKA-PvCS VK210(r)$_{PbCS}$ or PbANKA-PvCS VK247(r)$_{PbCS}$ sporozoites (FIG. 4) [33, 34].

Figure 5A:
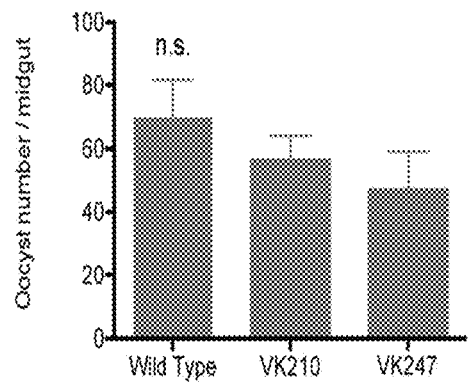
Figure 5B:
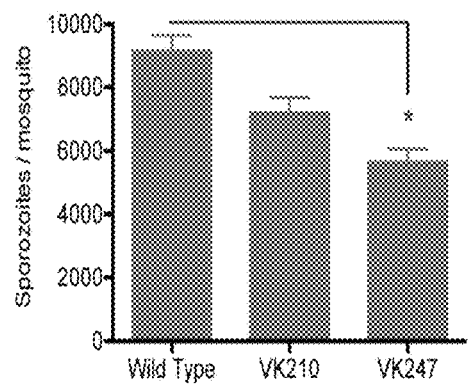
Figure 5C:
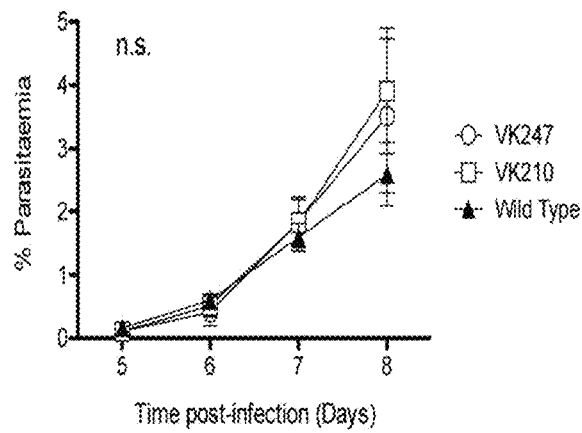
Figure 5D:
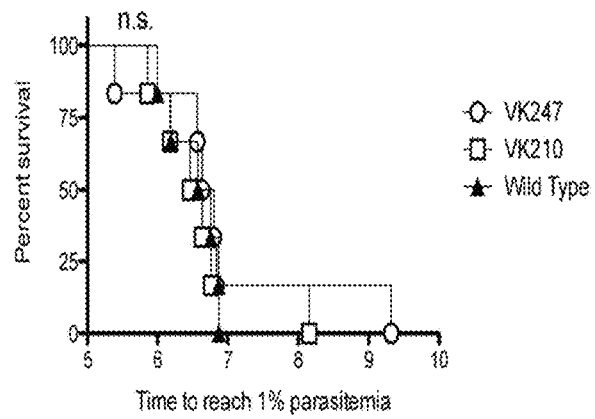

We next assessed the ability of these two transgenic parasites to produce oocysts and sporozoites since replacing the endogenous csp gene with *P. vivax* csp could alter these characteristics. Oocyst production in *A. stephensi* of the two transgenic parasite lines was similar to oocyst production of WT *P. berghei* (FIG. 5A, p=0.24). Similarly, the PbANKA-PvCS VK210(r)$_{PbCS}$ parasites produced salivary gland sporozoites comparable to WT parasites. In contrast, the PbANKA-PvCS VK247(r)$_{PbCS}$ parasites showed significant (~30%) reduction in sporozoites production compared to WT *P. berghei* parasites (FIG. 5B, p<0.05). The infectivity of sporozoites of both transgenic parasites was assessed by determination of the prepatent period (i.e. the time to 1% parasitaemia) after intravenous injection of 2,000 sporozoites in the tail vein of outbred CD-1 mice (Harlan, UK). All sporozoites were capable of a liver infection and, moreover, the time to 1% parasitemia was not significantly different between WT, PbANKA-PvCS VK210(r)$_{PbCS}$ or PbANKA-PvCS VK247(r)$_{PbCS}$ parasites (6.7, 6.5 and 6.7 days, respectively; FIG. 5C,D).

These results demonstrate that transgenic *P. berghei* parasites expressing PvCSP alleles in place of PbCSP produce fully infectious sporozoites, which are able to complete liver stage development in mice.

Example 6: Protective Efficacy of PvCSP vv Vaccines Against a Sporozoite Challenge with *P. berghei* PvCSP Transgenic Parasites We next determined vaccination efficacy by challenging vv-immunized mice with the transgenic *P. berghei* PvCSP transgenic parasites. These mice were immunised with the 4 different (ChAd63-MVA) PvCSP vv, as described above (FIG. 1A). Protective efficacy in these challenged mice was determined by measuring the prepatent period after intravenous injection of 2,000 *P. berghei* PvCSP transgenic sporozoites. Mice were monitored four days post-infection onwards by thin film blood smears stained with Giemsa. Once positive blood-films had been confirmed on three consecutive days, or mice had reached the end-point of twenty days parasite free (sterile protection), mice were sacrificed. The prepatent period, defined as the time to reach 1% parasitaemia, was subsequently calculated using a linear regression based on the three consecutive thin blood films, as described previously [25].

Figure 6A:
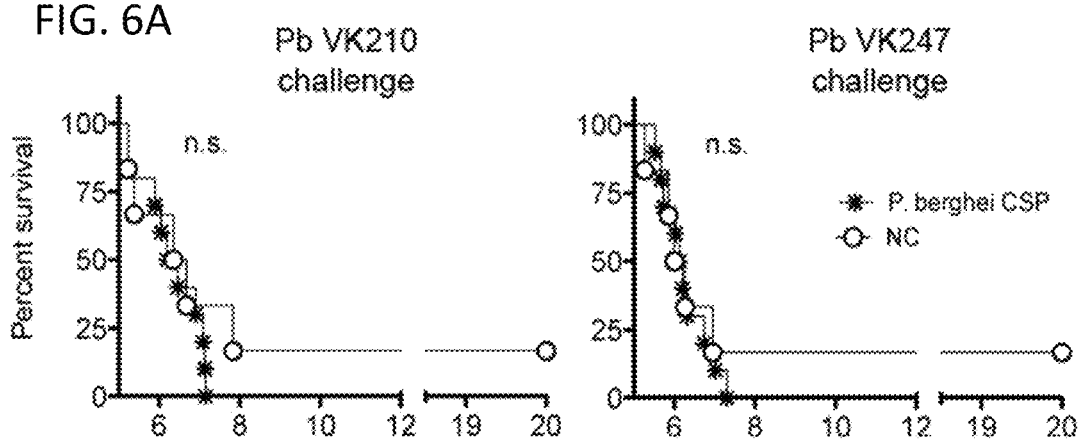
Figure 6B:
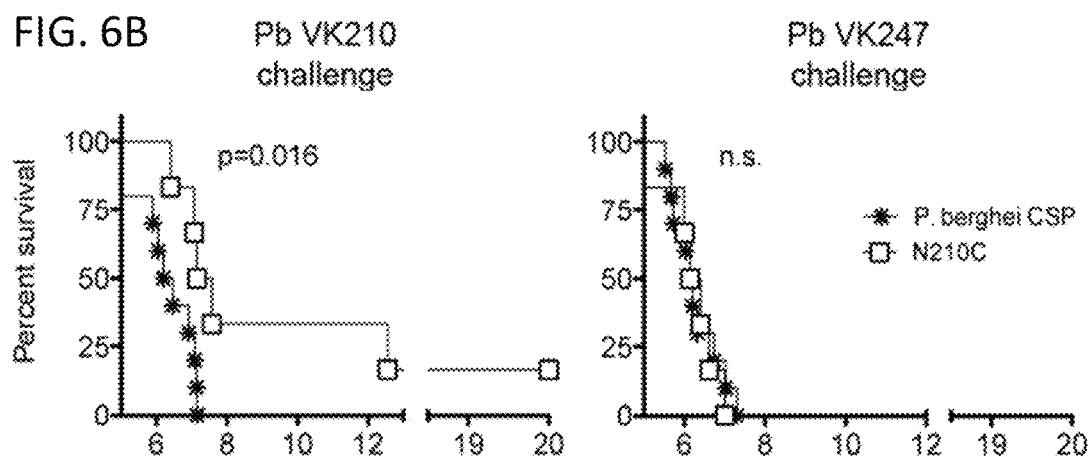
Figure 6C:
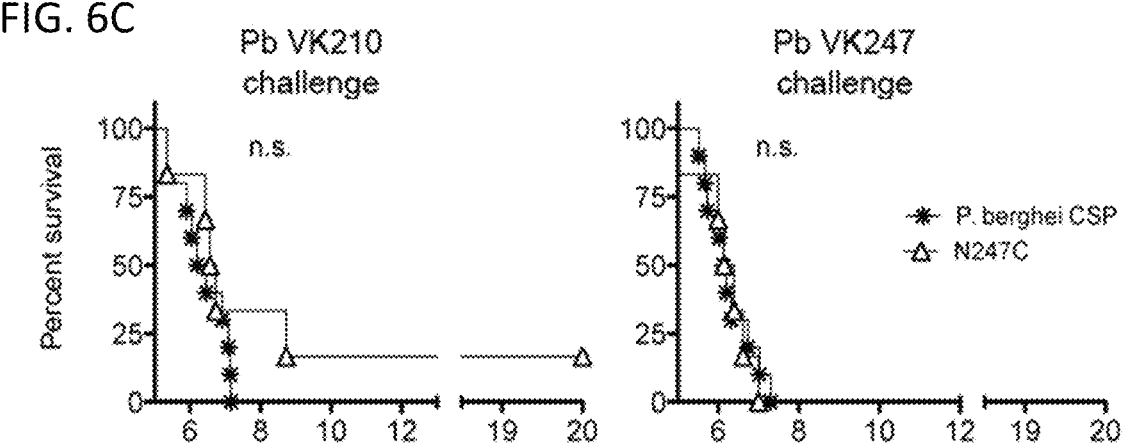
Figure 6D:
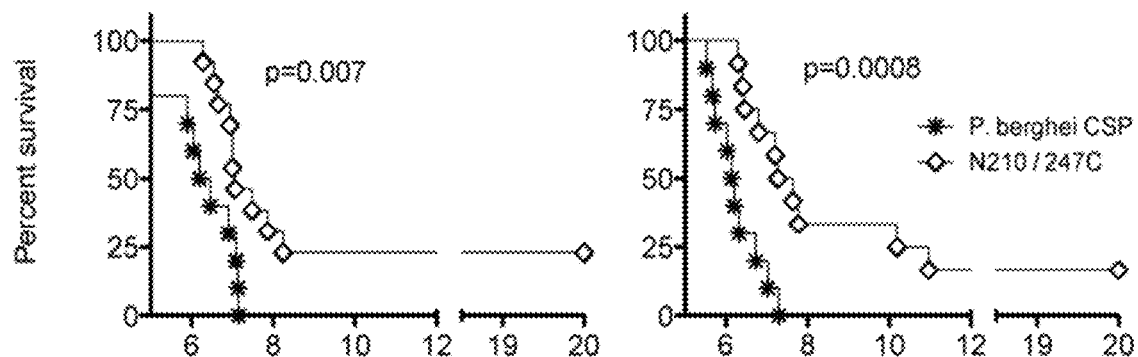

Our results indicated that the PvCSP central repeat sequences are necessary to generate protective immunity, as immunisations with NC only (i.e. lacking either VK210 or 247 repeat sequences) failed to induce protective immunity, demonstrated by the prepatent period being similar to mock immunized control mice (FIG. 6A). N210C immunisation resulted in partial protection against a challenge with the transgenic parasites expressing VK210, producing a significant (p=0.016) prolonged (prepatent period). In contrast, N210C immunization did not delay the time to patency of transgenic parasites expressing VK247 (FIG. 6B). Immunisation with the N247C vv did not induce protection against the transgenic parasites expressing either VK247 or VK210 (FIG. 6C). However, immunization with the chimeric N210/247C induced a significant delay in the prepatent period after challenge with both transgenic parasites expressing either VK210 (p=0.007) or VK247 (p=0.0008) and moreover, 25% and 16% of the immunized mice did not succumb to a blood stage infection with the VK210 or VK247 parasites, respectively (FIG. 6D).

Figure 6E:
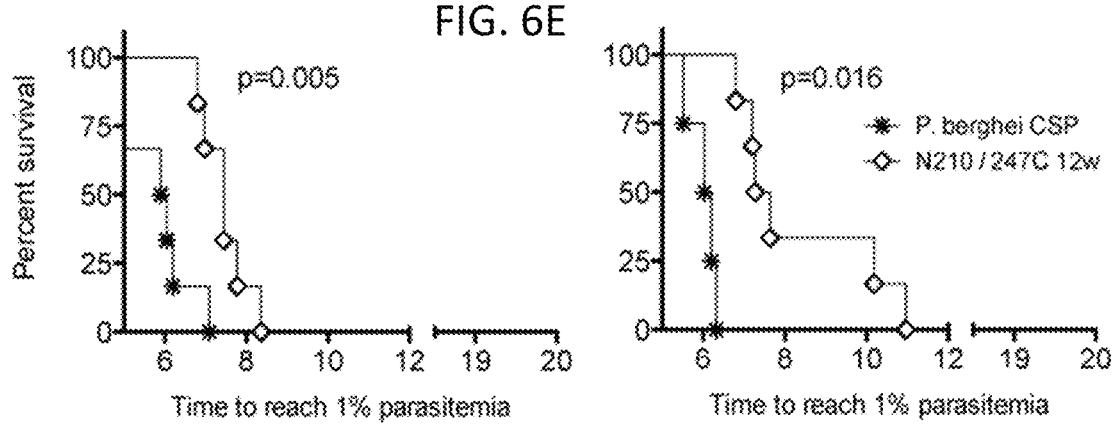
Figure 6F:
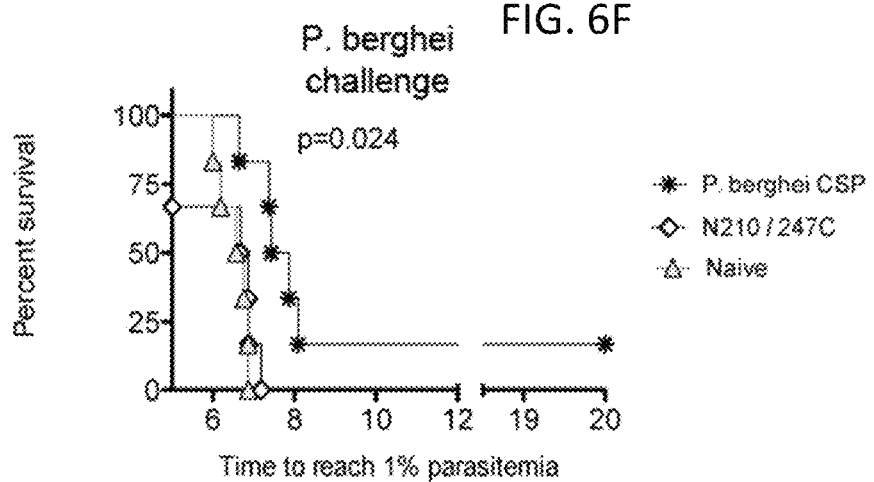

While significant protective immunity was maintained 12 weeks after immunisation with the N210/247C vector as determined by a prolonged prepatent period after challenge with either VK210 (p=0.005) or VK247 (p=0.016) transgenic sporozoites, sterile protection was not induced as all mice eventually developed a blood stage infection (FIG. 6E). We confirmed the absence of unspecific protection induced by immunisation with the N210/247C vv vaccination through challenge of the immunised mice with wild-type P. berghei sporozoites. These mice were not protected and protection against wild-type P. berghei sporozoites was only induced in mice after a prime-boost (ChAd63-MVA) immunisation regime with a vv expressing P. berghei CS protein (p=0.024; FIG. 6F). These results demonstrate that immune responses to the central PvCSP repeats are necessary to induce protective immune responses against infection. Moreover, a chimeric VK210/247 PvCSP vv containing repeats from both forms of PvCSP elicits protective immune responses against sporozoites expressing either VK210 or VK247, which are at least equal to if not better than after immunisation with a vaccine consisting of only one form of PvCSP.

Example 7: Vaccination with the Rv21 VLP, Presenting the Chimeric PvCSP VK210/247 Antigen Fused to the Hepatitis B Surface (HepB S), Antigen Induces High Levels of Protective Immunity in Mice The ability to induce antibody-mediated protective immunity by the PvCSP vv in the absence of detectable cellular responses led us to develop a VLP vaccine platform with a greater potential to enhance humoral responses against PvCSP. VLPs are known for their ability to induce high antibody titres, and are a leading vaccine platform not only for malaria [5] but also for HPV [35]. RTS,S/AS is based on the hepatitis B surface antigen virus-like particle (VLP) platform, genetically-engineered to include the central repeats and carboxy (C-) terminus (amino acids 207-395) of the P. falciparum CSP antigen [36]. We developed a VLP consisting of the chimeric PvCSP VK210/VK247 central repeats and the CSP C-terminal sequence fused to the Hepatitis B Surface Antigen (HepB-S) gene. Codon usage of the fusion gene was optimized for expression in Pichia pastoris and production of the fusion protein (PvCSP-HepB-S) was assessed in four yeast strains using a kinetics analysis.

Figure 7A:
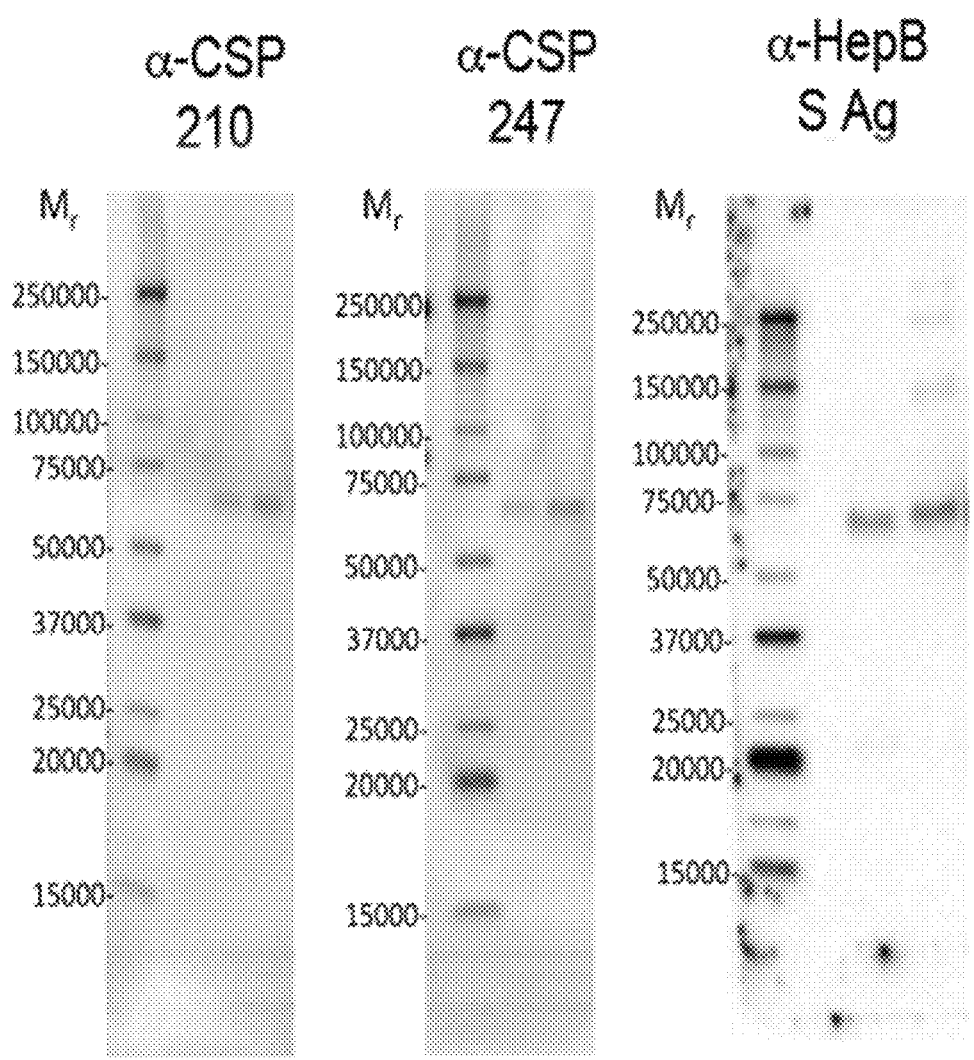
Figure 7C:
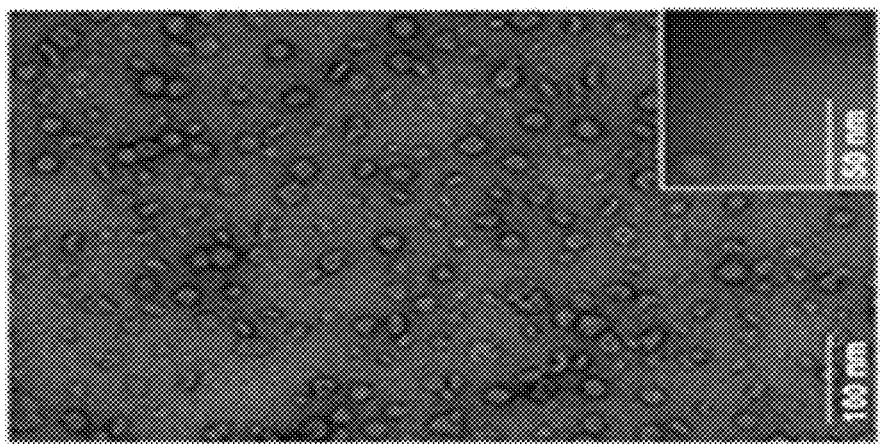
Figure 7B:
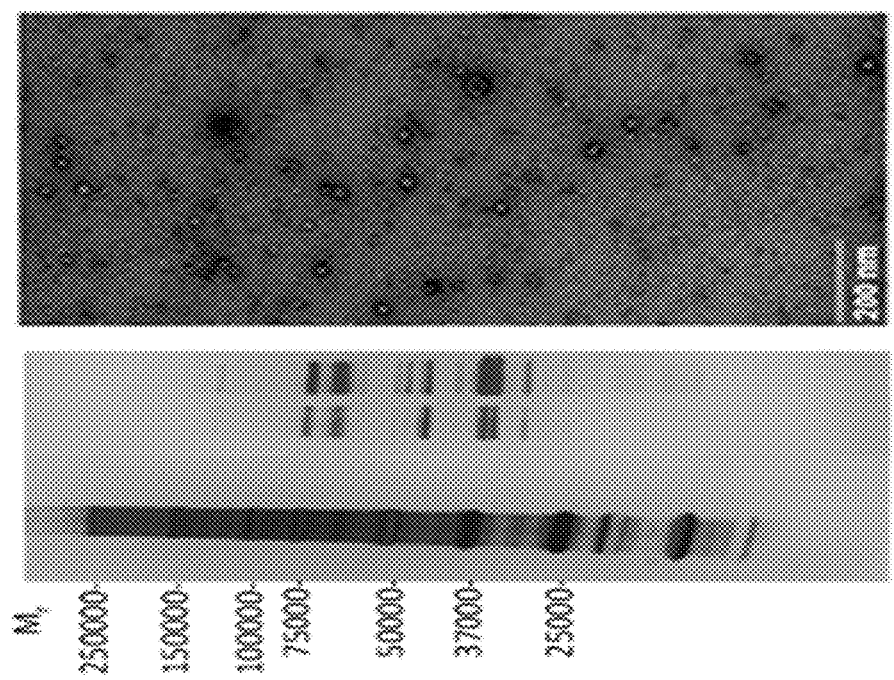

We selected a P. pastoris colony that had optimal expression levels, which peaked after 108 hours (FIG. 7A). Presence of the fusion protein PvCSP-HepB S was confirmed by Western blot analyses using antibodies against PvCSP VK210, PvCs VK247 and HepB S (FIG. 7B). Presence, size and purity of the Rv21 protein was carried out using a sensitive silver stain technique (FIG. 7C, D left panel).

Figure 7D:
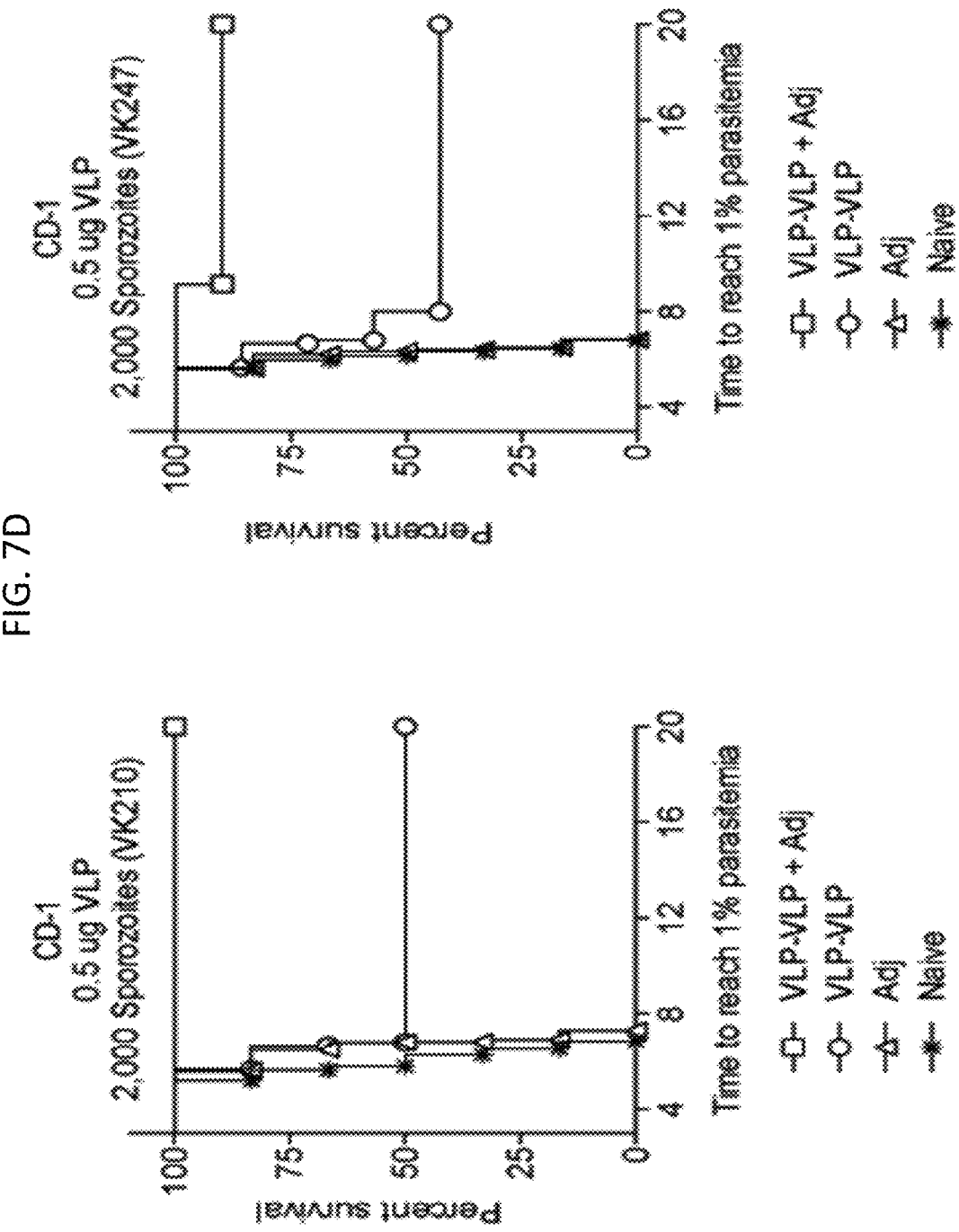
Figure 7E:
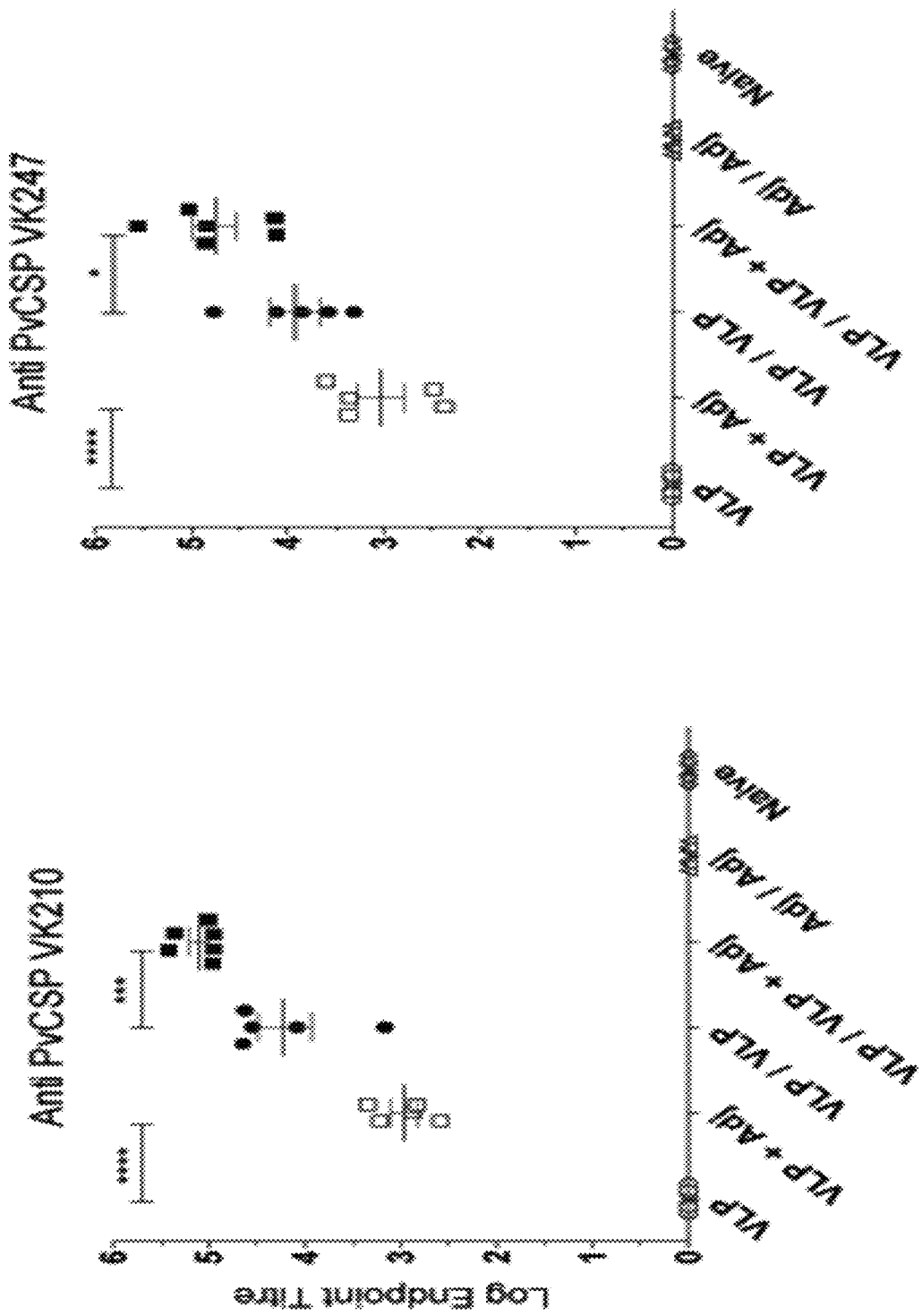
Figure 7F:
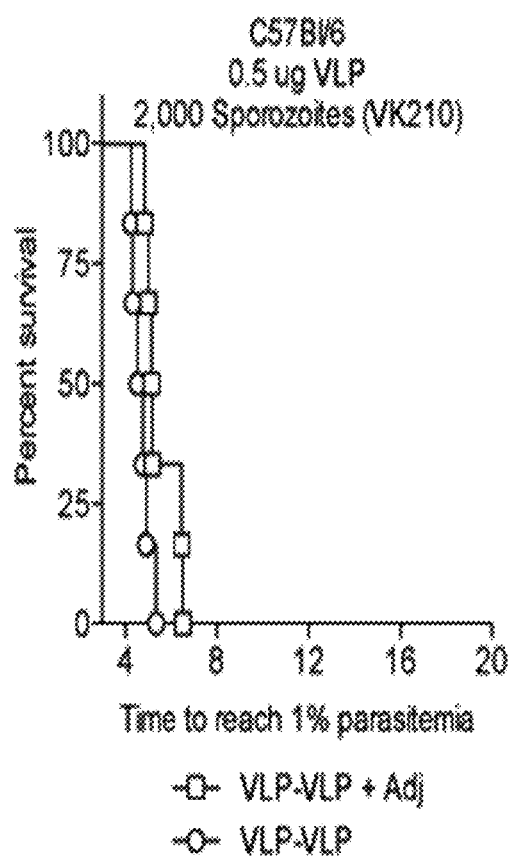
Figure 7F:
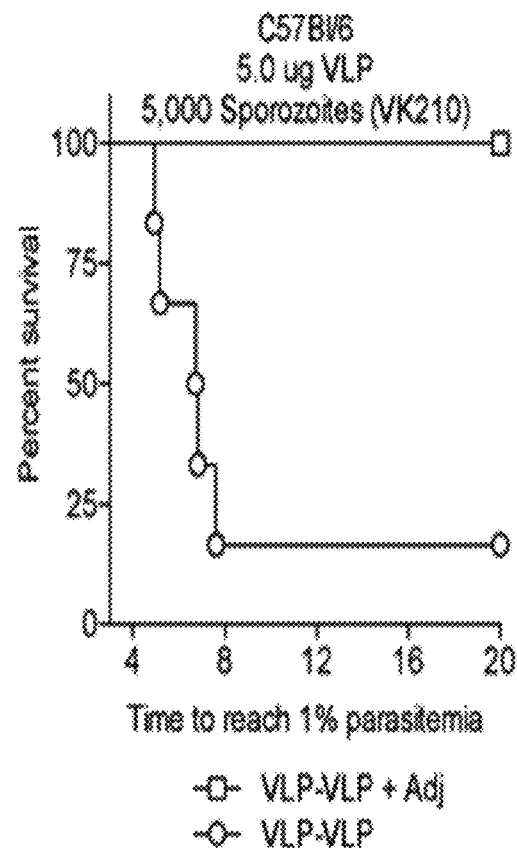

The protocol for purification of the fusion protein involved two steps. The first consisted of an affinity purification using a capture select C-tag molecule (Thermofisher) bound to the fusion protein. In addition to collecting the expected protein band corresponding to the PvCSP-HepB S protein, the sample also contained additional proteins. VLP particle formation was confirmed using transmission electron microscopy (TEM; FIG. 7C, right panel). A subsequent purification step was performed by size exclusion chromatography in order to obtain a single protein band of expected size of the PvCSP-HepB S protein (75 kDa), which was visualized using the silver staining technique. A further TEM analysis confirmed a cleaner preparation of VLPs (FIG. 7D, right panel). In FIG. 7E, a diagram is shown with the proposed structure of the VLP, which we have named Rv21. The purified Rv21 was used to immunize mice, using a low dose of 0.5 µg and employing a homologous prime-boost immunization protocol (FIG. 7F). Instead of the AS01 adjuvant, standardly used for RTS,S vaccination, Matrix-M adjuvant was used to enhance the immunogenicity and protective efficacy of Rv21. Matrix-M is suitable for human use and consists of saponin-based 40 nm particles that can activate and recruit immune cells to the draining lymph nodes and spleen [37, 38]. This adjuvant functions by inducing high titres of reactive antibodies supported by a balanced Th1/Th2 response [39].

Figure 7G:
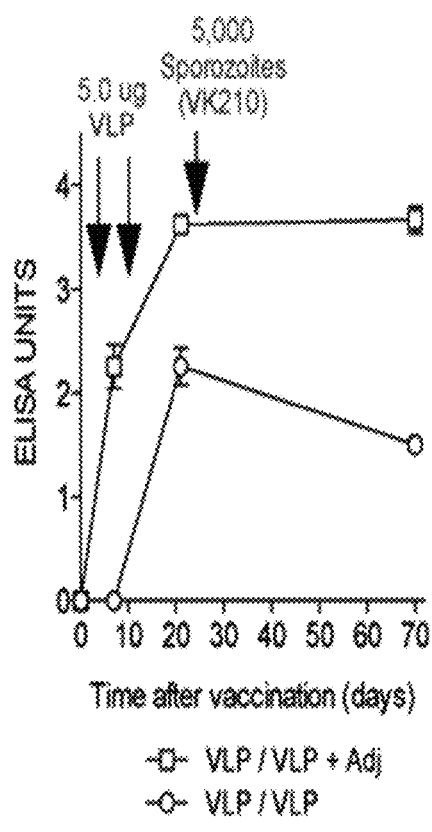
Figure 7G:
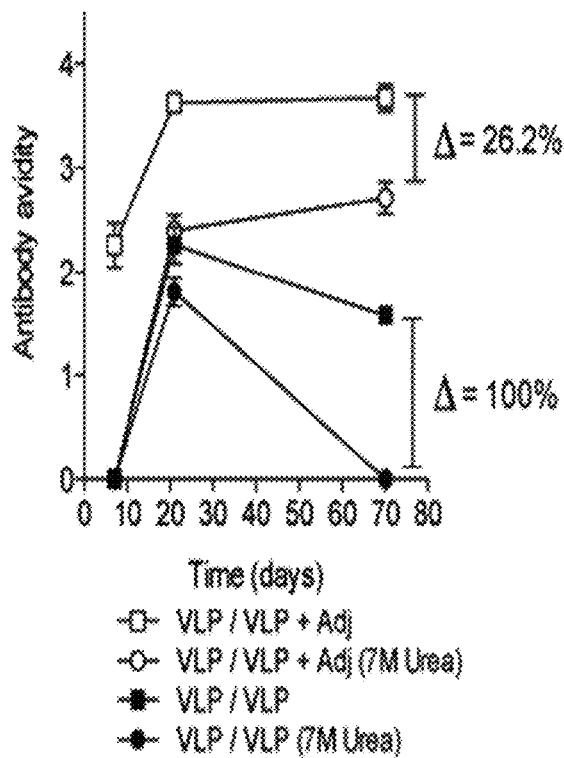

The protective efficacy of each prime-boost regimen was assessed by challenging the Rv21-immunized CD-1 mice with a dose of 2000 PbANKA-PvCS VK210$(r)_{PbCS}$ or PbANKA-PvCS VK247$(r)_{PbCS}$ transgenic sporozoites (FIG. 7G). Protective efficacy in these immunized mice was determined by measuring the prepatent period as described above. At the low dose (0.5 µg/mouse) of the Matrix-M-adjuvanted Rv21 prime-boost immunization, protective efficacy against challenge with PbANKA-PvCS VK210$(r)_{PbCS}$ sporozoites was 100% and against PbANKA-PvCS VK247 $(r)_{PbCS}$ sporozoites 90%, as confirmed by the absence of a blood infection 20 days after challenge (FIG. 7G). In contrast, all mice in the naïve group developed blood stage parasitemia with a prepatent period of 4-5 days. In the absence of the Matrix-M adjuvant, immunisation of mice using the VLP homologous prime-boost regime still generated sterile immunity in 50% of the VLP-immunized mice challenged with PbANKA-PvCS VK210$(r)_{PbCS}$ sporozoites and 43% of immunized mice were protected against a challenge of PbANKA-PvCS VK247$(r)_{PbCS}$ sporozoites (FIG. 7G).

Figure 7H:
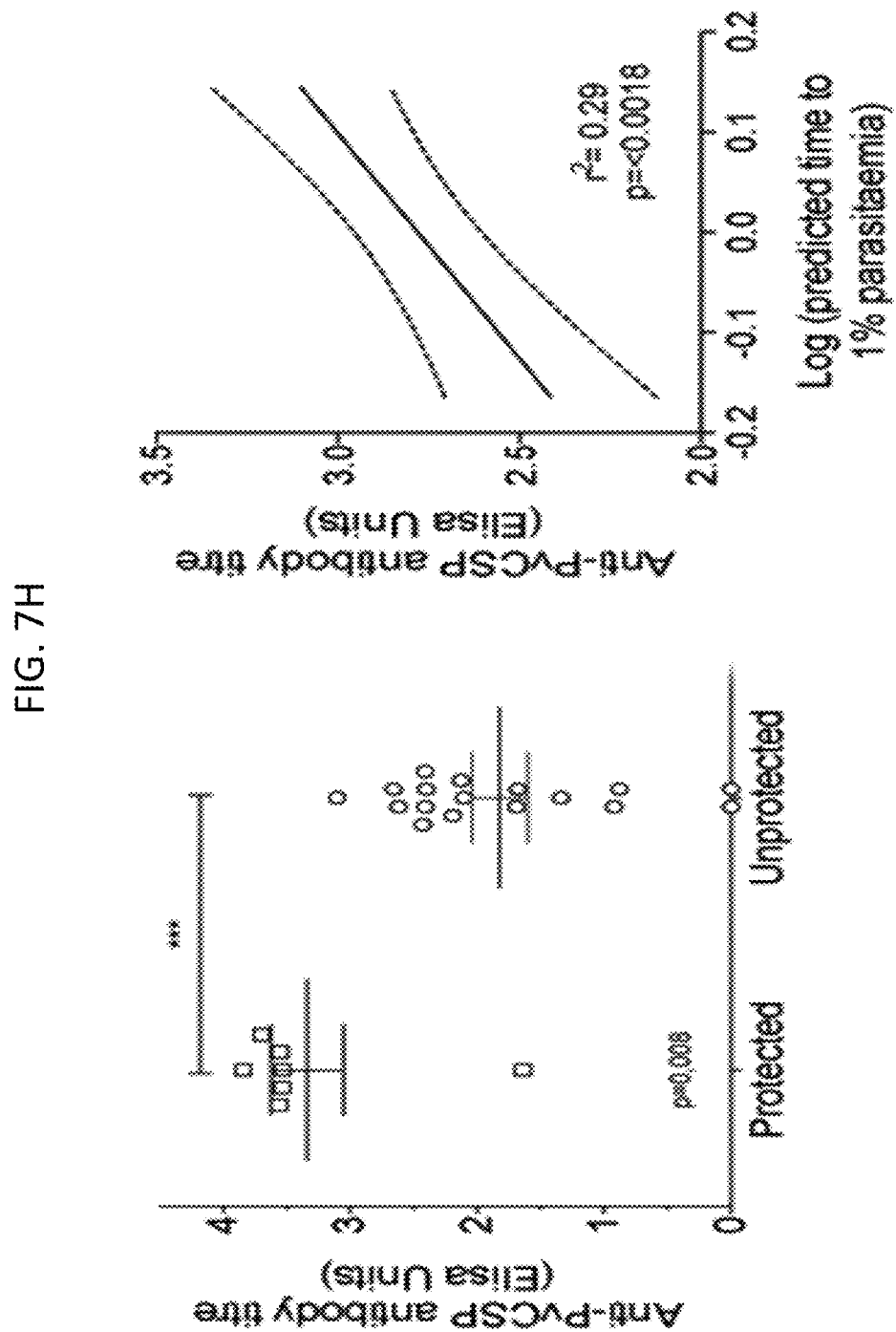

These results indicated the importance of both the VLP and the adjuvant in inducing protective immune responses of this vaccination regime. In addition, our results showed that PvCSP VLP-based vaccination induced higher protective efficacy than immunisation with the viral-vectored vaccine candidates. ELISA analyses of antibody responses to vaccination supported the importance of Matrix-M adjuvant to elicit high antibody titres to PvCSP, even after a single (priming) immunisation with Rv21 (FIG. 7H). A prime-boost regimen with Rv21 in the absence of the Matrix-M adjuvant induced higher titres than those by a single vaccination but still lower compared to the prime-boost regime with the adjuvant. We concluded that the Rv21 antibody responses benefit from the co-administration of an adjuvant, both in a single immunization or a prime-boost regime.

Figure 7I:
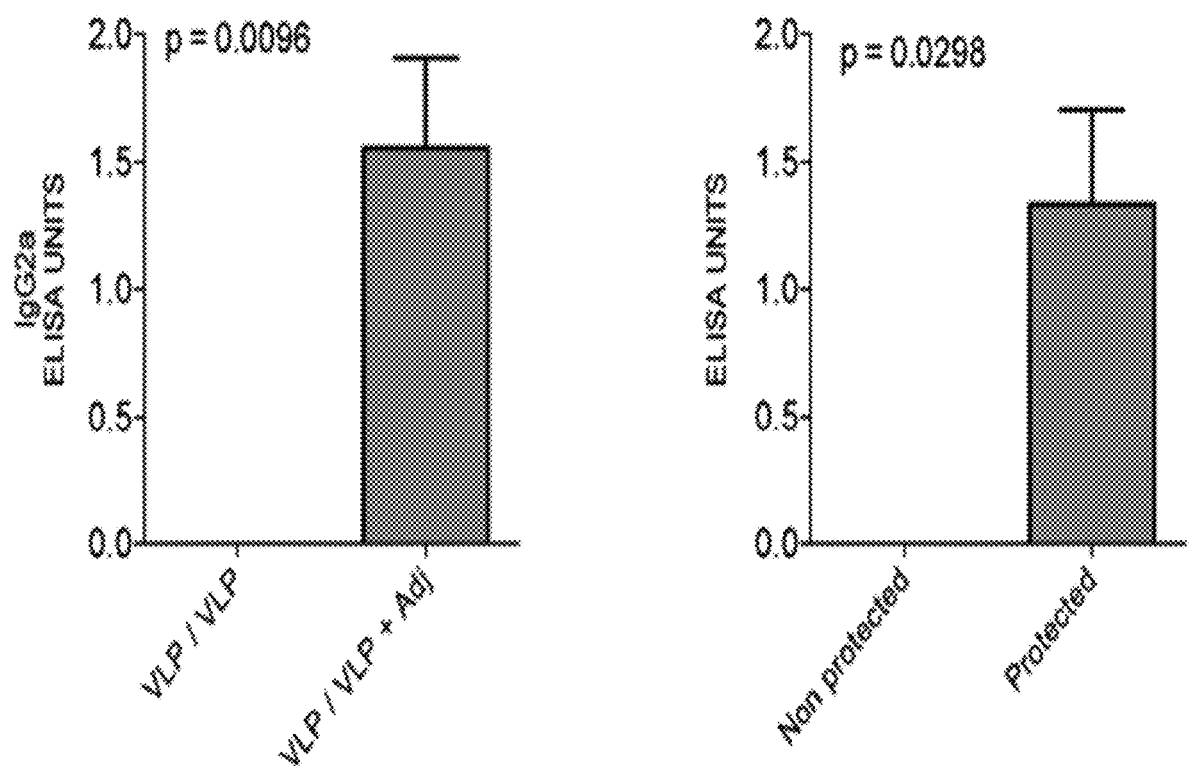

We tested Rv21 efficacy in C57BL/6, a mouse strain that has previously shown to be highly sensitive to a P. berghei sporozoite infection and for which we have previously failed to induce sterile immunity using a P. vivax TRAP vaccine candidate [40]. Immunisation of mice with an Rv21 dose as described above (0.5 μg) followed by a challenge with 2,000 transgenic PbANKA-PvCS VK210(r)$_{PbCS}$ sporozoites failed to show protective efficacy (FIG. 7I). However, a 10× increase in the Rv21 dose (5 μg) showed, for the first time in our hands, complete protection in C57BL/6 mice even against a challenge with a higher dose of 5,000 PbANKA-PvCS VK210(r)$_{PbCS}$ sporozoites (FIG. 7I). Rv21 immunization (in Matrix M) induced antibody titres that remained consistently high for up to 70 days and showed a good positive correlation with protection (r=0.54; p=0.0018), while addition of the chaotropic agent urea for the ELISA, indicated that the inclusion of Matrix M adjuvant enhanced antibody avidity, as the addition of urea decreased antibody titres by 26.2% when using adjuvant and 100% in its absence (FIG. 7J). The IgG2a isotype levels were associated with protection (FIG. 7K), while other isotypes (IgM, IgG1, IgG3) were not (data not shown).

Our results indicate that immunization with a chimeric VK210/247 vaccine can induce immunity to the two major strains of *P. vivax*, based on the type of PvCSP central repeats. Moreover, high levels of protective immunity levels can be achieved using a VLP platform in presence of the Matrix-M adjuvant, even in a mouse strain that is difficult to protect against a sporozoite infection.

Example 8: The Effect of Adjuvants and a Combination of Viral Vectors on Rv21 Anti-*Vivax* CSP Immunogenicity BALB/c mice were immunized using two consecutive doses (prime-boost) of Rv21-VLP presenting *vivax* CSP on the surface. The results are shown in FIG. 8. In FIG. 8A, one group received only Rv21 (thin dotted line), while another group received a combination of Rv21+viral vectors expressing TRAP (vvTRAP), consisting of a prime with Rv21+Adenovirus expressing *vivax* TRAP (vvTRAP) and a boost eight weeks later with MVA expressing *vivax* TRAP mixed with Rv21 (black line with squares). Anti-CSP antibodies were significantly higher with the Rv21+vvTRAP immunisation regime. In FIG. 8B, Rv21 was administered twice either alone (Rv21), or mixed with Addavax adjuvant or using a triple combination with Rv21+Addavax+vvTRAP viral vectors. Responses were significantly higher with Addavax or Rv21+Add+vvTRAP compared to Rv21 alone. In FIG. 8C, Rv21 was administered twice either alone (Rv21), or mixed with Matrix M (MM) adjuvant or using a triple combination with Rv21+MM+vvTRAP viral vectors. Responses were significantly higher with MM or Rv21+MM+vvTRAP compared to Rv21 alone.

Example 9: The Effect of Adjuvants and a Combination of Viral Vectors on Rv21 Protective Efficacy Against a Sporozoite Challenge BALB/c mice were immunized using two consecutive doses (prime-boost) of Rv21-VLP presenting *vivax* CSP on the surface, or a combination with Rv21+Adjuvant+ vvTRAP (viral vectors expressing *vivax* TRAP). The results are shown in FIG. 9. In FIG. 9A, the combination of Rv21+vvTRAP+Adjuvants Matrix M (MM) or Addavax (Add) provided 100% of sterile, complete protection against a sporozoite challenge, evidenced as the complete absence of blood stage parasitaemia during 20 days, when naïve mice succumbed to disease on days 5-7. In FIG. 9B, at the suboptimal dose tested, Rv21 afforded 50% protection while the inclusion of adjuvants Addavax (Add) or Matrix M (MM) protected 83.3% and 100% of mice against a sporozoite challenge. In FIG. 9C, a prime/boost with adenovirus-TRAP and MVA-TRAP (vvTRAP) from *vivax* does not confer protection at all, with or without adjuvants. In FIG. 9D, when the *vivax* CSP is administered as a protein (pCS) instead of a VLP composition (Rv21), only 33% of mice are protected but only upon addition of MM adjuvant, compared to 100% of Rv21.

Example 10: A Combination of Rv21+Viral Vectors (vv) Require Both Antigens to be from *Vivax* to Induce Complete Protection Against a Sporozoite Challenge The results of this example are shown in FIG. 10 and in the Table below. In the Table below, mice were vaccinated with a combination of Rv21+viral vectors (vv) in a prime/boost regimen consisting of Rv21+AdenovirusVivaxTRAP for priming and Rv21+MVAVivaxTRAP for boosting (Rv21/vvTRAP); Rv21+AdControl for priming and Rv21+ MVA control for boosting (Rv21/vvControl), where controls express an unrelated *T. cruzi* antigen); R21+AdVivaxTRAP (*falciparum*) for priming and R21+MVAVivaxTRAP (*falciparum*) for boosting (R21 Control/vvTRAP).

| Group | Rv21 μg | Ad TRAP iu | MVA TRAP pfu | R21 μg | Ad Tc24 iu | MVA Tc24 pfu |
|---|---|---|---|---|---|---|
| Rv21/ vvControl | 1 μg | — | — | — | 1 × 10$^8$ | 1 × 10$^7$ |
| R21control/ vvTRAP | — | 1 × 10$^8$ | 1 × 10$^7$ | 1 μg | | |
| Rv21/ vvTRAP | 1 μg | 1 × 10$^8$ | 1 × 10$^7$ | — | — | — |
| naïve | — | — | — | — | — | — |

In FIG. 10, complete, 100% sterile protection against a malaria challenge was achieved with Rv21/vvTRAP, indicating that both antigens need to be from *P. vivax* to induce complete protection. Rv21+vvControl induced only 50% protection while vvTRAP+R21 control did not induce any sterile protection, only a delay in infection.

Example 11: Effect of the Presence of the N-Terminus Region of *P. vivax* CSP on the Protective Efficacy Against a Malaria Sporozoite Challenge Two forms of *P. vivax* CSP were produced: a full version containing the N-terminus, repeats of VK210 and VK247 and C-terminus region (FIG. 11A); and a truncated version without the N-terminus region (FIG. 11B). Proteins were used to immunize mice and a challenge with a transgenic parasite expressing the *vivax* CSP was performed. Protective efficacy was complete when using a truncated form of the protein, whereas the presence of the N-terminus provoked a significant decrease in protection, indicating that the lack of the N-terminus can benefit protective efficacy.

Example 12: Additional Characterization of Rv21 by Western Blot and ELISA

Figure 12A:
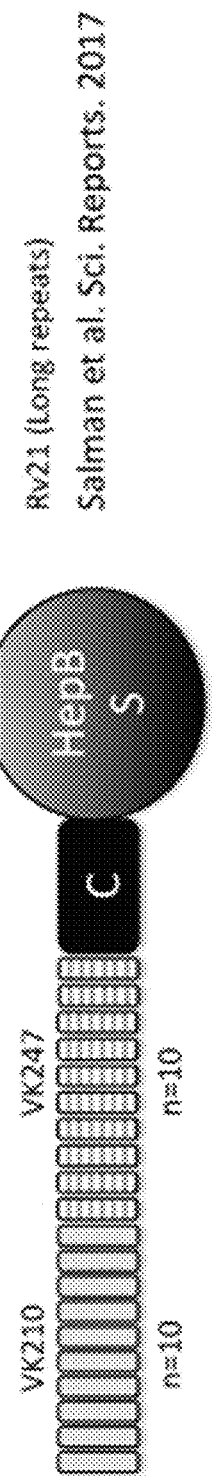
Figure 12C:
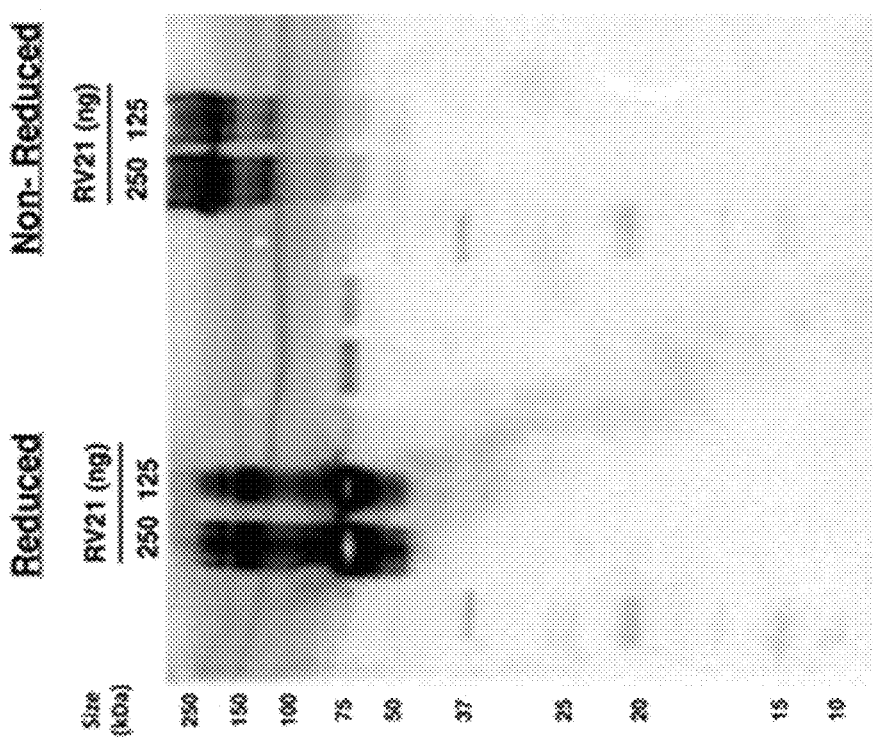
Figure 12B:
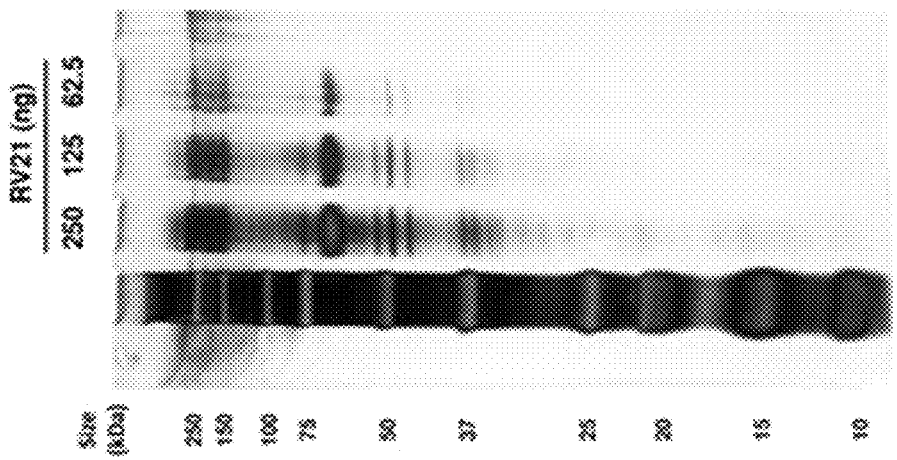
Figure 12D:
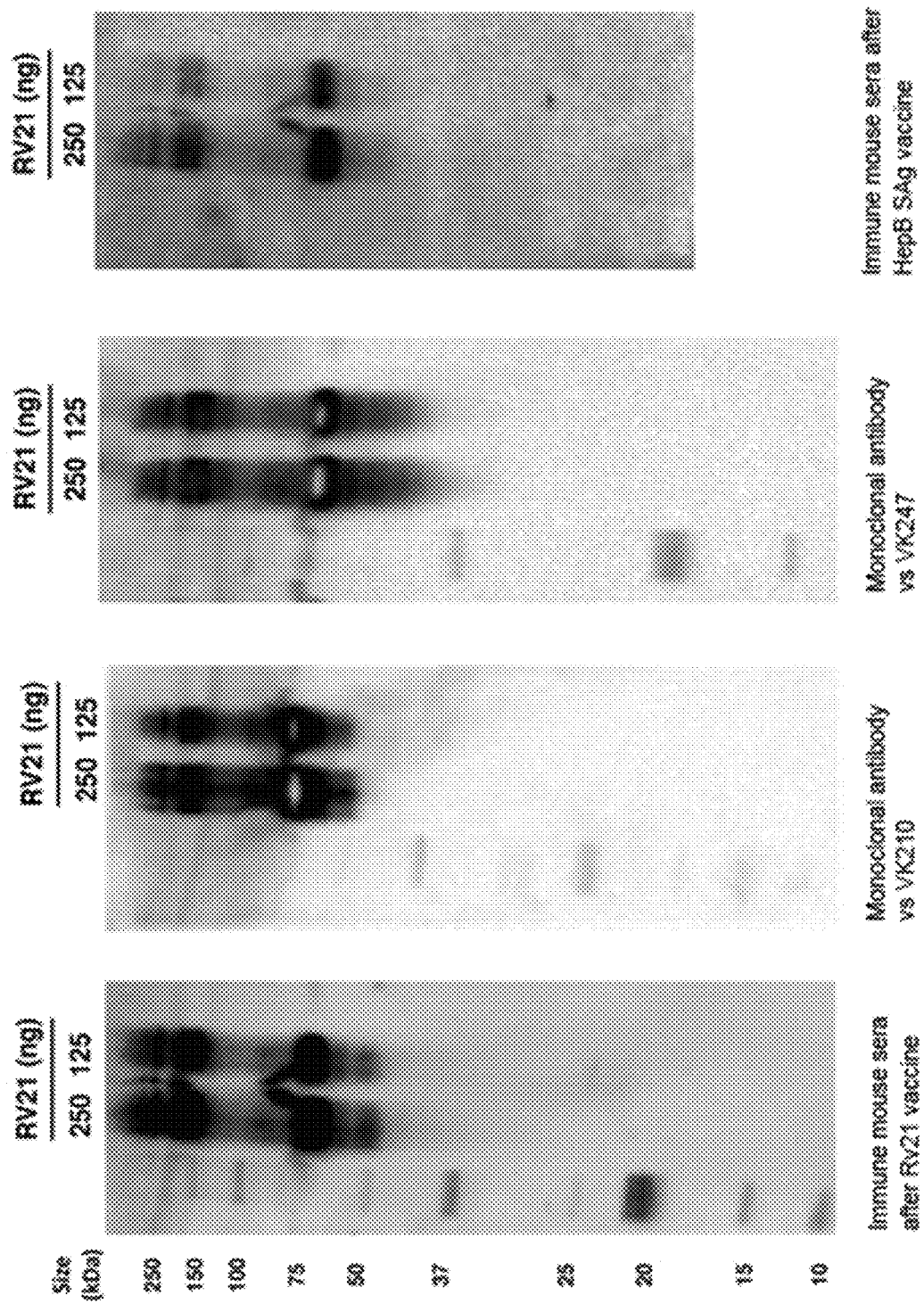
Figure 12E:
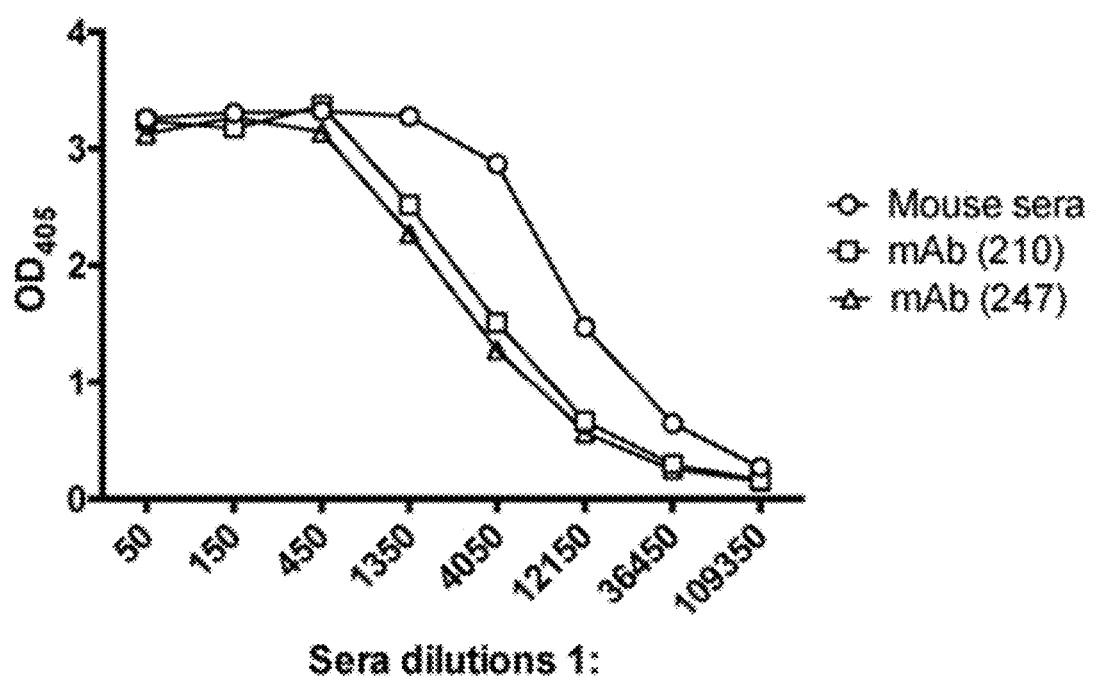

The Rv21 VLP particle (FIG. 12A) was produced in *P. pastoris* yeast, purified by affinity chromatography and a series of western blots were performed for further characterization and confirmation of ability to bind antibodies against *P. vivax* CSP. FIG. 12B shows a PAGE Silver stain under reducing conditions using decreasing amounts of Rv21. FIG. 12C shows a contrast between reducing and non-reducing conditions and binding to a monoclonal antibody against *vivax* CSP VK210 repeats—one of the major circulating strains around the world. FIG. 12D shows recognition of Rv21 by various samples including immune sera from mice previously vaccinated with Rv21 (left), monoclonal anti-PvCSPVK210 (middle left), monoclonal anti-PvCSPVK247 (middle right), and immune mouse sera previously vaccinated with HepB surface Antigen, which is the platform used for Rv21. VK247 corresponds to one of the two major vivax strains circulating around the world, and thus results indicate Rv21 could provide coverage against those two major strains. FIG. 12E shows recognition of Rv21 by monoclonal anti-CSPVK210, anti-CSPVK247 and mouse sera. The latter seems to recognize Rv21 at even lower dilutions, probably due to the presence of both, anti-VK210 and anti-VK247 antibodies.

REFERENCES

1. Guerra, C. A., et al., *The international limits and population at risk of Plasmodium vivax transmission in 2009*. PLoS Negl Trop Dis, 2010. 4(8): p. e774.
2. White, N. J., *Determinants of relapse periodicity in Plasmodium vivax malaria*. Malar J, 2011. 10: p. 297.
3. Markus, M. B., *Malaria: origin of the term "hypnozoite"*. J Hist Biol, 2011. 44(4): p. 781-6.
4. Duffy, P. E., et al., *Pre-erythrocytic malaria vaccines: identifying the targets*. Expert Rev Vaccines, 2012. 11(10): p. 1261-80.
5. Rts, S. C. T. P., *Efficacy and safety of the RTS,S/AS01 malaria vaccine during 18 months after vaccination: a phase 3 randomized, controlled trial in children and young infants at 11 African sites*. PLoS Med, 2014. 11(7): p. e1001685.
6. Almeida, A. P., et al., *Long-lasting humoral and cellular immune responses elicited by immunization with recombinant chimeras of the Plasmodium vivax circumsporozoite protein*. Vaccine, 2014. 32(19): p. 2181-7.
7. Bennett, J. W., et al., *Phase 1/2a Trial of Plasmodium vivax Malaria Vaccine Candidate VMP001/AS01B in Malaria-Naive Adults: Safety, Immunogenicity, and Efficacy*. PLoS Negl Trop Dis, 2016. 10(2): p. e0004423.
8. Lim, C. S., L. Tazi, and F. J. Ayala, *Plasmodium vivax: recent world expansion and genetic identity to Plasmodium simium*. Proc Natl Acad Sci USA, 2005. 102(43): p. 15523-8.
9. Teixeira, L. H., et al., *Immunogenicity of a prime-boost vaccine containing the circumsporozoite proteins of Plasmodium vivax in rodents*. Infect Immun, 2014. 82(2): p. 793-807.
10. Vanloubbeeck, Y., et al., *Comparison of the immune responses induced by soluble and particulate Plasmodium vivax circumsporozoite vaccine candidates formulated in AS01 in rhesus macaques*. Vaccine, 2013. 31(52): p. 6216-24.
11. Yadava, A., et al., *A novel chimeric Plasmodium vivax circumsporozoite protein induces biologically functional antibodies that recognize both VK210 and VK247 sporozoites*. Infect Immun, 2007. 75(3): p. 1177-85.
12. Yadava, A., et al., *Protective efficacy of a Plasmodium vivax circumsporozoite protein-based vaccine in Aotus nancymaae is associated with antibodies to the repeat region*. PLoS Negl Trop Dis, 2014. 8(10): p. e3268.
13. Cespedes, N., et al., *Antigenicity and immunogenicity of a novel Plasmodium vivax circumsporozoite derived synthetic vaccine construct*. Vaccine, 2014. 32(26): p. 3179-86.
14. Cespedes, N., et al., *Antigenicity and immunogenicity of a novel chimeric peptide antigen based on the P. vivax circumsporozoite protein*. Vaccine, 2013. 31(42): p. 4923-30.
15. Udomsangpetch, R., et al., *Short-term in vitro culture of field isolates of Plasmodium vivax using umbilical cord blood*. Parasitol Int, 2007. 56(1): p. 65-9.
16. Targett, G. A., V. S. Moorthy, and G. V. Brown, *Malaria vaccine research and development: the role of the WHO MALVAC committee*. Malar J, 2013. 12: p. 362.
17. Golenda, C. F., J. Li, and R. Rosenberg, *Continuous in vitro propagation of the malaria parasite Plasmodium vivax*. Proc Natl Acad Sci USA, 1997. 94(13): p. 6786-91.
18. Galinski, M. R., et al., *A reticulocyte-binding protein complex of Plasmodium vivax merozoites*. Cell, 1992. 69(7): p. 1213-26.
19. Reyes-Sandoval, A. and M. F. Bachmann, *Plasmodium vivax malaria vaccines: why are we where we are*? Hum Vaccin Immunother, 2013. 9(12): p. 2558-65.
20. Galinski, M. R. and J. W. Barnwell, *Plasmodium vivax: who cares*? Malar J, 2008. 7 Suppl 1: p. S9.
21. Espinosa, D. A., et al., *Development of a chimeric Plasmodium berghei* strain *expressing the repeat region of the P. vivax circumsporozoite protein for in vivo evaluation of vaccine efficacy*. Infect Immun, 2013. 81(8): p. 2882-7.
22. Whitacre, D. C., et al., *P. falciparum and P. vivax Epitope-Focused VLPs Elicit Sterile Immunity to Blood Stage Infections*. PLoS One, 2015. 10(5): p. e0124856.
23. Ewer, K. J., et al., *Protective CD*8+*T-cell immunity to human malaria induced by chimpanzee adenovirus-MVA immunisation*. Nat Commun, 2013. 4: p. 2836.
24. Reyes-Sandoval, A., et al., *Prime-boost immunization with adenoviral and modified vaccinia virus Ankara vectors enhances the durability and polyfunctionality of protective malaria CD*8+*T-cell responses*. Infect Immun, 2010. 78(1): p. 145-53.
25. Reyes-Sandoval, A., et al., *CD*8+*T effector memory cells protect against liver-stage malaria*. J Immunol, 2011. 187(3): p. 1347-57.
26. Heppner, D. G., *The malaria vaccine—status quo* 2013. Travel Med Infect Dis, 2013. 11(1): p. 2-7.
27. Sun, P., et al., *Protective immunity induced with malaria vaccine, RTS,S, is linked to Plasmodium falciparum circumsporozoite protein-specific CD*4+ *and CD*8+ *T cells producing IFN-gamma*. J Immunol, 2003.171(12): p. 6961-7.
28. Moorthy, V. S. and W. R. Ballou, *Immunological mechanisms underlying protection mediated by RTS,S: a review of the available data*. Malar J, 2009. 8: p. 312.
29. Gonzalez-Ceron, L., et al., *Plasmodium vivax: a monoclonal antibody recognizes a circumsporozoite protein precursor on the sporozoite surface*. Exp Parasitol, 1998. 90(3): p. 203-11.
30. Lin, J. W., et al., *A novel 'gene insertion/marker out'* (*GIMO*) *method for transgene expression and gene complementation in rodent malaria parasites*. PLoS One, 2011. 6(12): p. e29289.

31. Longley, R. J., et al., *Comparative assessment of vaccine vectors encoding ten malaria antigens identifies two protective liver-stage candidates.* Sci Rep, 2015. 5: p. 11820.
32. Khan, S. M., et al., *Standardization in generating and reporting genetically modified rodent malaria parasites: the RMgmDB database.* Methods Mol Biol, 2013. 923: p. 139-50.
33. Rosenberg, R., et al., *Circumsporozoite protein heterogeneity in the human malaria parasite Plasmodium vivax.* Science, 1989. 245(4921): p. 973-6.
34. Yoshida, N., et al., *Hybridoma produces protective antibodies directed against the sporozoite stage of malaria parasite.* Science, 1980. 207(4426): p. 71-3.
35. Wang, J. W. and R. B. Roden, *Virus-like particles for the prevention of human papillomavirus-associated malignancies.* Expert Rev Vaccines, 2013. 12(2): p. 129-41.
36. Garcon, N., D. G. Heppner, and J. Cohen, *Development of RTS,S/AS02: a purified subunit-based malaria vaccine candidate formulated with a novel adjuvant.* Expert Rev Vaccines, 2003. 2(2): p. 231-8.
37. Magnusson, S. E., et al., *Immune enhancing properties of the novel Matrix-M adjuvant leads to potentiated immune responses to an influenza vaccine in mice.* Vaccine, 2013. 31(13): p. 1725-33.
38. Reimer, J. M., et al., *Matrix-M adjuvant induces local recruitment, activation and maturation of central immune cells in absence of antigen.* PLoS One, 2012. 7(7): p. e41451.
39. Bengtsson, K. L., et al., *Matrix-M adjuvant: enhancing immune responses by 'setting the stage' for the antigen.* Expert Rev Vaccines, 2013. 12(8): p. 821-3.
40. Bauza, K., et al., *Efficacy of a Plasmodium vivax malaria vaccine using ChAd63 and modified vaccinia Ankara expressing thrombospondin-related anonymous protein as assessed with transgenic Plasmodium berghei parasites.* Infect Immun, 2014. 82(3): p. 1277-86.
41. Herrera, S., G. Corradin, and M. Arevalo-Herrera, *An update on the search for a Plasmodium vivax vaccine.* Trends Parasitol, 2007. 23(3): p. 122-8.
42. Nahrendorf, W., et al., *Memory B-cell and antibody responses induced by Plasmodium falciparum sporozoite immunization.* J Infect Dis, 2014. 210(12): p. 1981-90.
43. Warimwe, G. M., et al., *Peripheral blood monocyte-to-lymphocyte ratio at study enrollment predicts efficacy of the RTS,S malaria vaccine: analysis of pooled phase II clinical trial data.* BMC Med, 2013.11:p. 184.
44. Cabrera-Mora, M., et al., *Induction of Multifunctional Broadly Reactive T Cell Responses by a Plasmodium vivax Circumsporozoite Protein Recombinant Chimera.* Infect Immun, 2015. 83(9): p. 3749-61.
45. Mizutani, M., et al., *Baculovirus-vectored multistage Plasmodium vivax vaccine induces both protective and transmission-blocking immunities against transgenic rodent malaria parasites.* Infect Immun, 2014. 82(10): p. 4348-57.
46. Hodgson, S. H., et al., *Evaluation of the efficacy of ChAd63-MVA vectored vaccines expressing circumsporozoite protein and ME-TRAP against controlled human malaria infection in malaria-naive individuals.* J Infect Dis, 2015. 211(7): p. 1076-86.
47. Magnusson, S. E., et al., *Matrix-M adjuvanted envelope protein vaccine protects against lethal lineage 1 and 2 West Nile virus infection in mice.* Vaccine, 2014. 32(7): p. 800-8.
48. Janse, C. J., B. Franke-Fayard, and A. P. Waters, *Selection by flow-sorting of genetically transformed, GFP-expressing blood stages of the rodent malaria parasite, Plasmodium berghei.* Nat Protoc, 2006. 1(2): p. 614-23.
49. Cox, R. J., et al., *Evaluation of a virosomal H5N1 vaccine formulated with Matrix M adjuvant in a phase I clinical trial.* Vaccine, 2011. 29(45): p. 8049-59.
50. Menard, R. and C. Janse, *Gene targeting in malaria parasites.* Methods, 1997. 13(2): p. 148-57.
51. Orr, R. Y., N. Philip, and A. P. Waters, *Improved negative selection protocol for Plasmodium berghei in the rodent malarial model.* Malar J, 2012. 11: p. 103.
52. Gonzalez-Ceron, L., et al., *Plasmodium vivax: impaired escape of Vk210 phenotype ookinetes from the midgut blood bolus of Anopheles pseudopunctipennis.* Exp Parasitol, 2007. 115(1): p. 59-67.
53. Gantt, S. M., et al., *Cell adhesion to a motif shared by the malaria circumsporozoite protein and thrombospondin is mediated by its glycosaminoglycan-binding region and not by CSVTCG.* J Biol Chem, 1997. 272(31): p. 19205-13.
54. Hernandez-Martinez, M. A., et al., *Antigenic diversity of the Plasmodium vivax circumsporozoite protein in parasite isolates of Western Colombia*. Am J Trop Med Hyg, 2011. 84(2 Suppl): p. 51-7.
55. Miura, K., et al., *Development and characterization of a standardized ELISA including a reference serum on each plate to detect antibodies induced by experimental malaria vaccines*. Vaccine, 2008. 26(2): p. 193-200.
56. Studnicka, G. M., *ELISA assay optimization using hyperbolic regression*. Comput Appl Biosci, 1991. 7(2): p. 217-24.
57. Aricescu, A. R., W. Lu, and E. Y. Jones, *A time- and cost-efficient system for high-level protein production in mammalian cells*. Acta Crystallogr D Biol Crystallogr, 2006. 62(Pt 10): p. 1243-50.
58. Reyes-Sandoval, A., et al., *Potency assays for novel T-cell-inducing vaccines against malaria*. Curr Opin Mol Ther, 2009. 11(1): p. 72-80.
59. Reyes-Sandoval, A., et al., *Single-dose immunogenicity and protective efficacy of simian adenoviral vectors against Plasmodium berghei*. Eur J Immunol, 2008. 38(3): p. 732-41.
60. Shoukat et al., Journal of Infectious Disease 1993, 168:1485-9

ADDITIONAL SEQUENCES

Type I VK210 wild type sequence. *P. vivax* CSP Belem strain
P08677 (ref. sequence from www.uniprot.org)

SEQ ID NO: 1

MKNFILLAVSSILLVDLFPTHCGHNVDLSKAINLNGVNFNNVDASSLGAAHVGQSASRGRGLGENPDDEEGDAKKKK

DGKKAEPKNPRENKLKQPGDRADGQPAGDRADGQPAGDRADGQPAGDRAAGQPAGDRADGQPAGDRADGQPAGDRAD

GQPAGDRADGQPAGDRAAGQPAGDRAAGQPAGDRADGQPAGDRAAGQPAGDRADGQPAGDRAAGQPAGDRADGQPAG

```
DRAAGQPAGDRAAGQPAGDRAAGQPAGDRAAGQPAGNGAGGQAAGGNAGGGQGQNNEGANAPNEKSVKEYLDKVRAT

VGTEWTPCSVTCGVGVRVRRRVNAANKKPEDLTLNDLETDVCTMDKCAGIFNVVSNSLGLVILLVLALFN.
```

Type II VK247 wild type sequence. *P. vivax* CSP PND (Papua New Guinea) strain Q7M3X0 (ref. sequence from www.uniprot.org)

(SEQ ID NO: 2)
```
MKNFILLAVSSILLVDLFPTHCGHNVDLSKAINLNGVGFNNVDASSLGAAHVGQSASRGRGLGENPDDEEGDAKKKK

DGKKAEPKNPRENKLKQPEDGAGNQPGANGAGNQPGANGAGNQPGANGAGDQPGANGAGNQPGANGAGDQPGANGAG

NQPGANGAGNQPGANGAGNQPGANGADDQPGANGAGNQPGANGAGNQPGANGAGNQPGANGAGDQPGANGAGNQPGA

NGAGDQPGANGAGNQPGANGAGNQPGANGAGNQPGANGAGNQPGANGAGGQAAGGNAANKKAGDAGAGQGQNNEGAN

ATNEKSVKEYLDKVRATVGTEWTPCSVTCGVGVRVRRRVNAANKKPEDLTLNDLETDVCTMDKCAGIFNVVSNSLGL

VILLVLALFN
```

Pv VK210 Repeats
DNA Sequence
(SEQ ID NO: 15)
```
GGTGATAGAGCTGCTGGTCAACCTGCTGGTGACAGAGCTGCTGGACAGCCAGCTGGTGATAGAGCTGCTGGTCAGCC

TGCTGGTGATAGAGCTGCTGGACAACCTGCTGGTGATAGAGCTGCTGGTCAACCTGCTGGTGATAGAGCTGACGGTC

AGCCAGCTGGTGATAGAGCTGACGGTCAACCTGCTGGTGACAGAGCTGACGGACAACCTGCTGGTGATAGAGCTGAT

GGACAACCAGCTGGAAATGGTGCTGGTGGTCAAGCTGCT
```

Amino acid sequence
(SEQ ID NO: 16)
```
GDRAAGQPAGDRAAGQPAGDRAAGQPAGDRAAGQPAGDRADGQPAGDRADGQPAGDRADGQPAGDRAD

GQPAGNGAGGQAA
```

Pv VK247 Repeats
DNA Sequence
(SEQ ID NO: 17)
```
GCTAATGGTGCTGGAAATCAACCAGGTGCTAACGGTGCTGGTGGACAGGCTGCTGCTAACGGTGCTGGTAACCAGCC

TGGTGCTAATGGTGCTGGTGGACAAGCTGCTGCTAACGGTGCTGGTGATCAACCAGGTGCTAATGGTGCTGGTGATC

AGCCTGGTGCTAACGGTGCTGATGACCAACCTGGTGCTAACGGTGCTGGTGACCAGCCAGGTGAGGACGGTGCTGGT

AATCAACCTGGTGCTAACGGTGCTGGTGATCAACCTGGT
```

Amino acid sequence
(SEQ ID NO: 18)
```
ANGAGNQPGANGAGGQAAANGAGNQPGANGAGGQAAANGAGDQPGANGAGDQPGANGADDQPGANGAGDQPGEDGAG

NQPGANGAGDQPG
```

*P. vivax*-like repeats Protein ID: UniProtKB-Q26124 (Q26124_9APIC)
Repeat I
DNA Sequence
(SEQ ID NO: 22)
```
gccccaggagcaaatcaggaaggtggagcagcagccccaggagcaaatcaggaaggtggagcagcagccccaggagc aaatcaggaaggtggagcagca
```

Amino acid sequence
(SEQ ID NO: 23)
```
APGANQEGGAAAPGANQEGGAAAPGANQEGGAA
```

*P. vivax*-like repeat II
DNA Sequence
(SEQ ID NO: 24)
```
gcaccaggagcaaaccagggaggtggagcagcagcaccaggagcaaaccagggaggtggagcagcagcaccaggagc aaaccagggaggtggagcagca
```

Amino acid sequence
(SEQ ID NO: 25)
```
APGANQGGGAAAPGANQGGGAAAPGANQGGGAA
```

```
P. vivax-like repeat I + P. vivax-like repeat II
Amino acid sequence
                                                              (SEQ ID NO: 26)
APGANQEGGAAAPGANQEGGAAAPGANQEGGAA

APGANQGGGAAAPGANQGGGAAAPGANQGGGAA

P. vivax-like repeat II + P. vivax-like repeat I
Amino acid sequence
                                                              (SEQ ID NO: 27)
APGANQGGGAAAPGANQGGGAAAPGANQGGGAA

APGANQEGGAAAPGANQEGGAAAPGANQEGGAA

C-Terminus of PvCSP. Protein ID in UNIPROT: UniProtKB-P08677 (CSP_PLAVB)
DNA Sequence
                                                              (SEQ ID NO: 28)
CAAGCTGCTGGTGGTAATGCTGGTGGTGGTCAGGGTCAAAACAACGAGGGTGCTAATGCTCCAAACGAGAAGTCCGT

TAAGGAATACTTGGACAAAGTTAGAGCTACTGTTGGTACTGAGTGGACTCCATGTTCCGTTACTTGTGGTGTTGGTG

TTAGAGTTAGAAGAAGAGTTAACGCTGCTAACAAGAAGCCAGAGGACTTGACTTTGAACGACTTGGAGACTGACGTT

TGTACTATGGACAAG

Protein Sequence
                                                              (SEQ ID NO: 29)
QAAGGNAGGGQGQNNEGANAPNEKSVKEYLDKVRATVGTEWTPCSVTCGVGVRVRRRVNAANKKPEDLTLNDLETDV

CTMDK

C-Terminus fragment of PvCSP
Amino acid sequence
                                                              (SEQ ID NO: 30)
EWTPCSVTCGVGVRVRRRVNAANKKPEDLTLNDLETDVCTMDK N-terminus sequence from PvCSP in Adenovirus.
Gene ID PVX_187290. Plasmodium vivax (strain Salvador I),
UNIPROT UniProtKB-A5KDP2 (A5KDP2_PLAVS)
DNA Sequence
                                                              (SEQ ID NO: 34)
ACCCACTGCGGCCACAACGTGGACCTGAGCAAGGCCATCAACCTGAACGGCGTGAACTTCAACAATGTGGACGCCTC

TAGCCTGGGAGCTGCTCACGTGGGCCAGAGCGCCAGCAGAGGCAGAGGCCTGGGCGAGAACCCCGACGATGAGGAAG

GCGACGCCAAGAAGAAGAAGGACGGCAAGAAGGCCGAGCCCAAGAACCCCAGAGAGAACAAGCTGAAGCAGCCC

Amino acid sequence
                                                              (SEQ ID NO: 35)
THCGHNVDLSKAINLNGVNFNNVDASSLGAAHVGQSASRGRGLGENPDDEEGDAKKKKDGKKAEPKNPRENKLKQP Hepatitis B S Antigen
DNA sequence
                                                              (SEQ ID NO: 37)
CCAGTTACTAATATGGAAAACATCACTTCCGGTTTCTTGGGTCCTTTGTTGGTTTTGCAGGCTGGATTCTTCTTGTT

GACTAGAATCTTGACTATCCCACAGTCCTTGGACTCTTGGTGGACTTCCTTGAACTTCTTGGGTGGTTCCCCAGTTT

GTTTGGGTCAGAACTCTCAATCCCCAACTTCTAACCACTCCCCAACATCCTGTCCTCCAATTTGTCCAGGTTACAGA

TGGATGTGTTTGAGAAGATTCATCATTTTCTTGTTCATCTTGTTGTTGTGTTTGATCTTCTTGTTGGTTTTGTTGGA

CTACCAGGGTATGTTGCCAGTTTGTCCATTGATCCCAGGTTCCACTACTACAAACACTGGTCCATGTAAGACTTGTA

CTACTCCAGCTCAGGGTAACTCTATGTTCCCTTCCTGTTGTTGTACTAAGCCAACTGACGGTAACTGTACTTGTATC

CCAATTCCATCCTCCTGGGCTTTCGCTAAGTACTTGTGGGAATGGGCTTCCGTTAGATTCTCTTGGTTGTCCTTGTT

GGTTCCATTCGTTCAGTGGTTCGTTGGTTTGTCCCCAACTGTTTGGTTGTCTGCTATCTGGATGATGTGGTACTGGG

GTCCATCCTTGTACTCTATCGTTTCCCCATTCATCCCTTTGTTGCCAATCTTCTTCTGTTTGTGGGTTTACATC

Amino acid sequence
                                                              (SEQ ID NO: 38)
PVTNMENITSGFLGPLLVLQAGFFLLTRILTIPQSLDSWWTSLNFLGGSPVCLGQNSQSPTSNHSPTSCPPICPGYR

WMCLRRFIIFLFILLLCLIFLLVLLDYQGMLPVCPLIPGSTTTNTGPCKTCTTPAQGNSMFPSCCCTKPTDGNCTCI

PIPSSWAFAKYLWEWASVRFSWLSLLVPFVQWFVGLSPTVWLSAIWMMWYGPSLYSIVSPFIPLLPIFFCLWVYI
```

Preferred Rv21 sequence
Amino acid sequence (SEQ ID NO: 39 (SEQ ID NOs: 16 + 18 + 29 + 38))

GDRAAGQPAGDRAAGQPAGDRAAGQPAGDRAAGQPAGDRAAGQPAGDRADGQPAGDRADGQPAGDRADGQPAGDRADG

QPAGNGAGGQAAANGAGNQPGANGAGGQAAANGAGNQPGANGAGGQAAANGAGDQPGANGAGDQPGANGADDQPGANG

AGDQPGEDGAGNQPGANGAGDQPGQAAGGNAGGGQGQNNEGANAPNEKSVKEYLDKVRATVGTEWTPCSVTCGVGVRV

RRRVNAANKKPEDLTLNDLETDVCTMDKPVTNMENITSGFLGPLLVLQAGFFLLTRILTIPQSLDSWWTSLNFLGGSP

VCLGQNSQSPTSNHSPTSCPPICPGYRWMCLRRFIIFLFILLLCLIFLLVLLDYQGMLPVCPLIPGSTTTNTGPCKTC

TTPAQGNSMFPSCCCTKPTDGNCTCIPIPSSWAFAKYLWEWASVRFSWLSLLVPFVQWFVGLSPTVWLSAIWMMWYWG

PSLYSIVSPFIPLLPIFFCLWVYI

PvTRAP sequence from SalI strain of *P. vivax* (wild-type)
Protein sequence (SEQ ID NO: 40)

MKLLQNKSYLLVVFLLYVSIFARGDEKVVDEVKYSEEVCNESVD

LYLLVDGSGSIGYPNWITKVIPMLNGLINSLSLSRDTINLYMNLFGNYTTELIRLGSG

QSIDKRQALSKVTELRKTYTPYGTTNMTAALDEVQKHLNDRVNREKAIQLVILMTDGV

PNSKYRALEVANKLKQRNVSLAVIGIGQGINHQFNRLIAGCRPREPNCKFYSYADWNE

AVALIKPFIAKVCTEVERVANCGPWDPWTACSVTCGRGTHSRSRPSLHEKCTTHMVSE

CEEGECPVEPEPLPVPAPLPTVPEDVNPRDTDDENENPNFNKGLDVPDEDDDEVPPAN

ERADGNPVEENVFPPADDSVPDESNVLPLPPAVPGGSSEEFPADVQNNPDSPEELPME

QEVPQDNNVNEPERSDSKGYGVNEKVIPNPLDNERDMANKNKTVHPGRKDSARDRYAR

PHGSTHVNNNRANENSDIPNNPVPSDYEQPEDKAKKSSNNGYKIAGGVIAGLALVGCV

GFAYNFVAGGGAAGMAGEPAPFDEAMAEDEKDVAEADQFKLPEDNEWN

PvTRAP variant sequence
Protein sequence (SEQ ID NO: 41)

DEKVVDEVKYSEEVCNESVDLYLLVDGSGSIGYPNWITKVIPMLNGLINSLSLSRDTINLYMNLFGNYTTELIRLGS

GQSIDKRQALSKVTELRKTYTPYGTTNMTAALDEVQKHLNDRVNREKAIQLVILMTDGVPNSKYRALEVANKLKQRN

VSLAVIGVGQGINHQFNRLIAGCRPREPNCKFYSYADWNEAVALIKPFIAKVCTEVERVANCGPWDPWTACSVTCGR

GTHSRSRPSLHEKCTTHMVSECEEGECPVEPEPLPVPAPLPTVPEDVNPRDTDDENENPNFNKGLDVPDEDDDEVPP

ANEGADGNPVEENVFPPADDSVPDESNVLPLPPAVPGGSSEEFPADVQNNPDSPEELPMEQEVPQDNNVNEPERSDS

NGYGVNEKVIPNPLDNERDMANKNKTVHPGRKDSARDRYARPHGSTHVNNNRANENSDIPNNPVPSDYEQPEDKAKK

SSNNGYK

C-tag
DNA sequence (SEQ ID NO: 42)

GAGCCCGAGGCC

Amino acid sequence (SEQ ID NO: 43)

EPEA

Pvs25
DNA sequence (SEQ ID NO: 44)

ATGgccgtcacggtagacaccatatgcaaaaatggacagctggttcaaatgagtaaccactttaagtgtatgtgtaa cgaagggctggtgcacctttccgaaaatacatgtgaagaaaaaaatgaatgcaagaaagaaaccctaggcaaagcat gcggggaatttggccagtgtatagaaaacccagacccagcacaggtaaacatgtacaaatgtggttgcattgagggc tacactttgaaggaagacacttgtgtgcttgatgtatgtcaatacaaaaattgtggagaaagtggcgaatgcattgt tgagtacctctcggaaatccaaagtgcaggttgctcatgtgctattggcaaagtccccaatccagaagatgagaaaa aatgtaccaaaacgggagaaactgcttgtcaattgaaatgtaacacagataatgaagtctgcaaaaatgttgaagga

```
gtttacaagtgccagtgtatggaaggctttacgttcgacaaagagaaaaatgtatgcctttcctattctgtatttaa catcctaaactactccctcttctttatcatcctgcttgtcctttcgtacgtcatataa
```

Pvs25
Amino acid sequence (SEQ ID NO: 45)

MAVTVDTICKNGQLVQMSNHFKCMCNEGLVHLSENTCEEKNECKKETLGKACGEFGQCIENPDPAQVNMYKCGCIEG

YTLKEDTCVLDVCQYKNCGESGECIVEYLSEIQSAGCSCAIGKVPNPEDEKKCTKTGETACQLKCNTDNEVCKNVEG

VYKCQCMEGFTFDKEKNVCLSYSVFNILNYSLFFIILLVLSYVI

Pvs28
Amino acid sequence (SEQ ID NO: 46)

```
                    MKVTAETQC KNGYVVQMSN HFECKCNDGF
                            80         90        100

VMANENTCEE KRDCTNPQNV NKNCGDYAVC ANTRMNDEER ALRCGCILGY
       110        120        130        140        150

TVMNEVCTPN KCNGVLCGKG KCILDPANVN STMCSCNIGT TLDESKKCGK
       160        170        180        190        200

PGKTECTLKC KANEECKETQ NYYKCVAKGS GGEGSGGEGS GGEGSGGEGS
       210        220        230

GGEGSGGDTG AAYSLMNGSA VISILLVFAF FMMSLV
```

Pvs25 + Pvs28 fusion
Amino acid sequence (SEQ ID NO: 47)

MAVTVDTICKNGQLVQMSNHFKCMCNEGLVHLSENTCEEKNECKKETLGKACGEFGQCIENPDPAQVNMYKCGCIEG

YTLKEDTCVLDVCQYKNCGESGECIVEYLSEIQSAGCSCAIGKVPNPEDEKKCTKTGETACQLKCNTDNEVCKNVEG

VYKCQCMEGFTFDKEKNVCLSYSVFNILNYSLFFIILLVLSYVIKVTAETQCKNGYVVQMSNHFECKCNDGFVMANE

NTCEEKRDCTNPQNVNKNCGDYAVCANTRMNDEERALRCGCILGYTVMNEVCTPNKCNGVLCGKGKCILDPANVNST

MCSCNIGTTLDESKKCGKPGKTECTLKCKANEECKETQNYYKCVAKGSGGEGSGGEGSGGEGSGGEGSGGEGSGGDT

GAAYSLMNGSAVISILLVFAFFMMSLV

---

The invention claimed is:

1. A fusion polypeptide or a particle comprising the fusion polypeptide, wherein the fusion polypeptide comprises:
   (i) 8-12 repeat units derived from the repeating region of a Type I circumsporozoite protein (CSP) of *Plasmodium vivax*,
   wherein the repeat units have amino acid sequences independently selected from the group consisting of:

GDRAAGQPA  (SEQ ID NO: 3)

GDRADGQPA  (SEQ ID NO: 4)
   and

GNGAGGQAA;  (SEQ ID NO: 5)

(ii) 8-12 repeat units derived from the repeating region of a Type II circumsporozoite protein (CSP) of *Plasmodium vivax*,
   wherein the repeat units have amino acid sequences independently selected from the group consisting of:

ANGAGNQPG  (SEQ ID NO: 6)

ANGAGGQAA  (SEQ ID NO: 7)

ANGAGDQPG  (SEQ ID NO: 8)

ANGADDQPG  (SEQ ID NO: 9)
   and

EDGAGNQPG;  (SEQ ID NO: 10)

and
   (iii) an amino acid sequence derived from the C-terminal fragment of CSP of *Plasmodium vivax*; and optionally
   (iv) an amino acid sequence derived from the Hepatitis B virus surface antigen.

2. The fusion polypeptide or particle as claimed in claim 1, wherein the (i) 8-12 repeat units derived from the repeating region of a Type I circumsporozoite protein (CSP) of *Plasmodium vivax* comprise:
   (a) 5 blocks of the repeat unit GDRAAGQPA (SEQ ID NO: 3);
   (b) 4 blocks of the repeat unit GDRADGQPA (SEQ ID NO: 4); and
   (c) 1 block of the repeat unit GNGAGGQAA (SEQ ID NO: 5).

3. The fusion polypeptide or particle as claimed in claim 1, wherein the (ii) 8-12 repeat units derived from the repeating region of a Type II circumsporozoite protein (CSP) of *Plasmodium vivax* comprise:
   (a) 2 blocks of the repeat unit pair ANGAGNQPG-ANGAGGQAA (SEQ ID NO: 11);
   (b) 1 block of the repeat unit pair ANGAGDQPG-ANGAGDQPG (SEQ ID NO: 12);
   (c) 1 block of the repeat unit pair ANGADDQPG-ANGAGDQPG (SEQ ID NO: 13); and
   (d) 1 block of the repeat unit pair EDGAGNQPG-ANGAGDQPG (SEQ ID NO: 14).

4. The fusion polypeptide or particle as claimed in claim 1, wherein the amino acid sequence of (i) is:
   (a) a sequence having at least 80% sequence identity to SEQ ID NO: 16 and having the ability to induce protective immunity against *P. vivax* CSP; or
   (b) a fragment of SEQ ID NO: 16 which is at least 50% of the length of SEQ ID NO: 16 and having the ability to induce protective immunity against *P. vivax* CSP;
and/or
   wherein the amino acid sequence of (ii) is:
   (a) a sequence having at least 80% sequence identity to SEQ ID NO: 18 and having the ability to induce protective immunity against *P. vivax* CSP; or
   (b) a fragment of SEQ ID NO: 18 which is at least 50% of the length of SEQ ID NO: 18 and having the ability to induce protective immunity against *P. vivax* CSP.

5. The fusion polypeptide or particle as claimed in claim 1, wherein the fusion polypeptide additionally comprises:
   (v) at least one repeat unit derived from the repeating region of a circumsporozoite protein (CSP) of a *Plasmodium vivax*-like malaria parasite, wherein the amino acid sequence of the at least one repeat unit is APGANQ(E/G)GGAA (SEQ ID NO: 19).

6. The fusion polypeptide or particle as claimed in claim 1, wherein the amino acid sequence derived from the C-terminal fragment of CSP of *P. vivax* is:
   (a) an amino acid sequence having at least 80% sequence identity to one or more of SEQ ID NOs: 29-32 and comprising one or more T-cell epitopes which promote the immunogenicity of the Type I and/or Type II repeat units; or
   (b) a fragment of SEQ ID NOs: 29-32 which is at least 50% of the length of SEQ ID NOs: 29-32 and comprises one or more T-cell epitopes which promote the immunogenicity of the Type I and/or Type II repeat units,
and/or
wherein the amino acid sequence derived from the Hepatitis B virus surface antigen is:
   (a) an amino acid sequence having at least 80% sequence identity to SEQ ID NO: 38 and having the ability to increase the immunogenicity of parts (i)-(iii) of the fusion polypeptide of claim 1; or (b) a fragment of SEQ ID NO: 38 which is at least 80% of the length of SEQ ID NO: 38 and having the ability to increase the immunogenicity of parts (i)-(iii) of the fusion polypeptide of claim 1.

7. A pharmaceutical composition comprising a particle or fusion polypeptide as claimed in claim 1 and/or a vector or plasmid comprising a nucleic acid which codes for the particle or fusion polypeptide, optionally together with one or more pharmaceutically-acceptable carriers, excipients or diluents.

8. A vaccine composition comprising a particle or fusion polypeptide as claimed in claim 1, and/or a vector or plasmid comprising a nucleic acid which codes for the particle or fusion polypeptide, together with a pharmaceutically-acceptable adjuvant.

* * * * *

SEQUENCE LISTING

<160> NUMBER OF SEQ ID NOS: 53

<210> SEQ ID NO 1
<211> LENGTH: 378
<212> TYPE: PRT
<213> ORGANISM: Plasmodium vivax

<400> SEQUENCE: 1

```
Met Lys Asn Phe Ile Leu Leu Ala Val Ser Ser Ile Leu Leu Val Asp
1               5                   10                  15

Leu Phe Pro Thr His Cys Gly His Asn Val Asp Leu Ser Lys Ala Ile
                20                  25                  30

Asn Leu Asn Gly Val Asn Phe Asn Asn Val Asp Ala Ser Ser Leu Gly
            35                  40                  45

Ala Ala His Val Gly Gln Ser Ala Ser Arg Gly Arg Gly Leu Gly Glu
        50                  55                  60

Asn Pro Asp Asp Glu Glu Gly Asp Ala Lys Lys Lys Asp Gly Lys
65                  70                  75                  80

Lys Ala Glu Pro Lys Asn Pro Arg Glu Asn Lys Leu Lys Gln Pro Gly
                85                  90                  95

Asp Arg Ala Asp Gly Gln Pro Ala Gly Asp Arg Ala Asp Gly Gln Pro
            100                 105                 110
```

-continued

Ala Gly Asp Arg Ala Asp Gly Gln Pro Ala Gly Asp Arg Ala Ala Gly
            115                 120                 125

Gln Pro Ala Gly Asp Arg Ala Asp Gly Gln Pro Ala Gly Asp Arg Ala
130                 135                 140

Asp Gly Gln Pro Ala Gly Asp Arg Ala Asp Gly Gln Pro Ala Gly Asp
145                 150                 155                 160

Arg Ala Asp Gly Gln Pro Ala Gly Asp Arg Ala Ala Gly Gln Pro Ala
                165                 170                 175

Gly Asp Arg Ala Ala Gly Gln Pro Ala Gly Asp Arg Ala Asp Gly Gln
            180                 185                 190

Pro Ala Gly Asp Arg Ala Ala Gly Gln Pro Ala Gly Asp Arg Ala Asp
        195                 200                 205

Gly Gln Pro Ala Gly Asp Arg Ala Ala Gly Gln Pro Ala Gly Asp Arg
    210                 215                 220

Ala Asp Gly Gln Pro Ala Gly Asp Arg Ala Ala Gly Gln Pro Ala Gly
225                 230                 235                 240

Asp Arg Ala Ala Gly Gln Pro Ala Gly Asp Arg Ala Ala Gly Gln Pro
                245                 250                 255

Ala Gly Asp Arg Ala Ala Gly Gln Pro Ala Gly Asn Gly Ala Gly Gly
            260                 265                 270

Gln Ala Ala Gly Gly Asn Ala Gly Gly Gln Gly Gln Asn Asn Glu
        275                 280                 285

Gly Ala Asn Ala Pro Asn Glu Lys Ser Val Lys Glu Tyr Leu Asp Lys
    290                 295                 300

Val Arg Ala Thr Val Gly Thr Glu Trp Thr Pro Cys Ser Val Thr Cys
305                 310                 315                 320

Gly Val Gly Val Arg Val Arg Arg Val Asn Ala Ala Asn Lys Lys
                325                 330                 335

Pro Glu Asp Leu Thr Leu Asn Asp Leu Glu Thr Asp Val Cys Thr Met
            340                 345                 350

Asp Lys Cys Ala Gly Ile Phe Asn Val Val Ser Asn Ser Leu Gly Leu
        355                 360                 365

Val Ile Leu Leu Val Leu Ala Leu Phe Asn
    370                 375

<210> SEQ ID NO 2
<211> LENGTH: 395
<212> TYPE: PRT
<213> ORGANISM: Plasmodium vivax

<400> SEQUENCE: 2

Met Lys Asn Phe Ile Leu Leu Ala Val Ser Ser Ile Leu Leu Val Asp
1               5                   10                  15

Leu Phe Pro Thr His Cys Gly His Asn Val Asp Leu Ser Lys Ala Ile
            20                  25                  30

Asn Leu Asn Gly Val Gly Phe Asn Asn Val Asp Ala Ser Ser Leu Gly
        35                  40                  45

Ala Ala His Val Gly Gln Ser Ala Ser Arg Gly Arg Gly Leu Gly Glu
    50                  55                  60

Asn Pro Asp Asp Glu Glu Gly Asp Ala Lys Lys Lys Asp Gly Lys
65                  70                  75                  80

Lys Ala Glu Pro Lys Asn Pro Arg Glu Asn Lys Leu Lys Gln Pro Glu
                85                  90                  95

Asp Gly Ala Gly Asn Gln Pro Gly Ala Asn Gly Ala Gly Asn Gln Pro
            100                 105                 110

-continued

Gly Ala Asn Gly Ala Gly Asn Gln Pro Gly Ala Asn Gly Ala Gly Asp
            115                 120                 125

Gln Pro Gly Ala Asn Gly Ala Gly Asn Gln Pro Gly Ala Asn Gly Ala
        130                 135                 140

Gly Asp Gln Pro Gly Ala Asn Gly Ala Gly Asn Gln Pro Gly Ala Asn
145                 150                 155                 160

Gly Ala Gly Asn Gln Pro Gly Ala Asn Gly Ala Gly Asn Gln Pro Gly
            165                 170                 175

Ala Asn Gly Ala Asp Asp Gln Pro Gly Ala Asn Gly Ala Gly Asn Gln
            180                 185                 190

Pro Gly Ala Asn Gly Ala Gly Asn Gln Pro Gly Ala Asn Gly Ala Gly
            195                 200                 205

Asn Gln Pro Gly Ala Asn Gly Ala Gly Asp Gln Pro Gly Ala Asn Gly
        210                 215                 220

Ala Gly Asn Gln Pro Gly Ala Asn Gly Ala Gly Asp Gln Pro Gly Ala
225                 230                 235                 240

Asn Gly Ala Gly Asn Gln Pro Gly Ala Asn Gly Ala Gly Asn Gln Pro
            245                 250                 255

Gly Ala Asn Gly Ala Gly Asn Gln Pro Gly Ala Asn Gly Ala Gly Asn
            260                 265                 270

Gln Pro Gly Ala Asn Gly Ala Gly Gly Gln Ala Gly Gly Asn Ala
        275                 280                 285

Ala Asn Lys Lys Ala Gly Asp Ala Gly Ala Gly Gln Gly Gln Asn Asn
            290                 295                 300

Glu Gly Ala Asn Ala Thr Asn Glu Lys Ser Val Lys Glu Tyr Leu Asp
305                 310                 315                 320

Lys Val Arg Ala Thr Val Gly Thr Glu Trp Thr Pro Cys Ser Val Thr
            325                 330                 335

Cys Gly Val Gly Val Arg Val Arg Arg Arg Val Asn Ala Ala Asn Lys
            340                 345                 350

Lys Pro Glu Asp Leu Thr Leu Asn Asp Leu Glu Thr Asp Val Cys Thr
        355                 360                 365

Met Asp Lys Cys Ala Gly Ile Phe Asn Val Val Ser Asn Ser Leu Gly
        370                 375                 380

Leu Val Ile Leu Leu Val Leu Ala Leu Phe Asn
385                 390                 395

<210> SEQ ID NO 3
<211> LENGTH: 9
<212> TYPE: PRT
<213> ORGANISM: Plasmodium vivax

<400> SEQUENCE: 3

Gly Asp Arg Ala Ala Gly Gln Pro Ala
1               5

<210> SEQ ID NO 4
<211> LENGTH: 9
<212> TYPE: PRT
<213> ORGANISM: Plasmodium vivax

<400> SEQUENCE: 4

Gly Asp Arg Ala Asp Gly Gln Pro Ala
1               5

<210> SEQ ID NO 5

```
<211> LENGTH: 9
<212> TYPE: PRT
<213> ORGANISM: Plasmodium vivax

<400> SEQUENCE: 5

Gly Asn Gly Ala Gly Gly Gln Ala Ala
1               5

<210> SEQ ID NO 6
<211> LENGTH: 9
<212> TYPE: PRT
<213> ORGANISM: Plasmodium vivax

<400> SEQUENCE: 6

Ala Asn Gly Ala Gly Asn Gln Pro Gly
1               5

<210> SEQ ID NO 7
<211> LENGTH: 9
<212> TYPE: PRT
<213> ORGANISM: Plasmodium vivax

<400> SEQUENCE: 7

Ala Asn Gly Ala Gly Gly Gln Ala Ala
1               5

<210> SEQ ID NO 8
<211> LENGTH: 9
<212> TYPE: PRT
<213> ORGANISM: Plasmodium vivax

<400> SEQUENCE: 8

Ala Asn Gly Ala Gly Asp Gln Pro Gly
1               5

<210> SEQ ID NO 9
<211> LENGTH: 9
<212> TYPE: PRT
<213> ORGANISM: Plasmodium vivax

<400> SEQUENCE: 9

Ala Asn Gly Ala Asp Asp Gln Pro Gly
1               5

<210> SEQ ID NO 10
<211> LENGTH: 9
<212> TYPE: PRT
<213> ORGANISM: Plasmodium vivax

<400> SEQUENCE: 10

Glu Asp Gly Ala Gly Asn Gln Pro Gly
1               5

<210> SEQ ID NO 11
<211> LENGTH: 18
<212> TYPE: PRT
<213> ORGANISM: Plasmodium vivax

<400> SEQUENCE: 11

Ala Asn Gly Ala Gly Asn Gln Pro Gly Ala Asn Gly Ala Gly Gly Gln
1               5                   10                  15

Ala Ala

<210> SEQ ID NO 12
```

-continued

```
<211> LENGTH: 18
<212> TYPE: PRT
<213> ORGANISM: Plasmodium vivax

<400> SEQUENCE: 12

Ala Asn Gly Ala Gly Asp Gln Pro Gly Ala Asn Gly Ala Gly Asp Gln
1               5                   10                  15

Pro Gly

<210> SEQ ID NO 13
<211> LENGTH: 18
<212> TYPE: PRT
<213> ORGANISM: Plasmodium vivax

<400> SEQUENCE: 13

Ala Asn Gly Ala Asp Asp Gln Pro Gly Ala Asn Gly Ala Gly Asp Gln
1               5                   10                  15

Pro Gly

<210> SEQ ID NO 14
<211> LENGTH: 18
<212> TYPE: PRT
<213> ORGANISM: Plasmodium vivax

<400> SEQUENCE: 14

Glu Asp Gly Ala Gly Asn Gln Pro Gly Ala Asn Gly Ala Gly Asp Gln
1               5                   10                  15

Pro Gly

<210> SEQ ID NO 15
<211> LENGTH: 270
<212> TYPE: DNA
<213> ORGANISM: Plasmodium vivax

<400> SEQUENCE: 15
ggtgatagag ctgctggtca acctgctggt gacagagctg ctggacagcc agctggtgat      60
agagctgctg gtcagcctgc tggtgataga gctgctggac aacctgctgg tgatagagct     120
gctggtcaac ctgctggtga tagagctgac ggtcagccag ctggtgatag agctgacggt     180
caacctgctg gtgacagagc tgacggacaa cctgctggtg atagagctga tggacaacca     240
gctggaaatg gtgctggtgg tcaagctgct                                      270

<210> SEQ ID NO 16
<211> LENGTH: 90
<212> TYPE: PRT
<213> ORGANISM: Plasmodium vivax

<400> SEQUENCE: 16

Gly Asp Arg Ala Ala Gly Gln Pro Ala Gly Asp Arg Ala Ala Gly Gln
1               5                   10                  15

Pro Ala Gly Asp Arg Ala Ala Gly Gln Pro Ala Gly Asp Arg Ala Ala
            20                  25                  30

Gly Gln Pro Ala Gly Asp Arg Ala Ala Gly Gln Pro Ala Gly Asp Arg
        35                  40                  45

Ala Asp Gly Gln Pro Ala Gly Asp Arg Ala Asp Gly Gln Pro Ala Gly
    50                  55                  60

Asp Arg Ala Asp Gly Gln Pro Ala Gly Asp Arg Ala Asp Gly Gln Pro
65                  70                  75                  80

Ala Gly Asn Gly Ala Gly Gly Gln Ala Ala
```

<210> SEQ ID NO 17
<211> LENGTH: 270
<212> TYPE: DNA
<213> ORGANISM: Plasmodium vivax

<400> SEQUENCE: 17

```
gctaatggtg ctggaaatca accaggtgct aacggtgctg gtggacaggc tgctgctaac    60
ggtgctggta accagcctgg tgctaatggt gctggtggac aagctgctgc taacggtgct   120
ggtgatcaac caggtgctaa tggtgctggt gatcagcctg gtgctaacgg tgctgatgac   180
caacctggtg ctaacggtgc tggtgaccag ccaggtgagg acggtgctgg taatcaacct   240
ggtgctaacg tgctggtga tcaacctggt                                      270
```

<210> SEQ ID NO 18
<211> LENGTH: 90
<212> TYPE: PRT
<213> ORGANISM: Plasmodium vivax

<400> SEQUENCE: 18

```
Ala Asn Gly Ala Gly Asn Gln Pro Gly Ala Asn Gly Ala Gly Gly Gln
1               5                   10                  15
Ala Ala Ala Asn Gly Ala Gly Asn Gln Pro Gly Ala Asn Gly Ala Gly
            20                  25                  30
Gly Gln Ala Ala Ala Asn Gly Ala Gly Asp Gln Pro Gly Ala Asn Gly
        35                  40                  45
Ala Gly Asp Gln Pro Gly Ala Asn Gly Ala Asp Gln Pro Gly Ala
    50                  55                  60
Asn Gly Ala Gly Asp Gln Pro Gly Glu Asp Gly Ala Gly Asn Gln Pro
65                  70                  75                  80
Gly Ala Asn Gly Ala Gly Asp Gln Pro Gly
                85                  90
```

<210> SEQ ID NO 19
<211> LENGTH: 11
<212> TYPE: PRT
<213> ORGANISM: Plasmodium vivax
<220> FEATURE:
<221> NAME/KEY: Xaa
<222> LOCATION: (7)..(7)
<223> OTHER INFORMATION: Where Xaa can be glutamate/glutamic acid or glycine

<400> SEQUENCE: 19

```
Ala Pro Gly Ala Asn Gln Xaa Gly Gly Ala Ala
1               5                   10
```

<210> SEQ ID NO 20
<211> LENGTH: 11
<212> TYPE: PRT
<213> ORGANISM: Plasmodium vivax

<400> SEQUENCE: 20

```
Ala Pro Gly Ala Asn Gln Glu Gly Gly Ala Ala
1               5                   10
```

<210> SEQ ID NO 21
<211> LENGTH: 11
<212> TYPE: PRT
<213> ORGANISM: Plasmodium vivax -continued

<400> SEQUENCE: 21

Ala Pro Gly Ala Asn Gln Gly Gly Gly Ala Ala
1               5                   10

<210> SEQ ID NO 22
<211> LENGTH: 99
<212> TYPE: DNA
<213> ORGANISM: Plasmodium vivax

<400> SEQUENCE: 22
gccccaggag caaatcagga aggtggagca gcagcccag gagcaaatca ggaaggtgga      60
gcagcagccc caggagcaaa tcaggaaggt ggagcagca                           99

<210> SEQ ID NO 23
<211> LENGTH: 33
<212> TYPE: PRT
<213> ORGANISM: Plasmodium vivax

<400> SEQUENCE: 23

Ala Pro Gly Ala Asn Gln Glu Gly Gly Ala Ala Ala Pro Gly Ala Asn
1               5                   10                  15

Gln Glu Gly Gly Ala Ala Ala Pro Gly Ala Asn Gln Glu Gly Gly Ala
            20                  25                  30

Ala

<210> SEQ ID NO 24
<211> LENGTH: 99
<212> TYPE: DNA
<213> ORGANISM: Plasmodium vivax

<400> SEQUENCE: 24
gcaccaggag caaaccaggg aggtggagca gcagcaccag gagcaaacca gggaggtgga      60
gcagcagcac caggagcaaa ccagggaggt ggagcagca                            99

<210> SEQ ID NO 25
<211> LENGTH: 33
<212> TYPE: PRT
<213> ORGANISM: Plasmodium vivax

<400> SEQUENCE: 25

Ala Pro Gly Ala Asn Gln Gly Gly Gly Ala Ala Ala Pro Gly Ala Asn
1               5                   10                  15

Gln Gly Gly Gly Ala Ala Ala Pro Gly Ala Asn Gln Gly Gly Gly Ala
            20                  25                  30

Ala

<210> SEQ ID NO 26
<211> LENGTH: 66
<212> TYPE: PRT
<213> ORGANISM: Plasmodium vivax

<400> SEQUENCE: 26

Ala Pro Gly Ala Asn Gln Glu Gly Gly Ala Ala Ala Pro Gly Ala Asn
1               5                   10                  15

Gln Glu Gly Gly Ala Ala Ala Pro Gly Ala Asn Gln Glu Gly Gly Ala
            20                  25                  30

Ala Ala Pro Gly Ala Asn Gln Gly Gly Gly Ala Ala Ala Pro Gly Ala
        35                  40                  45

Asn Gln Gly Gly Gly Ala Ala Ala Pro Gly Ala Asn Gln Gly Gly Gly

```
<210> SEQ ID NO 27
<211> LENGTH: 66
<212> TYPE: PRT
<213> ORGANISM: Plasmodium vivax

<400> SEQUENCE: 27

Ala Pro Gly Ala Asn Gln Gly Gly Ala Ala Ala Pro Gly Ala Asn
1               5                   10                  15
Gln Gly Gly Gly Ala Ala Ala Pro Gly Ala Asn Gln Gly Gly Gly Ala
            20                  25                  30
Ala Ala Pro Gly Ala Asn Gln Glu Gly Gly Ala Ala Pro Gly Ala
        35                  40                  45
Asn Gln Glu Gly Gly Ala Ala Ala Pro Gly Ala Asn Gln Glu Gly Gly
    50                  55                  60
Ala Ala
65

<210> SEQ ID NO 28
<211> LENGTH: 246
<212> TYPE: DNA
<213> ORGANISM: Plasmodium vivax

<400> SEQUENCE: 28
caagctgctg gtggtaatgc tggtggtggt cagggtcaaa acaacgaggg tgctaatgct    60
ccaaacgaga agtccgttaa ggaatacttg gacaaagtta gagctactgt tggtactgag   120
tggactccat gttccgttac ttgtggtgtt ggtgttagag ttagaagaag agttaacgct   180
gctaacaaga agccagagga cttgactttg aacgacttgg agactgacgt ttgtactatg   240
gacaag                                                               246

<210> SEQ ID NO 29
<211> LENGTH: 82
<212> TYPE: PRT
<213> ORGANISM: Plasmodium vivax

<400> SEQUENCE: 29

Gln Ala Ala Gly Gly Asn Ala Gly Gly Gly Gln Gly Gln Asn Asn Glu
1               5                   10                  15
Gly Ala Asn Ala Pro Asn Glu Lys Ser Val Lys Glu Tyr Leu Asp Lys
            20                  25                  30
Val Arg Ala Thr Val Gly Thr Glu Trp Thr Pro Cys Ser Val Thr Cys
        35                  40                  45
Gly Val Gly Val Arg Val Arg Arg Arg Val Asn Ala Ala Asn Lys Lys
    50                  55                  60
Pro Glu Asp Leu Thr Leu Asn Asp Leu Glu Thr Asp Val Cys Thr Met
65                  70                  75                  80
Asp Lys

<210> SEQ ID NO 30
<211> LENGTH: 43
<212> TYPE: PRT
<213> ORGANISM: Plasmodium vivax

<400> SEQUENCE: 30
```

```
Glu Trp Thr Pro Cys Ser Val Thr Cys Gly Val Gly Val Arg Val Arg
1               5                   10                  15

Arg Arg Val Asn Ala Ala Asn Lys Lys Pro Glu Asp Leu Thr Leu Asn
            20                  25                  30

Asp Leu Glu Thr Asp Val Cys Thr Met Asp Lys
        35                  40
```

<210> SEQ ID NO 31
<211> LENGTH: 10
<212> TYPE: PRT
<213> ORGANISM: Plasmodium vivax

<400> SEQUENCE: 31

```
Glu Trp Thr Pro Cys Ser Val Thr Cys Gly
1               5                   10
```

<210> SEQ ID NO 32
<211> LENGTH: 6
<212> TYPE: PRT
<213> ORGANISM: Plasmodium vivax

<400> SEQUENCE: 32

```
Cys Ser Val Thr Cys Gly
1               5
```

<210> SEQ ID NO 33
<211> LENGTH: 11
<212> TYPE: PRT
<213> ORGANISM: Artificial Sequence
<220> FEATURE:
<223> OTHER INFORMATION: Insertion

<400> SEQUENCE: 33

```
Gly Ala Gly Gly Gln Ala Ala Gly Gly Asn Ala
1               5                   10
```

<210> SEQ ID NO 34
<211> LENGTH: 228
<212> TYPE: DNA
<213> ORGANISM: Plasmodium vivax

<400> SEQUENCE: 34

```
acccactgcg gccacaacgt ggacctgagc aaggccatca acctgaacgg cgtgaacttc      60
aacaatgtgg acgcctctag cctgggagct gctcacgtgg ccagagcgc cagcagaggc     120 agaggcctgg gcgagaaccc cgacgatgag gaaggcgacg ccaagaagaa gaaggacggc     180
aagaaggccg agcccaagaa ccccagagag aacaagctga gcagccc                   228
```

<210> SEQ ID NO 35
<211> LENGTH: 76
<212> TYPE: PRT
<213> ORGANISM: Plasmodium vivax

<400> SEQUENCE: 35

```
Thr His Cys Gly His Asn Val Asp Leu Ser Lys Ala Ile Asn Leu Asn
1               5                   10                  15

Gly Val Asn Phe Asn Asn Val Asp Ala Ser Ser Leu Gly Ala Ala His
            20                  25                  30

Val Gly Gln Ser Ala Ser Arg Gly Arg Gly Leu Gly Glu Asn Pro Asp
        35                  40                  45

Asp Glu Glu Gly Asp Ala Lys Lys Lys Asp Gly Lys Lys Ala Glu
    50                  55                  60
```

Pro Lys Asn Pro Arg Glu Asn Lys Leu Lys Gln Pro
65                  70                  75

<210> SEQ ID NO 36
<211> LENGTH: 5
<212> TYPE: PRT
<213> ORGANISM: Plasmodium vivax

<400> SEQUENCE: 36

Lys Leu Lys Gln Pro
1               5

<210> SEQ ID NO 37
<211> LENGTH: 690
<212> TYPE: DNA
<213> ORGANISM: Hepatitis B virus

<400> SEQUENCE: 37
ccagttacta atatggaaaa catcacttcc ggtttcttgg gtcctttgtt ggttttgcag      60
gctggattct tcttgttgac tagaatcttg actatcccac agtccttgga ctcttggtgg    120
acttccttga acttctcggg tggttcccca gtttgtttgg gtcagaactc tcaatcccca    180
acttctaacc actccccaac atcctgtcct ccaatttgtc caggttacag atggatgtgt    240
ttgagaagat tcatcatttt cttgttcatc ttgttgttgt gtttgatctt cttgttggtt    300 tgttggact accagggtat gttgccagtt tgtccattga tcccaggttc cactactaca    360
aacactggtc catgtaagac ttgtactact ccagctcagg gtaactctat gttcccttcc    420
tgttgttgta ctaagccaac tgacggtaac tgtacttgta tcccaattcc atcctcctgg    480
gctttcgcta agtacttgtg ggaatgggct tccgttagat tctcttggtt gtccttgttg    540
gttccattcg ttcagtggtt cgttggtttg tccccaactg tttggttgtc tgctatctgg    600
atgatgtggt actggggtcc atccttgtac tctatcgttt ccccattcat cccttttgttg    660 ccaatcttct tctgtttgtg ggtttacatc                                     690

<210> SEQ ID NO 38
<211> LENGTH: 230
<212> TYPE: PRT
<213> ORGANISM: Hepatitis B virus

<400> SEQUENCE: 38

Pro Val Thr Asn Met Glu Asn Ile Thr Ser Gly Phe Leu Gly Pro Leu
1               5                   10                  15

Leu Val Leu Gln Ala Gly Phe Phe Leu Leu Thr Arg Ile Leu Thr Ile
                20                  25                  30

Pro Gln Ser Leu Asp Ser Trp Trp Thr Ser Leu Asn Phe Leu Gly Gly
            35                  40                  45

Ser Pro Val Cys Leu Gly Gln Asn Ser Gln Ser Pro Thr Ser Asn His
        50                  55                  60

Ser Pro Thr Ser Cys Pro Pro Ile Cys Pro Gly Tyr Arg Trp Met Cys
65                  70                  75                  80

Leu Arg Arg Phe Ile Ile Phe Leu Phe Ile Leu Leu Leu Cys Leu Ile
                85                  90                  95

Phe Leu Leu Val Leu Leu Asp Tyr Gln Gly Met Leu Pro Val Cys Pro
                100                 105                 110

Leu Ile Pro Gly Ser Thr Thr Thr Asn Thr Gly Pro Cys Lys Thr Cys
            115                 120                 125

-continued

```
Thr Thr Pro Ala Gln Gly Asn Ser Met Phe Pro Ser Cys Cys Cys Thr
    130                 135                 140

Lys Pro Thr Asp Gly Asn Cys Thr Cys Ile Pro Ile Pro Ser Ser Trp
145                 150                 155                 160

Ala Phe Ala Lys Tyr Leu Trp Glu Trp Ala Ser Val Arg Phe Ser Trp
                165                 170                 175

Leu Ser Leu Leu Val Pro Phe Val Gln Trp Phe Val Gly Leu Ser Pro
            180                 185                 190

Thr Val Trp Leu Ser Ala Ile Trp Met Met Trp Tyr Trp Gly Pro Ser
        195                 200                 205

Leu Tyr Ser Ile Val Ser Pro Phe Ile Pro Leu Leu Pro Ile Phe Phe
    210                 215                 220

Cys Leu Trp Val Tyr Ile
225                 230

<210> SEQ ID NO 39
<211> LENGTH: 492
<212> TYPE: PRT
<213> ORGANISM: Artificial Sequence
<220> FEATURE:
<223> OTHER INFORMATION: Hepatitus B virus + Plasmodium vivax virus-like
      particle

<400> SEQUENCE: 39

Gly Asp Arg Ala Ala Gly Gln Pro Ala Gly Asp Arg Ala Ala Gly Gln
1               5                   10                  15

Pro Ala Gly Asp Arg Ala Ala Gly Gln Pro Ala Gly Asp Arg Ala Ala
            20                  25                  30

Gly Gln Pro Ala Gly Asp Arg Ala Ala Gly Gln Pro Ala Gly Asp Arg
        35                  40                  45

Ala Asp Gly Gln Pro Ala Gly Asp Arg Ala Asp Gly Gln Pro Ala Gly
    50                  55                  60

Asp Arg Ala Asp Gly Gln Pro Ala Gly Asp Arg Ala Asp Gly Gln Pro
65                  70                  75                  80

Ala Gly Asn Gly Ala Gly Gly Gln Ala Ala Ala Asn Gly Ala Gly Asn
                85                  90                  95

Gln Pro Gly Ala Asn Gly Ala Gly Gly Gln Ala Ala Ala Asn Gly Ala
            100                 105                 110

Gly Asn Gln Pro Gly Ala Asn Gly Ala Gly Gly Gln Ala Ala Ala Asn
        115                 120                 125

Gly Ala Gly Asp Gln Pro Gly Ala Asn Gly Ala Gly Asp Gln Pro Gly
    130                 135                 140

Ala Asn Gly Ala Asp Asp Gln Pro Gly Ala Asn Gly Ala Gly Asp Gln
145                 150                 155                 160

Pro Gly Glu Asp Gly Ala Gly Asn Gln Pro Gly Ala Asn Gly Ala Gly
                165                 170                 175

Asp Gln Pro Gly Gln Ala Ala Gly Gly Asn Ala Gly Gly Gly Gln Gly
            180                 185                 190

Gln Asn Asn Glu Gly Ala Asn Ala Pro Asn Glu Lys Ser Val Lys Glu
        195                 200                 205

Tyr Leu Asp Lys Val Arg Ala Thr Val Gly Thr Glu Trp Thr Pro Cys
    210                 215                 220

Ser Val Thr Cys Gly Val Gly Val Arg Val Arg Arg Arg Val Asn Ala
225                 230                 235                 240

Ala Asn Lys Lys Pro Glu Asp Leu Thr Leu Asn Asp Leu Glu Thr Asp
                245                 250                 255
```

```
Val Cys Thr Met Asp Lys Pro Val Thr Asn Met Glu Asn Ile Thr Ser
            260                 265                 270

Gly Phe Leu Gly Pro Leu Leu Val Leu Gln Ala Gly Phe Leu Leu
            275                 280                 285

Thr Arg Ile Leu Thr Ile Pro Gln Ser Leu Asp Ser Trp Trp Thr Ser
            290                 295                 300

Leu Asn Phe Leu Gly Gly Ser Pro Val Cys Leu Gly Gln Asn Ser Gln
305                 310                 315                 320

Ser Pro Thr Ser Asn His Ser Pro Thr Ser Cys Pro Pro Ile Cys Pro
                325                 330                 335

Gly Tyr Arg Trp Met Cys Leu Arg Arg Phe Ile Ile Phe Leu Phe Ile
            340                 345                 350

Leu Leu Leu Cys Leu Ile Phe Leu Leu Val Leu Leu Asp Tyr Gln Gly
            355                 360                 365

Met Leu Pro Val Cys Pro Leu Ile Pro Gly Ser Thr Thr Thr Asn Thr
370                 375                 380

Gly Pro Cys Lys Thr Cys Thr Thr Pro Ala Gln Gly Asn Ser Met Phe
385                 390                 395                 400

Pro Ser Cys Cys Cys Thr Lys Pro Thr Asp Gly Asn Cys Thr Cys Ile
            405                 410                 415

Pro Ile Pro Ser Ser Trp Ala Phe Ala Lys Tyr Leu Trp Glu Trp Ala
            420                 425                 430

Ser Val Arg Phe Ser Trp Leu Ser Leu Leu Val Pro Phe Val Gln Trp
            435                 440                 445

Phe Val Gly Leu Ser Pro Thr Val Trp Leu Ser Ala Ile Trp Met Met
            450                 455                 460

Trp Tyr Trp Gly Pro Ser Leu Tyr Ser Ile Val Ser Pro Phe Ile Pro
465                 470                 475                 480

Leu Leu Pro Ile Phe Phe Cys Leu Trp Val Tyr Ile
                485                 490

<210> SEQ ID NO 40
<211> LENGTH: 556
<212> TYPE: PRT
<213> ORGANISM: Plasmodium vivax

<400> SEQUENCE: 40

Met Lys Leu Leu Gln Asn Lys Ser Tyr Leu Leu Val Val Phe Leu Leu
1               5                   10                  15

Tyr Val Ser Ile Phe Ala Arg Gly Asp Glu Lys Val Val Asp Glu Val
            20                  25                  30

Lys Tyr Ser Glu Glu Val Cys Asn Glu Ser Val Asp Leu Tyr Leu Leu
        35                  40                  45

Val Asp Gly Ser Gly Ser Ile Gly Tyr Pro Asn Trp Ile Thr Lys Val
    50                  55                  60

Ile Pro Met Leu Asn Gly Leu Ile Asn Ser Leu Ser Leu Ser Arg Asp
65                  70                  75                  80

Thr Ile Asn Leu Tyr Met Asn Leu Phe Gly Asn Tyr Thr Thr Glu Leu
                85                  90                  95

Ile Arg Leu Gly Ser Gly Gln Ser Ile Asp Lys Arg Gln Ala Leu Ser
            100                 105                 110

Lys Val Thr Glu Leu Arg Lys Thr Tyr Thr Pro Tyr Gly Thr Thr Asn
        115                 120                 125

Met Thr Ala Ala Leu Asp Glu Val Gln Lys His Leu Asn Asp Arg Val
```

```
            130                 135                 140
Asn Arg Glu Lys Ala Ile Gln Leu Val Ile Leu Met Thr Asp Gly Val
145                 150                 155                 160

Pro Asn Ser Lys Tyr Arg Ala Leu Glu Val Ala Asn Lys Leu Lys Gln
                165                 170                 175

Arg Asn Val Ser Leu Ala Val Ile Gly Ile Gly Gln Gly Ile Asn His
                180                 185                 190

Gln Phe Asn Arg Leu Ile Ala Gly Cys Arg Pro Arg Glu Pro Asn Cys
                195                 200                 205

Lys Phe Tyr Ser Tyr Ala Asp Trp Asn Glu Ala Val Ala Leu Ile Lys
                210                 215                 220

Pro Phe Ile Ala Lys Val Cys Thr Glu Val Glu Arg Val Ala Asn Cys
225                 230                 235                 240

Gly Pro Trp Asp Pro Trp Thr Ala Cys Ser Val Thr Cys Gly Arg Gly
                245                 250                 255

Thr His Ser Arg Ser Arg Pro Ser Leu His Glu Lys Cys Thr Thr His
                260                 265                 270

Met Val Ser Glu Cys Glu Gly Glu Cys Pro Val Glu Pro Glu Pro
                275                 280                 285

Leu Pro Val Pro Ala Pro Leu Pro Thr Val Pro Glu Asp Val Asn Pro
290                 295                 300

Arg Asp Thr Asp Glu Asn Glu Asn Pro Asn Phe Asn Lys Gly Leu
305                 310                 315                 320

Asp Val Pro Asp Glu Asp Asp Glu Val Pro Pro Ala Asn Glu Arg
                325                 330                 335

Ala Asp Gly Asn Pro Val Glu Glu Asn Val Phe Pro Pro Ala Asp Asp
                340                 345                 350

Ser Val Pro Asp Glu Ser Asn Val Leu Pro Leu Pro Pro Ala Val Pro
                355                 360                 365

Gly Gly Ser Ser Glu Glu Phe Pro Ala Asp Val Gln Asn Asn Pro Asp
                370                 375                 380

Ser Pro Glu Glu Leu Pro Met Glu Gln Glu Val Pro Gln Asp Asn Asn
385                 390                 395                 400

Val Asn Glu Pro Glu Arg Ser Asp Ser Lys Gly Tyr Gly Val Asn Glu
                405                 410                 415

Lys Val Ile Pro Asn Pro Leu Asp Asn Glu Arg Asp Met Ala Asn Lys
                420                 425                 430

Asn Lys Thr Val His Pro Gly Arg Lys Asp Ser Ala Arg Asp Arg Tyr
                435                 440                 445

Ala Arg Pro His Gly Ser Thr His Val Asn Asn Arg Ala Asn Glu
                450                 455                 460

Asn Ser Asp Ile Pro Asn Pro Val Pro Ser Asp Tyr Glu Gln Pro
465                 470                 475                 480

Glu Asp Lys Ala Lys Lys Ser Ser Asn Asn Gly Tyr Lys Ile Ala Gly
                485                 490                 495

Gly Val Ile Ala Gly Leu Ala Leu Val Gly Cys Val Gly Phe Ala Tyr
                500                 505                 510

Asn Phe Val Ala Gly Gly Ala Ala Gly Met Ala Gly Glu Pro Ala
                515                 520                 525

Pro Phe Asp Glu Ala Met Ala Glu Asp Glu Lys Asp Val Ala Glu Ala
530                 535                 540

Asp Gln Phe Lys Leu Pro Glu Asp Asn Glu Trp Asn
545                 550                 555
```

<210> SEQ ID NO 41
<211> LENGTH: 469
<212> TYPE: PRT
<213> ORGANISM: Plasmodium vivax

<400> SEQUENCE: 41

```
Asp Glu Lys Val Val Asp Glu Val Lys Tyr Ser Glu Val Cys Asn
1               5                   10                  15

Glu Ser Val Asp Leu Tyr Leu Leu Val Asp Gly Ser Gly Ser Ile Gly
            20                  25                  30

Tyr Pro Asn Trp Ile Thr Lys Val Ile Pro Met Leu Asn Gly Leu Ile
                35                  40                  45

Asn Ser Leu Ser Leu Ser Arg Asp Thr Ile Asn Leu Tyr Met Asn Leu
50                  55                  60

Phe Gly Asn Tyr Thr Thr Glu Leu Ile Arg Leu Gly Ser Gly Gln Ser
65                  70                  75                  80

Ile Asp Lys Arg Gln Ala Leu Ser Lys Val Thr Glu Leu Arg Lys Thr
                85                  90                  95

Tyr Thr Pro Tyr Gly Thr Thr Asn Met Thr Ala Ala Leu Asp Glu Val
            100                 105                 110

Gln Lys His Leu Asn Asp Arg Val Asn Arg Glu Lys Ala Ile Gln Leu
        115                 120                 125

Val Ile Leu Met Thr Asp Gly Val Pro Asn Ser Lys Tyr Arg Ala Leu
130                 135                 140

Glu Val Ala Asn Lys Leu Lys Gln Arg Asn Val Ser Leu Ala Val Ile
145                 150                 155                 160

Gly Val Gly Gln Gly Ile Asn His Gln Phe Asn Arg Leu Ile Ala Gly
                165                 170                 175

Cys Arg Pro Arg Glu Pro Asn Cys Lys Phe Tyr Ser Tyr Ala Asp Trp
            180                 185                 190

Asn Glu Ala Val Ala Leu Ile Lys Pro Phe Ile Ala Lys Val Cys Thr
        195                 200                 205

Glu Val Glu Arg Val Ala Asn Cys Gly Pro Trp Asp Pro Trp Thr Ala
210                 215                 220

Cys Ser Val Thr Cys Gly Arg Gly Thr His Ser Arg Ser Arg Pro Ser
225                 230                 235                 240

Leu His Glu Lys Cys Thr Thr His Met Val Ser Glu Cys Glu Glu Gly
                245                 250                 255

Glu Cys Pro Val Glu Pro Glu Pro Leu Pro Val Pro Ala Pro Leu Pro
            260                 265                 270

Thr Val Pro Glu Asp Val Asn Pro Arg Asp Thr Asp Glu Asn Glu
        275                 280                 285

Asn Pro Asn Phe Asn Lys Gly Leu Asp Val Pro Asp Glu Asp Asp
290                 295                 300

Glu Val Pro Pro Ala Asn Glu Gly Ala Asp Gly Asn Pro Val Glu Glu
305                 310                 315                 320

Asn Val Phe Pro Pro Ala Asp Asp Ser Val Pro Asp Glu Ser Asn Val
                325                 330                 335

Leu Pro Leu Pro Pro Ala Val Pro Gly Gly Ser Ser Glu Glu Phe Pro
            340                 345                 350

Ala Asp Val Gln Asn Asn Pro Asp Ser Pro Glu Glu Leu Pro Met Glu
        355                 360                 365

Gln Glu Val Pro Gln Asp Asn Asn Val Asn Glu Pro Glu Arg Ser Asp
```

```
                    370                 375                 380
Ser Asn Gly Tyr Gly Val Asn Glu Lys Val Ile Pro Asn Pro Leu Asp
385                 390                 395                 400

Asn Glu Arg Asp Met Ala Asn Lys Asn Lys Thr Val His Pro Gly Arg
                405                 410                 415

Lys Asp Ser Ala Arg Asp Arg Tyr Ala Arg Pro His Gly Ser Thr His
            420                 425                 430

Val Asn Asn Arg Ala Asn Glu Asn Ser Asp Ile Pro Asn Asn Pro
        435                 440                 445

Val Pro Ser Asp Tyr Glu Gln Pro Glu Asp Lys Ala Lys Lys Ser Ser
    450                 455                 460

Asn Asn Gly Tyr Lys
465

<210> SEQ ID NO 42
<211> LENGTH: 12
<212> TYPE: DNA
<213> ORGANISM: Artificial Sequence
<220> FEATURE:
<223> OTHER INFORMATION: C-tag

<400> SEQUENCE: 42
gagcccgagg cc                                                         12

<210> SEQ ID NO 43
<211> LENGTH: 4
<212> TYPE: PRT
<213> ORGANISM: Artificial Sequence
<220> FEATURE:
<223> OTHER INFORMATION: C-tag

<400> SEQUENCE: 43

Glu Pro Glu Ala
1

<210> SEQ ID NO 44
<211> LENGTH: 597
<212> TYPE: DNA
<213> ORGANISM: Plasmodium vivax

<400> SEQUENCE: 44
atggccgtca cggtagacac catatgcaaa aatggacagc tggttcaaat gagtaaccac        60
tttaagtgta tgtgtaacga agggctggtg cacctttccg aaaatacatg tgaagaaaaa       120
aatgaatgca agaaagaaac cctaggcaaa gcatgcgggg aatttggcca gtgtatagaa       180
aacccagacc cagcacaggt aaacatgtac aaatgtggtt gcattgaggg ctacactttg       240
aaggaagaca cttgtgtgct tgatgtatgt caatacaaaa attgtggaga agtggcgaa        300 tgcattgttg agtacctctc ggaaatccaa agtgcaggtt gctcatgtgc tattggcaaa       360
gtccccaatc agaagatga gaaaaaatgt accaaaacgg agaaactgc ttgtcaattg         420 aaatgtaaca cagataatga agtctgcaaa aatgttgaag gagtttacaa gtgccagtgt       480
atggaaggct ttacgttcga caaagagaaa aatgtatgcc tttcctattc tgtatttaac       540
atcctaaact actccctctt ctttatcatc ctgcttgtcc tttcgtacgt catataa          597

<210> SEQ ID NO 45
<211> LENGTH: 198
<212> TYPE: PRT
<213> ORGANISM: Plasmodium vivax
```

<400> SEQUENCE: 45

```
Met Ala Val Thr Val Asp Thr Ile Cys Lys Asn Gly Gln Leu Val Gln
1               5                   10                  15

Met Ser Asn His Phe Lys Cys Met Cys Asn Glu Gly Leu Val His Leu
            20                  25                  30

Ser Glu Asn Thr Cys Glu Glu Lys Asn Glu Cys Lys Lys Glu Thr Leu
        35                  40                  45

Gly Lys Ala Cys Gly Glu Phe Gly Gln Cys Ile Glu Asn Pro Asp Pro
    50                  55                  60

Ala Gln Val Asn Met Tyr Lys Cys Gly Cys Ile Glu Gly Tyr Thr Leu
65                  70                  75                  80

Lys Glu Asp Thr Cys Val Leu Asp Val Cys Gln Tyr Lys Asn Cys Gly
                85                  90                  95

Glu Ser Gly Glu Cys Ile Val Glu Tyr Leu Ser Glu Ile Gln Ser Ala
            100                 105                 110

Gly Cys Ser Cys Ala Ile Gly Lys Val Pro Asn Pro Glu Asp Glu Lys
        115                 120                 125

Lys Cys Thr Lys Thr Gly Glu Thr Ala Cys Gln Leu Lys Cys Asn Thr
    130                 135                 140

Asp Asn Glu Val Cys Lys Asn Val Glu Gly Val Tyr Lys Cys Gln Cys
145                 150                 155                 160

Met Glu Gly Phe Thr Phe Asp Lys Glu Lys Asn Val Cys Leu Ser Tyr
                165                 170                 175

Ser Val Phe Asn Ile Leu Asn Tyr Ser Leu Phe Phe Ile Ile Leu Leu
            180                 185                 190

Val Leu Ser Tyr Val Ile
        195
```

<210> SEQ ID NO 46
<211> LENGTH: 215
<212> TYPE: PRT
<213> ORGANISM: Plasmodium vivax

<400> SEQUENCE: 46

```
Met Lys Val Thr Ala Glu Thr Gln Cys Lys Asn Gly Tyr Val Val Gln
1               5                   10                  15

Met Ser Asn His Phe Glu Cys Lys Cys Asn Asp Gly Phe Val Met Ala
            20                  25                  30

Asn Glu Asn Thr Cys Glu Glu Lys Arg Asp Cys Thr Asn Pro Gln Asn
        35                  40                  45

Val Asn Lys Asn Cys Gly Asp Tyr Ala Val Cys Ala Asn Thr Arg Met
    50                  55                  60

Asn Asp Glu Glu Arg Ala Leu Arg Cys Gly Cys Ile Leu Gly Tyr Thr
65                  70                  75                  80

Val Met Asn Glu Val Cys Thr Pro Asn Lys Cys Asn Gly Val Leu Cys
                85                  90                  95

Gly Lys Gly Lys Cys Ile Leu Asp Pro Ala Asn Val Asn Ser Thr Met
            100                 105                 110

Cys Ser Cys Asn Ile Gly Thr Thr Leu Asp Glu Ser Lys Lys Cys Gly
        115                 120                 125

Lys Pro Gly Lys Thr Glu Cys Thr Leu Lys Cys Lys Ala Asn Glu Glu
    130                 135                 140

Cys Lys Glu Thr Gln Asn Tyr Tyr Lys Cys Val Ala Lys Gly Ser Gly
145                 150                 155                 160
```

```
Gly Glu Gly Ser Gly Gly Glu Gly Ser Gly Gly Glu Gly Ser Gly
            165                 170                 175

Glu Gly Ser Gly Gly Glu Gly Ser Gly Gly Asp Thr Gly Ala Ala Tyr
            180                 185                 190

Ser Leu Met Asn Gly Ser Ala Val Ile Ser Ile Leu Leu Val Phe Ala
            195                 200                 205

Phe Phe Met Met Ser Leu Val
            210             215

<210> SEQ ID NO 47
<211> LENGTH: 412
<212> TYPE: PRT
<213> ORGANISM: Plasmodium vivax

<400> SEQUENCE: 47

Met Ala Val Thr Val Asp Thr Ile Cys Lys Asn Gly Gln Leu Val Gln
1               5                   10                  15

Met Ser Asn His Phe Lys Cys Met Cys Asn Glu Gly Leu Val His Leu
            20                  25                  30

Ser Glu Asn Thr Cys Glu Glu Lys Asn Glu Cys Lys Lys Glu Thr Leu
        35                  40                  45

Gly Lys Ala Cys Gly Glu Phe Gly Gln Cys Ile Glu Asn Pro Asp Pro
    50                  55                  60

Ala Gln Val Asn Met Tyr Lys Cys Gly Cys Ile Glu Gly Tyr Thr Leu
65                  70                  75                  80

Lys Glu Asp Thr Cys Val Leu Asp Val Cys Gln Tyr Lys Asn Cys Gly
                85                  90                  95

Glu Ser Gly Glu Cys Ile Val Glu Tyr Leu Ser Glu Ile Gln Ser Ala
            100                 105                 110

Gly Cys Ser Cys Ala Ile Gly Lys Val Pro Asn Pro Glu Asp Glu Lys
        115                 120                 125

Lys Cys Thr Lys Thr Gly Glu Thr Ala Cys Gln Leu Lys Cys Asn Thr
    130                 135                 140

Asp Asn Glu Val Cys Lys Asn Val Gly Val Tyr Lys Cys Gln Cys
145                 150                 155                 160

Met Glu Gly Phe Thr Phe Asp Lys Glu Lys Asn Val Cys Leu Ser Tyr
                165                 170                 175

Ser Val Phe Asn Ile Leu Asn Tyr Ser Leu Phe Phe Ile Ile Leu Leu
            180                 185                 190

Val Leu Ser Tyr Val Ile Lys Val Thr Ala Glu Thr Gln Cys Lys Asn
        195                 200                 205

Gly Tyr Val Val Gln Met Ser Asn His Phe Glu Cys Lys Cys Asn Asp
    210                 215                 220

Gly Phe Val Met Ala Asn Glu Asn Thr Cys Glu Lys Arg Asp Cys
225                 230                 235                 240

Thr Asn Pro Gln Asn Val Asn Lys Asn Cys Gly Asp Tyr Ala Val Cys
                245                 250                 255

Ala Asn Thr Arg Met Asn Asp Glu Glu Arg Ala Leu Arg Cys Gly Cys
            260                 265                 270

Ile Leu Gly Tyr Thr Val Met Asn Glu Val Cys Thr Pro Asn Lys Cys
        275                 280                 285

Asn Gly Val Leu Cys Gly Lys Gly Lys Cys Ile Leu Asp Pro Ala Asn
    290                 295                 300

Val Asn Ser Thr Met Cys Ser Cys Asn Ile Gly Thr Thr Leu Asp Glu
305                 310                 315                 320
```

```
Ser Lys Lys Cys Gly Lys Pro Gly Lys Thr Glu Cys Thr Leu Lys Cys
            325                 330                 335

Lys Ala Asn Glu Glu Cys Lys Glu Thr Gln Asn Tyr Tyr Lys Cys Val
        340                 345                 350

Ala Lys Gly Ser Gly Gly Glu Gly Ser Gly Gly Glu Gly Ser Gly Gly
    355                 360                 365

Glu Gly Ser Gly Gly Glu Gly Ser Gly Gly Glu Gly Ser Gly Gly Asp
370                 375                 380

Thr Gly Ala Ala Tyr Ser Leu Met Asn Gly Ser Ala Val Ile Ser Ile
385                 390                 395                 400

Leu Leu Val Phe Ala Phe Phe Met Met Ser Leu Val
            405                 410

<210> SEQ ID NO 48
<211> LENGTH: 22
<212> TYPE: DNA
<213> ORGANISM: Artificial Sequence
<220> FEATURE:
<223> OTHER INFORMATION: PvCSP-trans (F6) primer

<400> SEQUENCE: 48
tgacatgcat atgtgttggt tg                                            22

<210> SEQ ID NO 49
<211> LENGTH: 20
<212> TYPE: DNA
<213> ORGANISM: Artificial Sequence
<220> FEATURE:
<223> OTHER INFORMATION: PvCSP-trans (R5) primer

<400> SEQUENCE: 49
gctgattgtc caacatgtgc                                               20

<210> SEQ ID NO 50
<211> LENGTH: 24
<212> TYPE: DNA
<213> ORGANISM: Artificial Sequence
<220> FEATURE:
<223> OTHER INFORMATION: 1054 primer

<400> SEQUENCE: 50
ccaaaggaac ttaaacgagc tatg                                          24

<210> SEQ ID NO 51
<211> LENGTH: 24
<212> TYPE: DNA
<213> ORGANISM: Artificial Sequence
<220> FEATURE:
<223> OTHER INFORMATION: 1055 primer

<400> SEQUENCE: 51
cttataccag aaccacatgt tacg                                          24

<210> SEQ ID NO 52
<211> LENGTH: 24
<212> TYPE: DNA
<213> ORGANISM: Artificial Sequence
<220> FEATURE:
<223> OTHER INFORMATION: 7393 primer

<400> SEQUENCE: 52
atcgactagt aaagcctcgc tacg                                          24
```

```
<210> SEQ ID NO 53
<211> LENGTH: 25
<212> TYPE: DNA
<213> ORGANISM: Artificial Sequence
<220> FEATURE:
<223> OTHER INFORMATION: 7394 primer

<400> SEQUENCE: 53
gtgagtcaga tggactttct ggtag                                25
```